United States Patent
Klein et al.

(10) Patent No.: US 11,858,951 B2
(45) Date of Patent: Jan. 2, 2024

(54) BORONIC ACID DERIVATIVES

(71) Applicant: Merck Patent GmbH, Darmstadt (DE)

(72) Inventors: Markus Klein, Darmstadt (DE); Oliver Schadt, Rodenbach (DE); Christina Esdar, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 17/649,411

(22) Filed: Jan. 31, 2022

(65) Prior Publication Data

US 2022/0153761 A1    May 19, 2022

Related U.S. Application Data

(63) Continuation of application No. 16/640,669, filed as application No. PCT/EP2018/072485 on Aug. 21, 2018, now Pat. No. 11,274,109.

(30) Foreign Application Priority Data

Aug. 24, 2017 (EP) ..................................... 17187636

(51) Int. Cl.
| | | |
|---|---|---|
| *C07F 5/02* | (2006.01) | |
| *A61P 43/00* | (2006.01) | |
| *A61K 31/69* | (2006.01) | |
| *A61K 45/06* | (2006.01) | |

(52) U.S. Cl.
CPC ............... *C07F 5/025* (2013.01); *A61K 31/69* (2013.01); *A61K 45/06* (2013.01); *A61P 43/00* (2018.01)

(58) Field of Classification Search
CPC ........................................................ C07F 5/025
USPC ........................................................... 514/64
See application file for complete search history.

(56) References Cited

U.S. PATENT DOCUMENTS

| | | |
|---|---|---|
| 9,464,098 B2 | 10/2016 | Lynch et al. |
| 9,688,702 B2 | 6/2017 | Swinnen et al. |
| 10,253,049 B2 | 4/2019 | Klein et al. |
| 10,294,246 B2 | 5/2019 | Klein et al. |
| 10,640,520 B2 | 5/2020 | Klein et al. |
| 10,669,289 B2 | 6/2020 | Klein et al. |
| 2014/0364396 A1 | 12/2014 | Swinnen et al. |
| 2015/0329565 A1 | 11/2015 | Lynch et al. |

FOREIGN PATENT DOCUMENTS

| | | |
|---|---|---|
| CN | 107001390 | 8/2017 |
| CN | 107001391 | 8/2017 |
| CN | 107074885 | 8/2017 |
| IN | 201717005270 | 5/2017 |
| IN | 201717005271 | 5/2017 |
| IN | 201717005272 | 5/2017 |
| IN | 201717005907 | 6/2017 |
| RU | 2625801 | 7/2017 |
| WO | 2013/092979 | 6/2013 |
| WO | 2016/050355 | 4/2016 |
| WO | 2016/050356 | 4/2016 |
| WO | 2016/050358 | 4/2016 |
| WO | 2016/050359 | 4/2016 |

OTHER PUBLICATIONS

International Search Report dated Oct. 31, 2018 in PCT/EP2018/072485.
Written Opinion dated Oct. 31, 2018 in PCT/EP2018/072485.
Alekseev V.V., Optičeskaâ isomeriâ i farmakologičeskaâ aktivnost' lekarstvennyh preparatov [Optical isomerisms and pharmacological activity of medicaments], Sorosovskij obrazovate'nyj žurnal, 1, 1998, pp. 49-55.
Belikov V. G., Pharmacevtičeskaâ himiâ [Pharmaceutical Chemistry] Moscow: MEDpressinform, 2007, pp. 27-29.
Dyson G et al., Himiâ sintetičeskih lekarstvennyh sredstv [Chemistry of synthetic Drugs], Moscow: Mir, 1964, pp. 12-19.
Maškovskij M. D., Lekarstvennye sredstva [Medicaments], Moscow: Medicina, 1993, vol. 1, p. 8.
Maškovskij M. D., Lekarstvennye sredstva [Medicaments], Moscow: Novaâ volna, 2001, vol. 1, p. 11.
Russian Office Action dated Feb. 28, 2022 in Russian Application No. 2020111001, with partial English translation, 22 pages.

*Primary Examiner* — Taofiq A Solola
(74) *Attorney, Agent, or Firm* — Grüneberg and Myers PLLC

(57) ABSTRACT

α-Amino boronic acid derivatives are useful for inhibiting the activity of immunoproteasome (LMP7) and for the treatment and/or prevention of medical conditions affected by immunoproteasome activity such as inflammatory and autoimmune diseases, neurodegenerative diseases, proliferative diseases, and cancer.

16 Claims, No Drawings

BORONIC ACID DERIVATIVES

CROSS-REFERENCE TO RELATED APPLICATIONS

This application is a continuation of U.S. application Ser. No. 16/640,669, filed on Feb. 20, 2020, which was the National Stage entry under § 371 of International Application No, PCT/EP2018/072485, filed on Aug. 21, 2018, and which claims the benefit of priority to European Application No. 17187636.0, filed on Aug. 24, 2017. The content of each of these applications is hereby incorporated by reference in its entirety.

FIELD OF THE INVENTION

The present invention relates to α-amino boronic acid derivatives. These compounds are useful for inhibiting the activity of immunoproteasome (LMP7) and for the treatment and/or prevention of medical conditions affected by immunoproteasome activity such as inflammatory and autoimmune diseases, neurodegenerative diseases, proliferative diseases and cancer. In particular, the compounds of the present invention are selective immunoproteasome inhibitors.

BACKGROUND OF THE INVENTION

The proteasome (also known as macropain, the multicatalytic protease, and 20S protease) is a high molecular weight, multisubunit protease which has been identified in every examined species from an archaebacterium to human. The enzyme has a native molecular weight of approximately 650,000 and, as revealed by electron microscopy, a distinctive cylinder-shaped morphology (Rivett, (1989) Arch. Biochem. Biophys. 268:1-8; and Orlowski, (1990) Biochemistry 29:10289-10297). The proteasome subunits range in molecular weight from 20,000 to 35,000, and are homologous to one another but not to any other known protease.

The 20S proteasome is a 700 kDa cylindrical-shaped multicatalytic protease complex comprised of 28 subunits, classified as α- and β-type, that are arranged in 4 stacked heptameric rings. In yeast and other eukaryotes, 7 different a subunits form the outer rings and 7 different β subunits comprise the inner rings. The a subunits serve as binding sites for the 19S (PA700) and 1 IS (PR68) regulatory complexes, as well as a physical barrier for the inner proteolytic chamber formed by the two β subunit rings. Thus, in vivo, the proteasome is believed to exist as a 26S particle ("the 26S proteasome"). In vivo experiments have shown that inhibition of the 20S form of the proteasome can be readily correlated to inhibition of 26S proteasome.

Cleavage of amino-terminal prosequences of β subunits during particle formation expose amino-terminal threonine residues, which serve as the catalytic nucleophiles. The subunits responsible for catalytic activity in proteasome thus possess an amino terminal nucleophilic residue, and these subunits belong to the family of N-terminal nucleophile (Ntn) ATTY REF: 26500-0023WO1 hydrolases (where the nucleophilic N-terminal residue is, for example, Cys, Ser, Thr, and other nucleophilic moieties). This family includes, for example, penicillin G acylase (PGA), penicillin V acylase (PVA), glutamine PRPP amidotransferase (GAT), and bacterial glycosylasparaginase. In addition to the ubiquitously expressed β subunits, higher vertebrates also possess three interferon-γ-inducible β subunits (LMP7, LMP2 and MECLI), which replace their normal counterparts, β5, β1 and β2, respectively. When all three IFN-γ-inducible subunits are present, the proteasome is referred to as an "immunoproteasome". Thus, eukaryotic cells can possess two forms of proteasomes in varying ratios.

Through the use of different peptide substrates, three major proteolytic activities have been defined for the eukaryote 20S proteasomes: chymotrypsin-like activity (CT-L), which cleaves after large hydrophobic residues; trypsin-like activity (T-L), which cleaves after basic residues; and peptidylglutamyl peptide hydrolyzing activity (PGPH), which cleaves after acidic residues. Two additional less characterized activities have also been ascribed to the proteasome: BrAAP activity, which cleaves after branched-chain amino acids; and SNAAP activity, which cleaves after small neutral amino acids. Although both forms of the proteasome possess all five enzymatic activities, differences in the extent of the activities between the forms have been described based on specific substrates. For both forms of the proteasome, the major proteasome proteolytic activities appear to be contributed by different catalytic sites within the 20S core.

In eukaryotes, protein degradation is predominately mediated through the ubiquitin pathway in which proteins targeted for destruction are ligated to the 76 amino acid polypeptide ubiquitin. Once targeted, ubiquitinated proteins then serve as substrates for the 26S proteasome, which cleaves proteins into short peptides through the action of its three major proteolytic activities. While having a general function in intracellular protein turnover, proteasome-mediated degradation also plays a key role in many processes such as major histocompatibility complex (MHC) class I presentation, apoptosis and cell viability, antigen processing, NF-κB activation, and transduction of pro-inflammatory signals.

Proteasome activity is high in muscle wasting diseases that involve protein breakdown such as muscular dystrophy, cancer and AIDS. Evidence also suggests a possible role for the proteasome in the processing of antigens for the class I MHC molecules (Goldberg, et al. (1992) Nature 357:375-379).

Proteasomes are involved in neurodegenerative diseases and disorders such as Amyotrophic Lateral Sclerosis (ALS), (J Biol Chem 2003, Allen S et al., Exp Neurol 2005, Puttaparthi k et al.), Sjogren Syndrome (Arthritis & Rheumatism, 2006, Egerer T et al.), systemic lupus erythematoses and lupus nephritis (SLE/LN), (Arthritis & rheuma 2011, Ichikawa et al., J Immunol, 2010, Lang V R et al., Nat Med, 2008, Neubert K et al), glomerulonephritis (J Am Soc nephrol 2011, Bontscho et al.), Rheumatoid Arthritis (Clin Exp Rheumatol, 2009, Van der Heiden J W et al.), Inflammatory bowel disease (IBD), ulcerative colitis, crohn's diseases, (Gut 2010, Schmidt N et al., J Immunol 2010, Basler M et al., Clin Exp Immunol, 2009, Inoue S et al.), multiple sclerosis (Eur J Immunol 2008, Fissolo N et al., J Mol Med 2003, Elliott P J et al., J Neuroimmunol 2001, Hosseini et al., J Autoimmun 2000, Vanderlugt C L et al.), Amyotrophic lateral sclerosis (ALS), (Exp Neurol 2005, Puttaparthi k et al., J Biol Chem 2003, Allen S et al.), osteoarthritis (Pain 2011, Ahmed s et al., Biomed Mater Eng 2008, Etienne S et al.), Atherosclerosis (J Cardiovasc Pharmacol 2010, Feng B et al., Psoriasis (Genes & Immunity, 2007, Kramer U et al.), Myasthenia Gravis (J Immunol, 2011, Gomez A M et al.), Dermal fibrosis (Thorax 2011, Mutlu G M et al., Inflammation 2011, Koca S S et al., Faseb J 2006, Fineschi S et al.), renal fibrosis (Nephrology 2011 Sakairi T et al.), cardiac fibrosis (Biochem Pharmacol 2011, May et al.) Liver fibrosis (Am J Physiol gastrointest Liver Physiol 2006, Anan A et al.), Lung fibrosis (Faseb J 2006, Fineschi S et al et al.), Imunoglobuline A nephropathy (IGa nephropathy), (Kidney Int, 2009, Coppo R et al.), Vasculitis (J Am Soc nephrol 2011, Bontscho et al.), Transplant rejection (Nephrol Dial transplant 2011, Waiser J et al.), Hematological malignancies (Br J Haematol 2011, singh A V et al., Curr Cancer Drug Target 2011, Chen D et al.) and asthma.

Yet, it should be noted that commercially available proteasome inhibitors inhibit both the constitutive and immuno-forms of the proteasome. Even bortezomib, the FDA-approved proteasome inhibitor for the treatment of relapsed multiple myeloma patients, does not distinguish between the two forms (Altun et al, Cancer Res 65:7896, 2005). Furthermore, the use of Bortezomib is associated with a treatment-emergent, painful peripheral neuropathy (PN), this bortezomib-induced neurodegeneration in vitro occurs via a proteasome-independent mechanism and that bortezomib inhibits several nonproteasomal targets in vitro and in vivo (Clin. Cancer Res, 17(9), May 1, 2011).

In addition to conventional proteasome inhibitors, a novel approach may be to specifically target the hematological-specific immunoproteasome, thereby increasing overall effectiveness and reducing negative off-target effects. It has been shown that immunoproteasome-specific inhibitor, could display enhanced efficiency on cells from a hematologic origin (Curr Cancer Drug Targets, 11(3), March, 2011).

Thus there is a need to provide new proteasome inhibitors that are selective of one specific form of the proteasome. In particular there is a need to provide selective immunoproteasome inhibitors, which could be used as therapeutic agents for the treatment of e.g. SLE or other immune or autoimmune disorders in the context of rheumatoid arthritis. Selective immunoproteasome inhibitors are helpful in order to minimize unwanted side effects mediated by inhibition of the constitutive proteasome or other nonproteasomal targets.

WO 2013/092979 A1 describes boronic acid derivatives, which show selectively towards the inhibition of the LMP7 activity. However, the extent of selectivity, which is achievable with the described types of compounds, is limited, particularly with respect to the split to the inhibitory activity of the constitutive proteasome.

Unspecific inhibitors of the proteasome and the immunoproteasome like Bortezomib and Carfilzomib have demonstrated their clinical value in the indication of multiple myeloma. Although this unspecific profile, hitting major components in the immunoproteasome as well as the constitutive proteasome, is regarded beneficial in terms of target inhibition and clinical effectiveness, this unspecific profile limits the clinical applicability of these agents by inducing pronounced side effects like thrombocytopenia, neutropenia as well as peripheral neuropathy. To a certain extent, this side effect profile could be attributed to the broad inhibition of the catalytic activity, especially the combined inhibition of the ß5 subunits of the constitutive and the immoproteasome. The approach to come up with more selective inhibitors of the immunoproteasome (and especially the ß5i subunit of the immunoproteasome), in order to reduce major side effects has been described e.g. in 2011 by Singh et al (Br. J. Hematology 152(2): 155-163) for PR-924, a 100 fold selective inhibitor of the LMP7 subunit of the immunoproteasome. The authors demonstrated the presence of high expression levels of the immunoproteasome in multiple myeloma. The authors also described the effect of a selective inhibitor of the LMP7 subunit on the induction of cell death in MM cell lines as well as CD138+ MM primary patient cells without decreasing the viability of control PBMC's of healthy volunteers which can be regarded as a conceptual proof. Beside the concept of a reduced side effect profile for selective ß5i inhibitors other group demonstrated the efficacy of selective 115i inhibition on the viability of Bortezomib resistant cell lines underlining the value and potential perspective for the application of selective LMP7 inhibitors for hematological malignancies (D. Niewerth et al. /Biochemical Pharmacology 89 (2014) 43-51).

WO 2016/050356, WO 2016/050355, WO 2016/050359, and WO 2016/050358 describe compounds, which inhibit the activity of the immunoproteasome (LMP7) and provide a significant split to the inhibitory activity of the constitutive proteasome.

Surprisingly it was found that the amino boronic acid derivatives of the present invention provide a particularly high split to the inhibitory activity of the constitutive proteasome. In addition, they show good results in view of plasma-protein binding, CYP inhibition, PK profile and oral bioavailability.

DESCRIPTION OF THE INVENTION

The present invention provides compounds of formula (I)

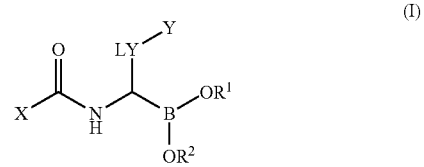

wherein (I)
LY denotes $(CH_2)_m$, wherein 1 to 4H atoms may be replaced by Hal, $R^{3a}$ and/or $OR^{4a}$, and/or wherein one $CH_2$ group may be replaced by O, S, SO or $SO_2$;
X denotes a heterobicycle or heterotricycle of formula (xa), (xb), (xc), (xd), (xe), (xf), (xg), (xh) or (xi) each, independently from one another, unsubstituted or mono-, di- or trisubstituted by Hal, $NO_2$, CN, $R^{5a}$, $OR^{5a}$, $CONR^{5a}R^{5b}$, $NR^{5a}COR^{5b}$, $SO_2R^{5a}$, $SOR^{5a}$, $SO_2NR^{5a}R^{5b}$, $NR^{5a}SO_2R^{5b}$, $NR^{5a}R^{5b}$, $(CH_2)_q$—$R^6$, $COR^{5a}$ and/or $SO_2R^{5a}$, and wherein 1, 2 or 3 of the cyclic $CH_2$ groups may be replaced $CR^{4a}R^{4b}$, C=O, O, S, $NR^{5a}$, SO and/or $SO_2$;

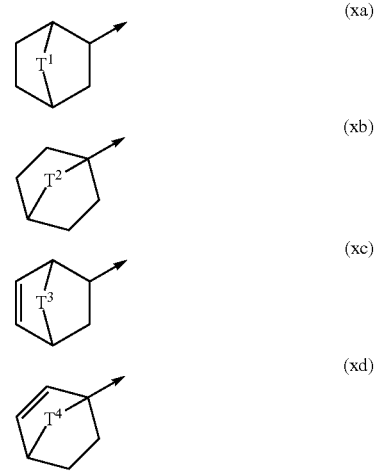

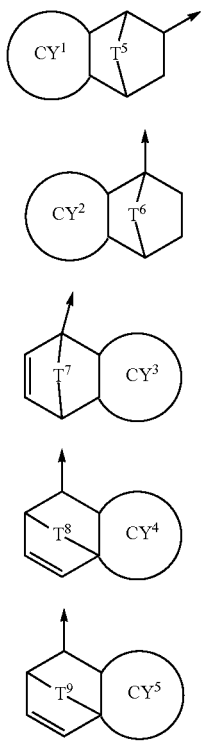

(xe)

(xf)

(xg)

(xh)

(xi)

(optional substituents of (xa)-(xi) not shown)

Y denotes P¹, P² or P³;

P¹ denotes a linear or branched $C_1$-$C_6$-alkyl or $C_3$-$C_3$-cycloalkyl, each, independently from one another, unsubstituted or mono-, di-, tri- or tetrasubstituted by Hal, CN, $R^{3a}$, $OR^{3a}$, and/or $(CH_2)_q$—$R^6$;

P² denotes phenyl or an aromatic monocyclic 5-, 6- or 7-membered heterocycle, each unsubstituted or mono-, di-, tri-, tetra- or pentasubstituted by Hal, CN, $R^{3a}$, OH, $OR^{3a}$, $CONR^{4a}R^{4b}$, $NR^{3a}COR^{3b}$, $SO_2R^{3a}$, $SOR^{3a}$, $NR^{4a}R^{4b}$, $Ar^2$, $Het^2$, $(CH_2)_q$—$SR^{3a}$, $(CH_2)_q$—$N(R^{4a})_2$ and/or $(CH_2)_q$—$R^6$, wherein the heterocyclic system contains 1, 2 or 3 N, O and/or S atoms;

P³ denotes a bicyclic 8-, 9- or 10-membered hydrocarbon or heterocycle, each independently from one another unsubstituted or mono-, di-, tri-, tetra- or pentasubstituted by Hal, CN, $R^{3a}$, OH, $OR^{3a}$, $CONR^{4a}R^{4b}$, $NR^{3a}COR^{3b}$, $SO_2R^{3a}$, $SOR^{3a}$, $NR^{4a}R^{4b}$, $Ar^2$, $Het^2$, $(CH_2)_q$—$SR^{3a}$, $(CH_2)_q$—$N(R^{4a})_2$ and/or $(CH_2)_q$—$R^6$, wherein at least one ring of the bicyclic hydrocarbon or heterocycle is aromatic, and wherein the heterocyclic system contains 1, 2 or 3 N, O and/or S atoms;

$Cy^1$, $Cy^2$, $Cy^3$, $Cy^4$ and $Cy^5$ denote each, independently from one another, $Ar^1$ or $Het^1$;

$R^1$, $R^2$ denote each, independently from one another, H or $C_1$-$C_6$-alkyl, or $R^1$ and $R^2$ form together a residue according to formula (CE)

(CE)

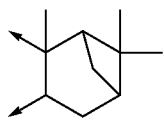

$R^{3a}$, $R^{3b}$ denote each, independently from one another, linear or branched $C_1$-$C_6$-alkyl or $C_3$-$C_8$ cycloalkyl, wherein 1 to 5H atoms may be replaced by Hal, CN, OH and/or OAlk;

$R^{4a}$, Rob denote each, independently from one another, H or $R^{3a}$; or $R^{4a}$ and $R^{4b}$ form together a $C_3$-$C_8$ alkylene group;

$R^{5a}$, $R^{5b}$ denote each, independently from one another, H, $R^{3a}$, $Ar^2$ or $Het^2$;

$R^6$ denotes OH or $OR^{3a}$;

$T^1$, $T^2$, $T^3$, $T^4$, $T^5$, $T^6$, $T^7$, $T^8$ and $T^9$ denote each, independently from one another, O, SO, C=O;

Alk denotes linear or branched $C_1$-$C_6$-alkyl;

$Ar^1$ represents an aromatic 6-membered carbocycle;

$Het^1$ represents a saturated, unsaturated or aromatic 5- or 6-membered heterocycle having 1 to 4 N, O and/or S atoms;

$Ar^2$ denotes phenyl, which is unsubstituted or mono- or disubstituted by Hal, $NO_2$, CN, $R^{3a}$, $OR^{3a}$, $CONHR^{3a}$, $NR^{3a}COR^{3b}$, $SO_2R^{3a}$, $SOR^{3a}$, $NH_2$, $NHR^{3a}$, $N(R^{3a})_2$ and/or $(CH_2)_q$—$R^6$;

$Het^2$ denotes a saturated, unsaturated or aromatic 5- or 6-membered heterocycle having 1 to 4 N, O and/or S atoms, which is unsubstituted or mono- or disubstituted by Hal, $NO_2$, CN, $R^{3a}$, OH, $OR^{3a}$, $CONHR^{3a}$, $NR^{3a}COR^{3b}$, $SO_2R^{3a}$, $SOR^{3a}$, $NH_2$, $NHR^{3a}$, $N(R^{3a})_2$, $(CH_2)_q$—$R^6$ and/or oxo (=O);

q denotes 1, 2, 3, 4, 5 or 6;

m denotes 0, 1 or 2;

Hal denotes F, Cl, Br or I;

and prodrugs, solvates, tautomers, oligomers, adducts and stereoisomers thereof as well as the pharmaceutically acceptable salts of each of the foregoing, including mixtures thereof in all ratios.

Compounds of the present invention are inhibitors of the immunoproteasome subunit LMP7. They show a particularly high selectivity on LMP7 over Beta5 (cP) and good properties in terms of solubility, plasma-protein binding, CYP inhibition, PK profile and oral bioavailabiliy.

It is known that boronic acid derivatives such as compounds of formula (I), wherein $R^1$ and $R^2$ denote H form oligomeres (Boronic Acids. Edited by Dennis G. Hall, Copyright (c) 2005 WILEY-VCH Verlag, GmbH & Co. KGaA, Weinheim, ISBN 3-527-30991-8). Such oligomeres (in particular but not limited to dimers or trimers) of compounds of formula (I) are included within this invention. Known cyclic trimers of boronic acids have for example following structure:

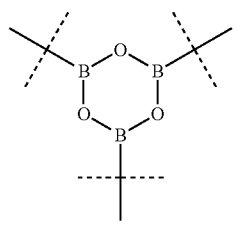

It is also known that boronic acid derivatives such as compounds of formula (I), wherein $R^1$ and $R^2$ denote H form adducts by reaction with aliphatic or aromatic alcohols, diols, sugars, sugar alcohols, α-hydroxy acids or nucleophiles containing one, two or three N-/O-containing functional group (e.g. —$NH_2$, —$CONH_2$ or C=NH, —OH, —COOH) wherein in case that three functional groups are present, one of the three heteroatoms might form a coordinative bond ("Boronic Acids" Edited by Dennis G. Hall, 2$^{nd}$ Edition, Copyright (c) 2011 WILEY-VCH Verlag, GmbH & Co. KGaA, Weinheim, ISBN 978-3-527-32598-6; WO2013128419; WO2009154737). The adduct formation is particularly fast with preorganized diols. The present invention includes such adducts (in particular esters or heterocyclic derivatives) of boronic acid compounds of formula (I).

It is to be noted that the compounds of the present invention bear a stereogenic center at the carbon atom adjacent to the boronic acid residue; it has been denoted with an asterix (*) in formula (I)* below:

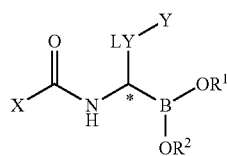

(I)*

The compounds according to formula (I) thus exhibit two different configurations at this stereogenic center, i.e. the (R)-configuration and the (S)-configuration. Hence, the compounds of the present invention may be present either enantiopure or as a racemic (1:1) mixture of the two enantiomers of formula (R)-(I) and (S)-(I).

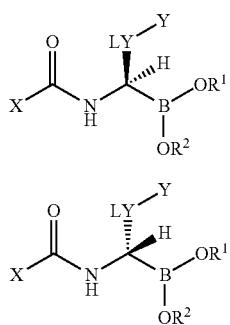

R-(I)

S-(I)

Compounds of formula (I) may also be present in a mixture in which one of the enantiomers (R)-(I) or (S)-(I) is present in an excess over the other one, e.g. 60:40, 70:30, 80:20, 90:10, 95:5 or the like. In a particular embodiment of the present invention the stereoisomer of formula (R)-(I) of the compound of formula (Ia) and the stereoisomer of formula (S)-(I) of the compound of formula (Ia) are present in a ratio of (R)-(I) to (S)-(I) of at least 90 parts of (R)-(I) to not more than 10 parts of (S)-(I), preferably of at least 95 (R)-(I) to not more than 5 (S)-(I), more preferably of at least 99 (R)-(I) to not more than 1 (S)-(I), even more preferably of at least 99.5 (R)-(I) to not more than 0.5 (S)-(I). In another particular embodiment of the present invention the stereoisomer of formula (S)-(I) of the compound of formula (Ia) and the stereoisomer of formula (R)-(I) of the compound of formula (Ia) are present in a ratio of (S)-(I) to (R)-(I) of at least 90 (S)-(I) to not more than 10 (R)-(I), preferably of at least 95 (S)-(I) to not more than 5 (R)-(I), more preferably of at least 99 (S)-(I) to not more than 1 (R)-(I), even more preferably of at least 99.5 (S)-(I) to not more than 0.5 (R)-(I).

Enriched or pure stereoisomers of formulas (R)-(I) and (S)-(I) can be obtained by usual methods known in the art and the specific methods described hereinafter. A particular method for obtaining them is preparative column chromatography, such as HPLC or SFC, using chiral column material.

Particular preferred embodiments of the present invention comprise compounds of formula (R)-(I), wherein the stereogenic center at the carbon atom adjacent to the boronic acid residue has an (R)-configuration:

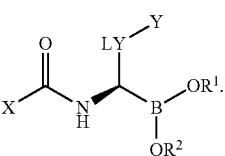

(R)-(I)

The compounds according to formula (I) might also carry further stereogenic centers located at carbon atoms other than the carbon atom adjacent to the boronic acid residue. All of these stereogenic centers may occur in (R)- or (S)-configuration.

In particular, the compounds of the present invention bear further stereogenic centers at the carbon atom of substituent X, which is directly attached to the carbon atom of the amide group CONH shown in formula (I)) and at the carbon atoms adjacent to the bridge atom; these stereogenic centers are for example shown in formula (xa*) below, wherein they are denoted with an asterix (*):

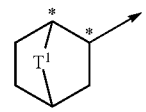

(xa*)

(optional substitutents of (xa*) not shown)
The possible stereoisomers of (xa*) are shown below:

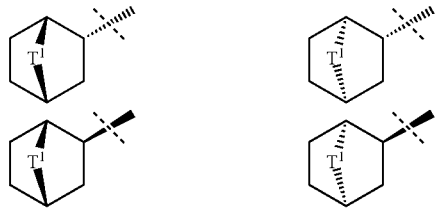

The compounds according to formula (I) thus also exhibit two different configurations at these stereogenic centers, i.e. the (R)-configuration and the (S)-configuration. The compounds of the present invention may have either an (R)-configuration or (S)-configuration at each of these stereogenic centers or the compounds are present in a racemic (1:1) mixture of two stereoisomers. The compounds of formula (I) may also be present in a mixture in which one of the stereoisomers is present in an excess over the other one, e.g. 60:40, 70:30, 80:20, 90:10, 95:5 or the like.

Above and below, in those cases, where a chemical structure with a stereogenic center is shown and no specific stereochemistry is indicated, the structure includes all possible stereoisomers as well as mixtures thereof. For example, the present invention includes the stereoisomers [(1R)-2-

[(3S)-2,3-dihydro-1-benzofuran-3-yl]-1-{[(1S,2R,4R)-7-oxabicyclo[2.2.1]-heptan-2-yl]-formamido}ethyl]boronic acid, [(1R)-2-[(3S)-2,3-dihydro-1-benzofuran-3-yl]-1-{[(1R,2S,4S)-7-oxabicyclo[2.2.1]heptan-2-yl] formamido}ethyl]boronic acid, [(1R)-2-[(3S)-2,3-dihydro-1-benzofuran-3-yl]-1-{[(1S,2S,4R)-7-oxabicyclo[2.2.1] heptan-2-yl]formamido}ethyl]boronic acid, [(1R)-2-[(3S)-2,3-dihydro-1-benzofuran-3-yl]-1-{[(1R,2R,4S)-7-oxabicyclo[2.2.1]heptan-2-yl]formamido}ethyl]boronic acid, [(1S)-2-[(3S)-2,3-dihydro-1-benzofuran-3-yl]-1-{[(1S,2S,4R)-7-oxabicyclo[2.2.1]heptan-2-yl]formamido}ethyl]-boronic acid, [(1S)-2-[(3S)-2,3-dihydro-1-benzofuran-3-yl]-1-{[(1R,2R,4S)-7-oxabicyclo[2.2.1]heptan-2-yl] formamido}ethyl]-boronic acid, [(1R)-2-[(3R)-2,3-dihydro-1-benzofuran-3-yl]-1-{[(1S,2S,4R)-7-oxabicyclo[2.2.1] heptan-2-yl]formamido}ethyl]boronic acid, [(1R)-2-[(3R)-2,3-dihydro-1-benzofuran-3-yl]-1-{[(1R,2R,4S)-7-oxabicyclo[2.2.1]heptan-2-yl]formamido}ethyl]boronic acid, [(1S)-2-[(3R)-2,3-dihydro-1-benzofuran-3-yl]-1-{[(1S,2S,4R)-7-oxabicyclo[2.2.1]heptan-2-yl]formamido}ethyl]-boronic acid, [(1S)-2-[(3R)-2,3-dihydro-1-benzofuran-3-yl]-1-{[(1R,2R,4S)-7-oxabicyclo[2.2.1]heptan-2-yl] formamido}ethyl]boronic acid, [(1S)-2-[(3S) 2,3-dihydro-1-benzofuran-3-yl]-1-{[(1S,2R,4R)-7-oxabicyclo[2.2.1]-heptan-2-yl]formamido}ethyl]boronic acid, [(1S)-2-[(3S)-2,3-dihydro-1-benzofuran-3-yl]-1-{[(1R,2S,4S)-7-oxabicyclo[2.2.1]heptan-2-yl]formamido}ethyl]-boronic acid, [(1R)-2-[(3R)-2,3-dihydro-1-benzofuran-3-yl]-1-{[(1S,2R,4R)-7-oxabicyclo[2.2.1]heptan-2-yl]formamido}ethyl]boronic acid, [(1R)-2-[(3R) 2,3-dihydro-1-benzofuran-3-yl]-1-{[(1R,2S,4S)-7-oxabicyclo[2.2.1]heptan-2-yl] formamido}ethyl]boronic acid, [(1S)-2-[(3R)-2,3-dihydro-1-benzofuran-3-yl]-1-{[(1S,2R,4R)-7-oxabicyclo[2.2.1] heptan-2-yl]formamido}ethyl]-boronic acid as well as [(1S)-2-[(3R)-2,3-dihydro-1-benzofuran-3-yl]-1-{[(1R,2S, 4S)-7-oxabicyclo[2.2.1]heptan-2-yl]formamido}ethyl]-boronic acid. Another exemplary set of stereoisomers, which are included in the present invention is represented by following stereoisomers [(1R)-2-(1-benzofuran-3-yl)-1-{[(1S,2R,4R)-7-oxabicyclo[2.2.1]heptan-2-yl] formamido}ethyl]boronic acid, [(1S)-2-(1-benzofuran-3-yl)-1-{[(1S,2R,4R)-7-oxabicyclo[2.2.1]heptan-2-yl] formamido}ethyl]boronic acid, [(1R)-2-(1-benzofuran-3-yl)-1-{[(1R,2S,4S)-7-oxabicyclo[2.2.1]heptan-2-yl] formamido}ethyl]boronic acid, [(1S)-2-(1-benzofuran-3-yl)-1-{[(1R,2S,4S)-7-oxabicyclo[2.2.1]heptan-2-yl] formamido}ethyl]boronic acid, [(1R)-2-(1-benzofuran-3-yl)-1-{[(1S,2S,4R)-7-oxabicyclo[2.2.1]heptan-2-yl] formamido}ethyl]boronic acid, [(1S)-2-(1-benzofuran-3-yl)-1-{[(1S,2S,4R)-7-oxabicyclo[2.2.1]heptan-2-yl] formamido}ethyl]boronic acid, [(1R)-2-(1-benzofuran-3-yl)-1-{[(1R,2R,4S)-7-oxabicyclo[2.2.1]heptan-2-yl] formamido}ethyl]boronic acid and [(1S)-2-(1-benzofuran-3-yl)-1-{[(1R,2R,4S)-7-oxabicyclo[2.2.1]heptan-2-yl] formamido}ethyl]boronic acid. The different stereoisomers of a given compound are useful for the analytical characterization of a specific sample (e.g. for quality control purposes) via NMR, HPLC, SFC or any other suitable analytical method. Thus, another aspect of the present invention relates to the use of stereoisomers of compounds according to formula (I) in analytical characterization methods.

In general, all residues of compounds described herein which occur more than once may be identical or different, i.e. are independent of one another. Above and below, the residues and parameters have the meanings indicated for formula (I), unless expressly indicated otherwise. Accordingly, the invention relates, in particular, to the compounds of formula (I) in which at least one of the said residues has one of the preferred meanings indicated below. Furthermore, all specific embodiments described below shall include derivatives, prodrugs, solvates, tautomers or stereoisomers thereof as well as the physiologically acceptable salts of each of the foregoing, including mixtures thereof in all ratios.

The heterobicycles or heterotricycles of formula (xa), (xb), (xc), (xd), (xe), (xf), (xg), (xh) and (xi) can be unsubstituted or mono-, di- or trisubstituted by Hal, $NO_2$, CN, $R^{5a}$, $OR^5$, $CONR^{5a}R^{5b}$, $NR^{5a}COR^{5b}$, $SO_2R^{5a}$, $SOR^{5a}$, $SO_2NR^{5a}R^{5b}$, $NR^{5a}SO_2R^{5b}$, $NR^{5a}R^{5b}$, $(CH_2)_q$—$R^6$, $COR^{5a}$ and/or $SO_2R^{5a}$. In case the heterobicycles or heterotricycles of formula (xe), (xf), (xg), (xh) and (xi) are substituted, the one or more substituents can be attached to the one of the bridged rings or one of the fused rings $Cy^1$, $Cy^2$, $Cy^3$, $Cy^4$ and $Cy^5$.

This includes for example compounds wherein one substituent is attached to the bridged ring and one substituent is attached to the fused ring $Cy^1$, $Cy^2$, $Cy^3$, $Cy^4$ or $Cy^5$. In case one of the fused rings $Cy^1$, $Cy^2$, $Cy^3$, $Cy^4$ and $Cy^5$ contains one or more $CH_2$ groups these groups are understood to be part of the "cyclic $CH_2$ groups" of heterobicycles or heterotricycles of formula (xe), (xf), (xg), (xh) and (xi), which may be replaced by $CR^{4a}R^{4b}$, C=O, O, S, $NR^{5a}$, SO or $SO_2$. Thus, if 1, 2 or 3 of the cyclic $CH_2$ groups of heterobicycles or heterotricycles of formula (xe), (xf), (xg), (xh) and (xi) are replaced by $CR^{4a}R^{4b}$, C=O, O, S, $NR^{5a}$, SO or $SO_2$ these cyclic $CH_2$ may be part of the bridged ring and/or the fused rings $Cy^1$, $Cy^2$, $Cy^3$, $Cy^4$ and $Cy^5$. This includes for example compounds wherein one $CH_2$ group of the bridged ring is replaced and one $CH_2$ the fused ring $Cy^1$, $Cy^2$, $Cy^3$, $Cy^4$ or $Cy^5$ is replaced.

In case Y is $P^3$, wherein at least one of the two rings of the bicyclic hydrocarbon or heterocycle is an aromatic ring, the other ring may be a saturated, unsaturated or aromatic ring. In specific examples of such embodiments $P^3$ and the adjacent group LY are attached to each other via the aromatic ring of $P^3$. In other embodiments $P^3$ and the adjacent group LY are attached to each other via the saturated or unsaturated ring of $P^3$. In case $P^3$ is a bicyclic heterocycle it preferably contains 1 or 2 heteroatoms selected from N, O and/or S. In case $P^2$ is an aromatic monocyclic heterocyle it preferably contains 1 or 2 heteroatoms selected from N, O and/or S.

In case Y is $P^2$ and $P^2$ is phenyl, it is preferably unsubstituted or mono-, di- or trisubstituted by Hal, CN, $R^{3a}$, OH, $OR^{3a}$, $CONR^{4a}R^{4b}$, $NR^{3a}COR^{3b}$, $SO_2R^{3a}$, $SOR^{3a}$, $NR^{4a}R^{4b}$, $Ar^2$, $Het^2$, $(CH_2)_q$—$SR^{3a}$, $(CH_2)_q$—$N(R^{4a})_2$ and/or $(CH_2)_q$—$R^5$. Particular preferred are embodiments wherein $P^2$ denotes a di- or trisubstituted phenyl. In those embodiments wherein $P^2$ denotes a monosubstituted phenyl, the substituent is preferably in the 3-, or the 4-position. In those embodiments wherein $P^2$ denotes a disubstituted phenyl, the two substituents are preferably in 2,3-, 2,4-, 2,5- or 3,4-position (most preferably in 2,4- or 3,4-position). And in those embodiments, wherein $P^2$ denotes a trisubstituted phenyl, the three substituents are preferably in 2,3,4-position of the aromatic ring.

In case $P^2$ denotes a monocyclic heterocycle this heterocycle can be saturated, unsaturated or aromatic.

In embodiments wherein m denotes 0, LY is absent.

In the context of the present invention "$C_1$-$C_6$-alkyl" means an alkyl moiety having 1, 2, 3, 4, 5 or 6 carbon atoms and being straight-chain or branched. The term "$C_3$-$C_6$-cycloalkyl" refers to saturated cyclic hydrocarbon groups having 3, 4, 5 or 6 carbon atoms.

The term "unsubstituted" means that the corresponding radical, group or moiety has no substituents other than H; the term "substituted", which applies to one or more hydrogens that are either explicit or implicit from the structure, means that the corresponding radical, group or moiety has one or more substituents other than H. Where a radical has a plurality of substituents, i.e. at least two, and a selection of various substituents is specified, the substituents are selected independently of one another and do not need to be identical.

The term "carbocycle" means a ring system, wherein all ring members are carbon atoms.

The term "heterocycle" means a rings system, wherein some of the ring members are heteroatoms such as N, O, or S.

The group "NRR'", is an amino group, wherein R and R' are for example each independently from one another H or linear or branched $C_1$-$C_6$-alkyl residues (particularly methyl, ethyl, propyl, isopropyl, butyl, isobutyl, sec-butyl or tert-butyl, pentyl, hexyl).

The group "SO" as e.g. included in the $SOR^{5a}$, is group, wherein S and O are connected via a double bond (S=O).

The group "CO" as e.g. included in the $COR^{4a}$, is group, wherein C and O are connected via a double bond (C=O).

The term "alkylene" refers to a divalent alkyl group. An "alkylene group" is a (poly)methylene group (—$(CH_2)_x$—).

The oxo group (=O) is a substituent, which may which may occur e.g. in saturated cyclic residues or, to the extent possible, in (partially) unsaturated ring such as in particular $Het^1$ and $Het^2$. In preferred embodiments the heterocycles $Het^1$ and $Het^2$ optionally carry one or two oxo groups.

As used herein, the term "unsaturated", means that a moiety has one or more units of unsaturation. As used herein with reference to any rings, cyclic systems, cyclic moieties, and the like, the term "partially unsaturated" refers to a cyclic moiety that includes at least one double or triple bond. The term "partially unsaturated" is intended to encompass cyclic moieties having more the one double or triple bond.

In the context of the present invention notations like "O—$CH_3$" and "$OCH_3$" or "$CH_2CH_2$" and "—$CH_2$—$CH_2$—" have the same meaning and are used interchangeably.

As used herein, in structural formulas arrows or bonds with vertical dotted lines are used to indicate the point of attachment to an adjacent group. For example, the arrow in (xa) shows the point of attachment to the adjacent C=O group.

Particular important embodiments of the present invention include compounds of formula (I), wherein
$R^1$, $R^2$ denote each, independently from one another, H or $C_1$-$C_4$-alkyl or $R^1$ and $R^2$ form together a residue according to formula (CE); and
LY denotes $CH_2$ or $CH_2CH_2$, wherein 1 to 2H atoms may be replaced by Hal, $R^{3a}$, $OR^{4a}$ (preferably 1 to 2H atoms may be replaced by F, Cl, $CH_3$, $CH_2CF_3$, $CH_2CHF_2$, $CH_2F$, $CHF_2$, $CF_3$. $OCH_3$ and/or $OCF_3$, and most preferably LY denotes $CH_2$ or $CH_2CH_2$).

Specific embodiments include compounds of formula (I), wherein $T^1$, $T^2$, $T^3$, $T^4$, $T^5$, $T^6$, $T^7$, $T^8$ and $T^9$ denote O.

Other specific embodiments comprise compounds according to formula (I), wherein
$P^1$ denotes a linear or branched $C_1$-$C_6$-alkyl or $C_3$-$C_6$-cycloalkyl, each, independently from one another, unsubstituted mono-, di- or trisubstituted by Hal, CN, $R^{3a}$, $OR^{3a}$, and/or $(CH_2)_q$—$R^6$;
$P^2$ denotes phenyl, pyridyl, pyrrolyl, furanyl, thiophenyl, pyrimidyl, pyranzinyl or pyridazinyl, each, independently from one another, unsubstituted mono-, di- or trisubstituted by Hal, CN, $R^{3a}$, OH, $OR^{3a}$, $CONR^{4a}R^{4b}$, $NR^{3a}COR^{3b}$, $SO_2R^{3a}$, $SOR^{3a}$, $NR^{4a}R^{4b}$, $Ar^2$, $Het^2$, $(CH_2)_q$—$SR^{3a}$, $(CH_2)_q$—$N(R^{4a})_2$ and/or $(CH_2)_q$—$R^6$; and
$P^3$ denotes a bicyclic residue of formula (ya), (yb), (yc), (yd), (ye), (yf), (yg), (yh), (yi), (yj), (yk), (yl), (ym), (yn), (yp) or (yp), each, independently from one another, unsubstituted mono-, di- or trisubstituted by Hal, CN, $R^{3a}$, OH, $OR^{3a}$, $CONR^{4a}R^{4b}$, $NR^{3a}COR^{3b}$, $SO_2R^{3a}$, $SOR^{3a}$, $NR^{4a}R^{4b}$, $Ar^2$, $Het^2$, $(CH_2)_q$—$SR^{3a}$, $(CH_2)_q$—$N(R^{4a})_2$ and/or $(CH_2)_q$—$R^6$:

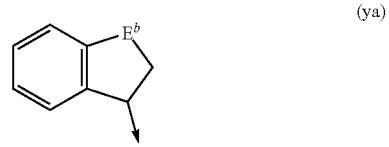

(ya)

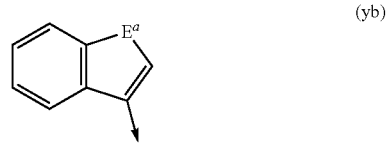

(yb)

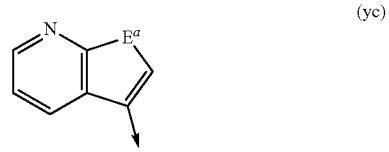

(yc)

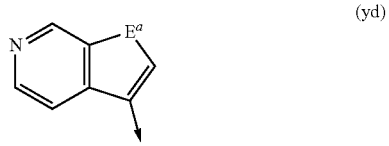

(yd)

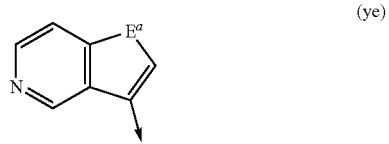

(ye)

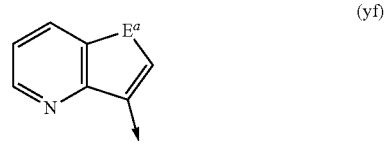

(yf)

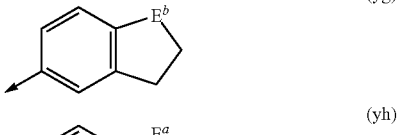

(yg)

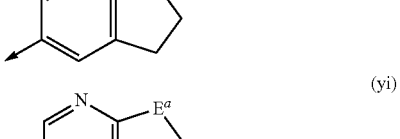

(yh)

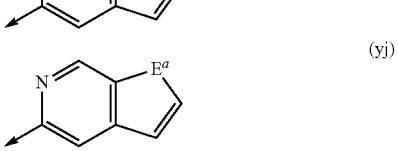

(yi)

(yj)

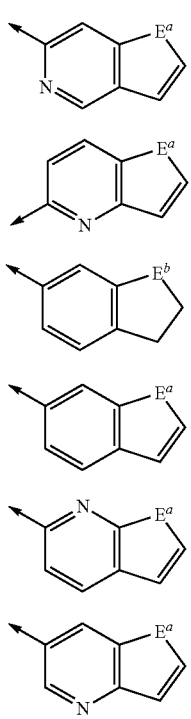

(yk)

(yl)

(ym)

(yn)

(yo)

(yp)

(optional substituents of (ya)-(yp) not shown)

wherein $E^a$ denotes O, S, N(Alk) or CH=CH;

$E^b$ denotes O, S, N(Alk), $CH_2$, $CH_2CH_2$, $OCH_2$, $SCH_2$ or N(Alk)$CH_2$.

In further embodiments of the invention the residues of a compound of formula (I) are defined as follows:

$R^{3a}$, $R^{3b}$ denote each, independently from one another, linear or branched $C_1$-$C_4$-alkyl or $C_3$-$C_6$ cycloalkyl, wherein 1 to 3H atoms may be replaced by F, Cl and/or and wherein 1 or 2H atoms may be replaced by CN, OH, $OCH_3$, and/or $OC_2H_5$.

Further embodiments of the invention comprise compounds according to formula (I) wherein Y denotes $P^2$ or $P^3$.

Other specific embodiments comprise compounds according to formula (I), wherein

X is a heterobicycle or heterotricycle of formula of formula (xa1), (xb1), (xc1), (xd1), (xe1), (xf1), (xg1), (xh1) or (xi1), each, independently from one another, unsubstituted or mono-, di- or trisubstituted by Hal, $NO_2$, CN, $R^{5a}$, $OR^{5a}$, $CONR^{5a}R^{5b}$, $NR^{5a}COR^{5b}$, $SO_2R^{5a}$, $SOR^{5a}$, $SO_2NR^{5a}R^{5b}$, $NR^{5a}SO_2R^{5b}$, $NR^{5a}R^{5b}$, $(CH_2)_q$—$R^6$, $COR^{5a}$ and/or $SO_2R^{5a}$, and wherein 1 of the cyclic $CH_2$ groups may be replaced $CR^{4a}R^{4b}$, C=O, O, S, $NR^{5a}$, SO and/or $SO_2$:

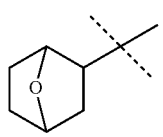

(xa1)

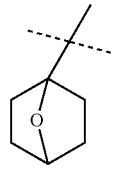

(xb1)

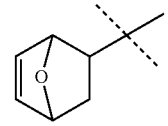

(xc1)

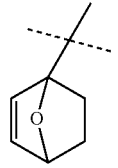

(xd1)

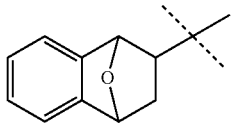

(xe1)

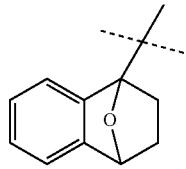

(xf1)

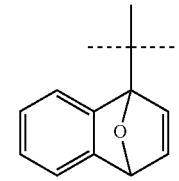

(xg1)

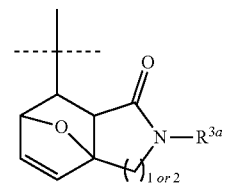

(xh1)

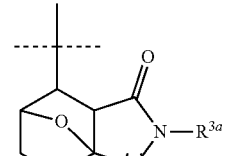

(xi1)

(optional substituents of (xa1)-(xi1) not shown)

Other specific embodiments comprise compounds according to formula (I), wherein

X is a heterobicycle or heterotricycle of formula (xa), (xb), (xc), (xd), (xe), (xf), (xg), (xh) or (xi) each, independently from one another, unsubstituted or mono- or disubstituted by F, Cl, $CH_3$, $C_2H_5$, $CF_3$, $OCH_3$, $OC_2H_5$, $COCF_3$, $SCH_3$, $SC_2H_5$, $CH_2OCH_3$. $N(CH_3)_2$, $CH_2N(CH_3)_2$ and/or $N(C_2H_5)_2$, and wherein 1 or 2 of the cyclic CH$_2$ groups may be replaced C(CH$_3$)$_2$, C(C$_2$H$_5$)$_2$, C=O, O, S, NH, NR$^{3a}$, SO and/or SO$_2$ (wherein R$^{3a}$ is preferably methyl, ethyl, propyl, isopropyl or cyclopropyl).

Important embodiments comprise compounds, of formula (I), wherein X is a heterobicycle or heterotricycle of formula (xa1), (xb1), (xc1), (xd1), (xe1), (xf1), (xg1), (xh1) or (xi1), each, independently from one another, unsubstituted or mono-, disubstituted by F, Cl, CH$_3$, C$_2$H$_5$, CF$_3$, OCH$_3$, OC$_2$H$_5$, COCF$_3$, SCH$_3$, SC$_2$H$_5$, CH$_2$OCH$_3$, N(CH$_3$)$_2$, CH$_2$N(CH$_3$)$_2$ and/or N(C$_2$H$_5$).

Very specific embodiments comprise compounds, of formula (I), wherein X is a heterobicycle or heterotricycle selected from the following group:

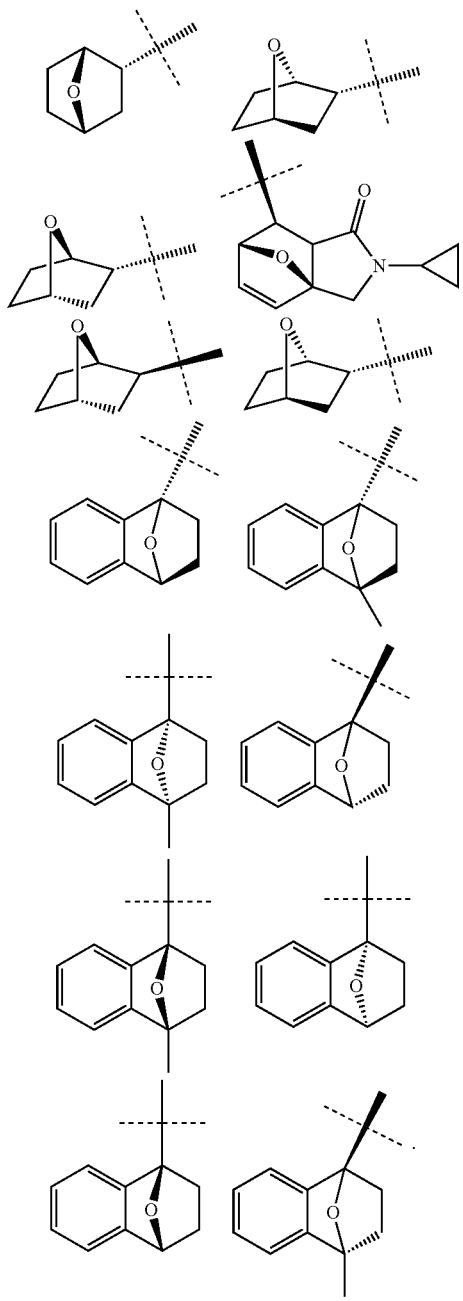

Other embodiments comprise compounds of formula (I), wherein

P$^3$ denotes unsubstituted or mono- or disubstituted 1- or 2-naphthyl, wherein the optional substituents are selected from a group consisting of Hal, CN, R$^{3a}$, OH, OR$^{3a}$, CONR$^{4a}$R$^{4b}$, NR$^{3a}$COR$^{3b}$, SO$_2$R$^{3a}$, SOR$^{3a}$, NR$^{4a}$R$^{4b}$, Ar$^2$, Het$^2$, (CH$_2$)$_q$—SR$^{3a}$, (CH$_2$)$_q$—N(R$^{4a}$)$_2$ and/or (CH$_2$)$_q$—R$^6$, or (P$^3$ is) a residue according to formula (R$^a$) or (R$^b$):

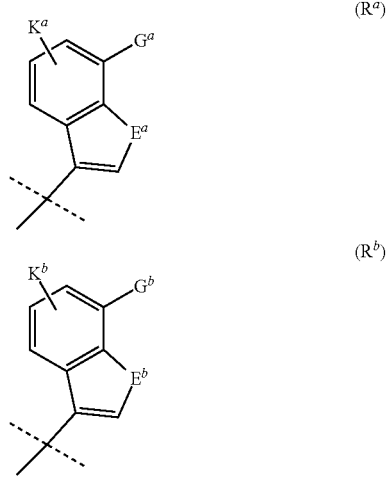

wherein

G$^a$, G$^b$ denote each, independently from one another, H, Hal, CN, R$^{3a}$, OR$^{3a}$, CONHR$^{3a}$, CONR$^{3b}$R$^{3a}$, CONH$_2$, NR$^{3a}$COR$^{3b}$, SO$_2$R$^{3a}$, SOR$^{3a}$, NHR$^{3a}$, N(R$^{3a}$)$_2$, (CH$_2$)$_q$—SR$^{3a}$, (CH$_2$)$_q$—N(R$^{4a}$)$_2$ and/or (CH$_2$)$_q$—R$^6$;

K$^a$, K$^b$ denote each, independently from one another, H, Hal, CN, R$^{3a}$, OR$^{3a}$, CONHR$^{3a}$, CONR$^{3b}$R$^{3a}$, CONH$_2$, NR$^{3a}$COR$^{3b}$, SO$_2$R$^{3a}$, SOR$^{3a}$, NHR$^{3a}$, N(R$^3$)$_2$, (CH$_2$)$_q$—SR$^{3a}$, (CH$_2$)$_q$—N(R$^{4a}$)$_2$ and/or (CH$_2$)$_q$—R$^6$;

E$^a$ denotes O, S, N(Alk) or CH=CH;

E$^b$ denotes O, S, N(Alk), CH$_2$, CH$_2$CH$_2$, O—CH$_2$, S—CH$_2$ or N(Alk)CH$_2$.

The residue according to formula (R$^b$) bears a stereogenic center at the carbon atom next to LY; it has been denoted with an asterix (*) in formula (R$^b$)* below:

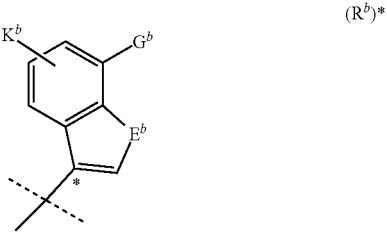

The residues according to formula (R$^b$) thus exhibit two different configurations at this stereogenic center, i.e. the (R)-configuration and the (S)-configuration. Hence, the compounds of the present invention may be present either enantiopure or as a racemic (1:1) mixture of the two enantiomers of formula (R)—(R$^b$) and (S)—(R$^b$).

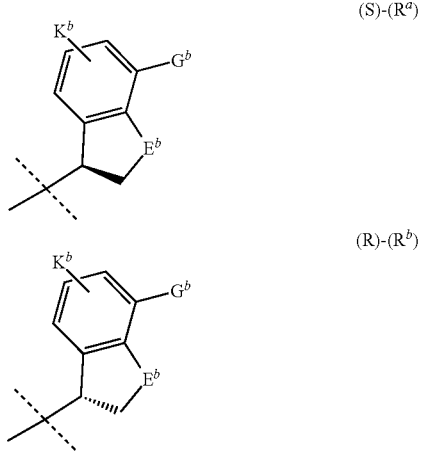

(S)-(R$^a$)

(R)-(R$^b$)

Compounds of formula (I) which include residues according to formula (R$^b$) may also be present in a mixture in which one of the enantiomers (R)—(R$^b$) or (S)—(R$^b$) is present in an excess over the other one, e.g. 60:40, 70:30, 80:20, 90:10, 95:5 or the like. In a particular embodiment of the present invention the stereoisomer of formula (R)—(R$^b$) of the compound of formula (I) and the stereoisomer of formula (S)—(R$^b$) of the compound of formula (I) are present in a ratio of (R)—(R$^b$) to (S)—(R$^b$) of at least 90 parts of (R)—(R$^b$) to not more than 10 parts of (S)—(R$^b$), preferably of at least 95 (R)—(R$^b$) to not more than 5 (S)—(R$^b$), more preferably of at least 99 (R)—(R$^b$) to not more than 1 (S)—(R$^b$), even more preferably of at least 99.5 (R)—(R$^b$) to not more than 0.5 (S)—(R$^b$). In another particular embodiment of the present invention the stereoisomer of formula (S)—(R$^b$) of the compound of formula (R$^b$) and the stereoisomer of formula (R)—(R$^b$) of the compound of formula (I) are present in a ratio of (S)—(R$^b$) to (R)—(R$^b$) of at least 90 (S)—(R$^b$) to not more than 10 (R)—(R$^b$), preferably of at least 95 (S)—(R$^b$) to not more than 5 (R)—(R$^b$), more preferably of at least 99 (S)—(R$^b$) to not more than 1 (R)—(R$^b$), even more preferably of at least 99.5 (S)—(R$^b$) to not more than 0.5 (R)—(R$^b$).

Particular preferred embodiments of the present invention comprise compounds of formula (I), wherein P$^3$ is a residue of formula (S)—(R$^b$) (which has an (S)-configuration at the carbon attached to LY).

Specific embodiments comprise compounds according to formula (I), wherein:
P$^2$ denotes unsubstituted or mono- or disubstituted 2- or 3-thienyl or unsubstituted or 3-, 4-, 2,3-, 2,4-, 2,5-, 3,4- or 2,3,4-substituted phenyl, wherein in each case the optional substituents are independently selected from a group consisting of Hal, CN, R$^{3a}$, OH, OR$^{3a}$, CONR$^{4a}$R$^{4b}$, NR$^{3a}$COR$^{3b}$, SO$_2$R$^{3a}$, SOR$^{3a}$, NR$^{4a}$R$^{4b}$, Ar$^2$, Het$^2$, (CH$_2$)$_q$—SR$^{3a}$, (CH$_2$)$_q$—N(R$^{4a}$)$_2$ and (CH$_2$)$_q$—R$^6$;
P$^3$ denotes unsubstituted or mono- or disubstituted 1- or 2-naphthyl, wherein the optional substituents are selected from a group consisting of Hal, CN, R$^{3a}$, OH, OR$^{3a}$, CONR$^{4a}$R$^{4b}$, NR$^{3a}$COR$^{3b}$, SO$_2$R$^{3a}$, SOR$^{3a}$, NR$^{4a}$R$^{4b}$, Ar$^2$, Het$^2$, (CH$_2$)$_q$—SR$^{3a}$, (CH$_2$)$_q$—N(R$^{4a}$)$_2$ and/or (CH$_2$)$_q$—R$^6$,
or
(P$^3$ is) a residue according to formula (R$^a$) or (R$^b$) (preferably P$^3$ is a residue according to formula (R$^a$) or (S)—(R$^b$));

G$^a$, G$^b$ denote each, independently from one another, H, Hal, CN, R$^{3a}$, OR$^{3a}$, CONHR$^{3a}$, CONR$^{3b}$R$^{3a}$, CONH$_2$, NR$^{3a}$COR$^{3b}$, SO$_2$R$^{3a}$, SOR$^{3a}$, NHR$^{3a}$, N(R$^{3a}$)$_2$, (CH$_2$)$_q$—SR$^{3a}$, (CH$_2$)$_q$—N(R$^{4a}$)$_2$ and/or (CH$_2$)$_q$—R$^6$;
K$^a$, K$^b$ denote each, independently from one another, H, Hal, CN, R$^{3a}$, OR$^{3a}$, CONHR$^{3a}$, CONR$^{3b}$R$^{3a}$, CONH$_2$, NR$^{3a}$COR$^{3b}$, SO$_2$R$^{3a}$, SOR$^{3a}$, NHR$^{3a}$, N(R$^{3a}$)$_2$, (CH$_2$)$_q$—SR$^{3a}$, (CH$_2$)$_q$—N(R$^{4a}$)$_2$ and/or (CH$_2$)$_q$—R$^6$;
E$^a$ denotes O, S, N(Alk) or CH=CH;
E$^b$ denotes O, S, N(Alk), CH$_2$, CH$_2$—CH$_2$, OCH$_2$, SCH$_2$ or N(Alk)CH$_2$.

Further specific embodiments comprise compounds of formula (I), wherein:
P$^2$ denotes unsubstituted or mono- or disubstituted 2- or 3-thienyl or unsubstituted or 3-, 4-, 2,3-, 2,4-, 2,5-, 3,4- or 2,3,4-substituted phenyl, wherein in each case the optional substituents are independently selected from a group consisting of Hal, CN, R$^{7a}$, OR$^{7a}$, CONHR$^{7a}$, CONR$^{7b}$R$^{7a}$, CONH$_2$, NR$^{7a}$COR$^{7b}$, SO$_2$R$^{7a}$, SOR$^{7a}$, NHR$^{7a}$, N(R$^{7a}$)$_2$, (CH$_2$)$_p$—SR$^{7a}$, (CH$_2$)$_p$—N(R$^{7a}$)$_2$ and/or (CH$_2$)$_p$—R$^8$;
P$^3$ is a residue according to formula (Re) or (R$^b$) (preferably P$^3$ is a residue according to formula (Re) or (S)—(R$^b$));
G$^a$, G$^b$ denote each, independently from one another, H, Hal, CN, R$^{7a}$, OR$^{78}$, CONHR$^{7a}$, CONR$^{7b}$R$^{7a}$, CONH$_2$, NR$^{7a}$COR$^{7b}$, SO$_2$R$^{7a}$, SOR$^{7a}$, NHR$^{7a}$, N(R$^{7a}$)$_2$, (CH$_2$)$_p$—SR$^{7a}$, (CH$_2$)$_p$—N(R$^{7a}$)$_2$ and/or (CH$_2$)$_p$—R$^8$;
K$^a$, K$^b$ denote each, independently from one another, H, Hal, CN, R$^{7a}$, OR$^{7a}$, CONHR$^{7a}$, CONR$^{7b}$R$^{7a}$, CONH$_2$, NR$^{7a}$COR$^{7b}$, SO$_2$R$^{7a}$, SOR$^{7a}$, NHR$^{7a}$, N(R$^{7a}$)$_2$, (CH$_2$)$_p$—SR$^{7a}$, (CH$_2$)$_p$—N(R$^{7a}$)$_2$ and/or (CH$_2$)$_p$—R$^8$;
R$^{7a}$, R$^{7b}$ denote each, independently from one another, linear or branched C$_1$-C$_3$-alkyl, wherein 1 to 3H atoms may be replaced by Hal; and
R$^8$ denotes OH or OR$^{7a}$; and
p denotes 1 or 2.

Even more specific embodiments comprise compounds according to formula (I), wherein:
P$^2$ denotes unsubstituted or mono- or disubstituted 2- or 3-thienyl or unsubstituted or 3-, 4-, 2,3-, 2,4-, 2,5-, 3,4- or 2,3,4-substituted phenyl, wherein the optinal substituents are selected from a group consisting of F, Cl, CN, CH$_3$, C$_2$H$_5$, CF$_3$, OCH$_3$, OC$_2$H$_5$, COCF$_3$, SCH$_3$, SC$_2$H$_5$, CH$_2$OCH$_3$, N(CH$_3$)$_2$, CH$_2$N(CH$_3$)$_2$ or N(C$_2$H$_5$)$_2$;
P$^3$ is a residue according to formula (R$^a$) or (R$^b$) (preferably P$^3$ is a residue according to formula (R$^a$) or (S)—(R$^b$));
G$^a$, G$^b$ denote each, independently from one another, H, F, Cl, CN, CH$_3$, C$_2$H$_5$, CF$_3$, OCH$_3$, OC$_2$H$_5$, COCF$_3$, SCH$_3$, SC$_2$H$_5$, CH$_2$OCH$_3$, N(CH$_3$)$_2$, CH$_2$N(CH$_3$)$_2$ or N(C$_2$H$_5$)$_2$;
K$^a$, K$^b$ denote each, independently from one another, H, F, Cl, CN, CH$_3$, C$_2$H$_5$, CF$_3$, OCH$_3$, OC$_2$H$_5$, COCF$_3$, SCH$_3$, SC$_2$H$_5$, CH$_2$OCH$_3$, N(CH$_3$)$_2$, CH$_2$N(CH$_3$)$_2$ or N(C$_2$H$_5$)$_2$.

Particular embodiments comprise compounds of formula (I), wherein P$^3$ is a residue according to formula (R$^a$) or (R$^b$), and wherein E$^a$, E$^b$ denote each, independently from one another, O or S. Particular preferred embodiments comprise compounds of formula (I), wherein P$^3$ is a residue according to formula (F$^a$) or (F$^b$):

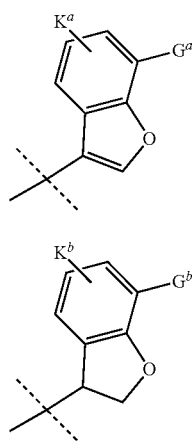

In such embodiments, the stereogenic center at the carbon atom in position 3 of the dihydrofuranyl residue ($F^b$) shows preferably an (S)-configuration, i.e. the residue is an (optionally substituted) (3S)-2,3-dihydrobenzofuran-3-yl residue (S)—($F^b$)*:

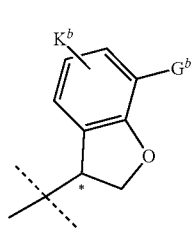

(optional substituents not shown).

Thus, further very specific embodiments of the invention the present invention comprise compounds according to formula (I), wherein
- $P^2$ denotes unsubstituted or mono- or disubstituted 2- or 3-thienyl or unsubstituted or 3-, 4-, 2,3-, 2,4-, 2,5-, 3,4- or 2,3,4-substituted phenyl, wherein the optinal substituents are selected from a group consisting of Hal, CN, $R^{3a}$, OH, $OR^{3a}$, $CONR^{4a}R^{4b}$, $NR^{3a}COR^{3b}$, $SO_2R^{3a}$, $SOR^{3a}$, $NR^{4a}R^{4b}$, $Ar^2$, $Het^2$, $(CH_2)_q$—$SR^{3a}$, $(CH_2)_q$—$N(R^{4a})_2$ and/or $(CH_2)_q$—$R^6$;
- $P^3$ denotes a residue according to formula ($F^a$) or (S)—($F^b$);
- $G^a$, $G^b$ denote each, independently from one another, H, Hal, CN, $R^{3a}$, OH, $OR^{3a}$, $CONR^{4a}R^{4b}$, $NR^{3a}COR^{3b}$, $SO_2R^{3a}$, $SOR^{3a}$, $NR^{4a}R^{4b}$, $Ar^2$, $Het^2$, $(CH_2)_q$—$SR^{3a}$, $(CH_2)_q$—$N(R^{4a})_2$ and/or $(CH_2)_q$—$R^6$; and
- $K^a$, $K^b$ denote each, independently from one another, H, Hal, CN, $R^{3a}$, OH, $OR^{3a}$, $CONR^{4a}R^{4b}$, $NR^{3a}COR^{3b}$, $SO_2R^{3a}$, $SOR^{3a}$, $NR^{4a}R^{4b}$, $Ar^2$, $Het^2$, $(CH_2)_q$—$SR^{3a}$, $(CH_2)_q$—$N(R^{4a})_2$ and/or $(CH_2)_q$—$R^6$.

Other very specific embodiments of the invention the present invention comprise compounds according to formula (I), wherein:
- $P^2$ denotes unsubstituted or mono- or disubstituted 2- or 3-thienyl or unsubstituted or 3-, 4-, 2,3-, 2,4-, 2,5-, 3,4- or 2,3,4-substituted phenyl, wherein the optinal substituents are selected from a group consisting of H, Hal, CN, $R^{7a}$, $OR^{7a}$, $CONHR^{7a}$, $CONR^{7b}R^{7a}$, $CONH_2$, $NR^{7a}COR^{7b}$, $SO_2R^{7a}$, $SOR^{7a}$, $NHR^{7a}$, $N(R^{7a})_2$, $(CH_2)_p$—$SR^{7a}$, $(CH_2)_p$—$N(R^{7a})_2$ and/or $(CH_2)_p$—$R^8$;
- $P^3$ denotes a residue according to formula ($F^a$) or (S)—($F^b$);

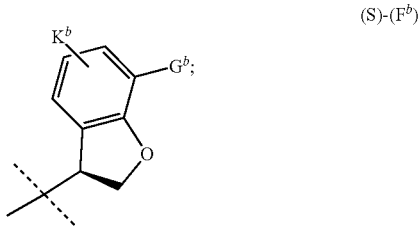

- $G^a$, $G^b$ denote each, independently from one another, H, Hal, CN, $R^{7a}$, $OR^{7a}$, $CONHR^{7a}$, $CONR^{7b}R^{7a}$, $CONH_2$, $NR^{7a}COR^{7b}$, $SO_2R^{7a}$, $SOR^{7a}$, $NHR^{7a}$, $N(R^{7a})_2$, $(CH_2)_p$—$SR^{7a}$, $(CH_2)_p$—$N(R^{7a})_2$ and/or $(CH_2)_p$—$R^8$;
- $K^a$, $K^b$ denote each, independently from one another, H, Hal, CN, $R^{7a}$, $OR^{7a}$, $CONHR^{7a}$, $CONR^{7b}R^{7a}$, $CONH_2$, $NR^{7a}COR^{7b}$, $SO_2R^{7a}$, $SOR^{7a}$, $NHR^{7a}$, $N(R^{7a})_2$, $(CH_2)_p$—$SR^{7a}$, $(CH_2)_p$—$N(R^{7a})_2$ and/or $(CH_2)_p$—$R^8$;
- $R^{7a}$, $R^{7b}$ denote each, independently from one another, linear or branched $C_1$-$C_3$-alkyl, wherein 1 to 3H atoms may be replaced by Hal; and
- $R^8$ denotes OH or $OR^{7a}$; and
- p denotes 1 or 2.

Other very specific embodiments of the present invention comprise compounds according to formula (I), wherein:
- $P^2$ denotes unsubstituted or mono- or disubstituted 2- or 3-thienyl or unsubstituted or 3-, 4-, 2,3-, 2,4-, 2,5-, 3,4- or 2,3,4-substituted phenyl, wherein the optional substituents are selected from a group consisting of F, Cl, CN, $CH_3$, $C_2H_5$, $CF_3$, $OCH_3$, $OC_2H_5$, $COCF_3$, $SCH_3$, $SC_2H_5$, $CH_2OCH_3$, $N(CH_3)_2$, $CH_2N(CH_3)_2$ or $N(C_2H_5)_2$;
- $P^3$ denotes a residue according to formula (P) or (S)—($F^b$),
- $G^a$, $G^b$ denote each, independently from one another, H, F, Cl, CN, $CH_3$, $C_2H_5$, $CF_3$, $OCH_3$, $OC_2H_5$, $COCF_3$, $SCH_3$, $SC_2H_5$, $CH_2OCH_3$, $N(CH_3)_2$, $CH_2N(CH_3)_2$ or $N(C_2H_5)_2$; and
- $K^a$, $K^b$ denote each, independently from one another, H, F, Cl, CN, $CH_3$, $C_2H_5$, $CF_3$, $OCH_3$, $OC_2H_5$, $COCF_3$, $SCH_3$, $SC_2H_5$, $CH_2OCH_3$, $N(CH_3)_2$, $CH_2N(CH_3)_2$ or $N(C_2H_5)_2$.

Particular embodiments of the present invention comprise compounds according to formula (I), wherein Y denotes $P^2$ or $P^3$, preferably Y denotes $P^3$.

Specific embodiments of the present invention comprise compounds according to formula (I) wherein
- LY denotes $CH_2$ or $CH_2CH_2$, wherein 1 to 2H atoms may be replaced by Hal, $R^{7a}$, OH and/or $OR^{7a}$, and/or wherein one $CH_2$ group may be replaced by O or S;
- X is a heterobicycle or heterotricycle of formula (xa), (xb), (xc), (xd), (xe), (xf), (xg), (xh) or (xi) each, independently from one another, unsubstituted or mono- or disubstituted by F, Cl, $CH_3$, $C_2H_5$, $CF_3$, $OCH_3$, $OC_2H_5$, $COCF_3$, $SCH_3$, $SC_2H_5$, $CH_2OCH_3$, $N(CH_3)_2$, $CH_2N(CH_3)_2$ and/or $N(C_2H_5)_2$, and wherein 1 of the cyclic $CH_2$ groups may be replaced $C(CH_3)_2$, $C(C_2H_5)_2$, C=O, O, S, $NCH_3$, SO or $SO_2$;
- Y denotes $P^2$ or $P^3$ (preferably $P^3$);

P² denotes unsubstituted or mono- or disubstituted 2- or 3-thienyl or unsubstituted or 3-, 4-, 2,3-, 2,4-, 2,5-, 3,4- or 2,3,4-substituted phenyl, wherein the optimal substituents are selected from a group consisting of H, Hal, CN, $R^{7a}$, $OR^{7a}$, $CONHR^{7a}$, $CONR^{7b}R^{7a}$, $CONH_2$, $NR^{7a}CORT$, $SO_2R^{7a}$, $SOR^{7a}$, $NHR^{7a}$, $N(R^{7a})_2$, $(CH_2)_p-SR^{7a}$, $(CH_2)_p-N(R^{7a})_2$ and/or $(CH_2)_p-R^8$;

P³ denotes a residue according to formula (F$^a$) or (S)—(F$^b$);

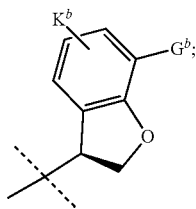
(S)-(F$^b$)

G$^a$, G$^b$ denote each, independently from one another, H, Hal, CN, $R^{7a}$, $OR^{7a}$, $CONHR^{7a}$, $CONR^{7b}R^{7a}$, $CONH_2$, $NR^{7a}COR^{7b}$, $SO_2R^{7a}$, $SOR^{7a}$, $NHR^{7a}$, $N(R^{7a})_2$, $(CH_2)_p-SR^{7a}$, $(CH_2)_p-N(R^{7a})_2$ and/or $(CH_2)_p-R^8$;

K$^a$, K$^b$ denote each, independently from one another, H, Hal, CN, $R^{7a}$, $OR^{7a}$, $CONHR^{7a}$, $CONR^{7b}R^{7a}$, $CONH_2$, $NR^{7a}COR^{7b}$, $SO_2R^{7a}$, $SOR^{7a}$, $NHR^{7a}$, $N(R^792)$, $(CH_2)_p-SR^{7a}$, $(CH_2)_p-N(R^{7a})_2$ and/or $(CH_2)_p-R^8$;

$R^{7a}$, $R^{7b}$ denote each, independently from one another, linear or branched $C_1$-$C_3$-alkyl, wherein 1 to 3H atoms may be replaced by Hal; and $R^8$ denotes OH or $OR^{7a}$; and p denotes 1 or 2.

Cy$^1$, Cy$^2$, Cy$^3$, Cy$^4$, Cy$^5$ denote each, independently from one another, Ar$^1$ or Het$^1$;

$R^1$, $R^2$ denote each, independently from one another, H or $C_1$-$C_6$-alkyl, or $R^1$ and $R^2$ form together a residue according to formula (CE);

$T^1$, $T^2$, $T^3$, $T^4$, $T^8$, $T^6$, $T^7$, $T^8$ and $T^9$ denote each O; Hal denotes F, Cl or Br.

Other very specific embodiments of the present invention comprise compounds according to formula (R)-(I)-(S)-(P) or (R)-(I)-(P):

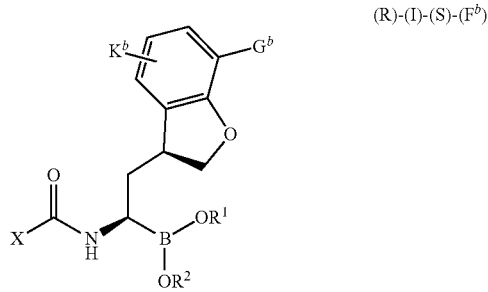
(R)-(I)-(S)-(F$^b$)

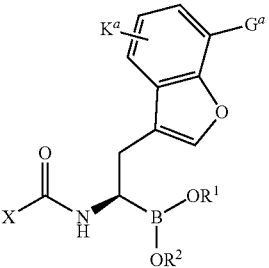
(R)-(I)-(F$^a$)

wherein

G$^a$, G$^b$ denote each, independently from one another, H, Hal, CN, $R^{7a}$, $OR^{7a}$, $CONHR^{7a}$, $CONR^{7b}R^{7a}$, $CONH_2$, $NR^{7a}COR^{7b}$, $SO_2R^{7a}$, $SOR^{7a}$, $NHR^{7a}$, $N(R^{7a})_2$, $(CH_2)_p-SR^{7a}$, $(CH_2)_p-N(R^{7a})_2$ and/or $(CH_2)_p-R^8$;

K$^a$, K$^b$ denote each, independently from one another, H, Hal, CN, $R^{7a}$, $OR^{7a}$, $CONHR^{7a}$, $CONR^{7b}R^{7a}$, $CONH_2$, $NR^{7a}COR^{7b}$, $SO_2R^{7a}$, $SOR^{7a}$, $NHR^{7a}$, $N(R^{7a})_2$, $(CH_2)_p-SR^{7a}$, $(CH_2)_N-N(R^{7a})_2$ and/or $(CH_2)_p-R^8$;

X is a heterobicycle or heterotricycle of formula ((xa1), (xb1), (xc1), (xd1), (xe1), (xf1), (xg1), (xh1) or (xi1) each, independently from one another, unsubstituted or mono- or disubstituted by F, Cl, $CH_3$, $C_2H_5$, $CF_3$, $OCH_3$, $OC_2H_5$, $COCF_3$, $SCH_3$, $SC_2H_5$, $CH_2OCH_3$, $N(CH_3)_2$, $CH_2N(CH_3)_2$ and/or $N(C_2H_5)_2$, wherein 1 of the cyclic $CH_2$ groups may be replaced $C(CH_3)_2$, $C(C_2H_5)_2$, C=O, O, S, $NCH_3$, SO or $SO_2$;

$R^1$, $R^2$ denote H or $C_1$-$C_4$-alkyl or $R^1$ and $R^2$ form together a residue according to formula (CE);

$R^{7a}$, $R^{7b}$ denote each, independently from one another, linear or branched $C_1$-$C_3$-alkyl, wherein 1 to 3H atoms may be replaced by Hal;

$R^8$ denotes OH or $OR^{7a}$; and p denotes 1 or 2.

In general, the residues included in the compounds according to formula (I) as described above may have following meaning:

LY denotes preferably —CH$_2$— or —CH$_2$—CH$_2$— wherein 1 to 4H atoms may be replaced by Hal and/or 1H atom may be replaced by Hal, $R^{3a}$ and/or $OR^{4a}$, and/or wherein 1 or 2 non-adjacent CH$_2$ groups may be replaced by O, SO and/or SO$_2$. Most preferably LY denotes —CH$_2$— or —CH$_2$—CH$_2$—, wherein 1 to 4H atom may be replaced by F or Cl and/or 1 or 2H atoms may be replaced by OH, methy, ethyl, isopropyl, $CF_3$, $CF_2CF_3$, $OCH_3$, $OCH_2CH_3$, $OCH_2CH_2OH$ and/or $CH_2OCH_3$ and/or wherein 1 CH$_2$ group of LY may be replaced by O.

$R^1$, $R^2$ denote preferably each, independently from one another H or methyl, ethyl, n-propyl or isopropyl or $R^1$ and $R^2$ form together a residue according to formula (CE) as described above. Most preferably $R^1$, $R^2$ denote H, methyl or ethyl and particular preferably $R^1$, $R^2$ denote H.

In embodiments wherein $R^{3a}$ or $R^{3b}$ represent a linear or branched $C_1$-$C_6$ alkyl, they denote preferably each, independently from one another, linear or branched methyl, ethyl, n-propyl or isopropyl, wherein 1 to 5H atoms may be replaced by F, Cl, CN, OH and OAlk, wherein Alk is preferably methyl or ethyl. Most preferably $R^{3a}$ and $R^{3b}$ denote each, independently from one another, methyl, ethyl, n-propyl or isopropyl, wherein 1, 2 or 3H atoms are replaced by F, Cl, OH, $OCH_3$, $OC_2H_5$ or $OCH(CH_3)_2$.

In embodiments wherein $R^{3a}$ or $R^{3b}$ represent independently from one another a cyclic alkyl group (cycloalkyl), they preferably denote independently from each other cyclopropyl, cyclobutyl, cyclopentyl or cyclohexyl, each unsubstituted or mono-, di- or trisubstituted by Hal (preferably F or Cl), methyl, ethyl, n-propyl, OH, CN, $OCH_3$ or $OC_2H_5$.

$R^{4a}$ and $R^{4b}$ denote preferably each, independently from one another, preferably H, methyl, furthermore ethyl, propyl, isopropyl, butyl, isobutyl, sec-butyl, tert-butyl or pentyl, wherein 1, 2 or 3H atoms are replaced by F, Cl, OH, $OCH_3$, $OC_2H_5$ or $OCH(CH_3)_2$ or $R^{4a}$ and $R^{4b}$ from together a $C_3$-$C_6$ alkylene group.

Y can denote phenyl, 1- or 2-naphthyl, 4- or 5-indanyl, 1-, 2-, 3-, 4-, 5-, 6- or 7-indolyl, 1-, 2-, 4-, 5- or 6-azulenyl, 1- or 2-tetrahydronaphthalin 5- or 6-yl, 2- or 3-furyl, 2-, 3-, 4-, 5-, 6- or 7-benzofuryl, 2,3-dihydrobenzofuran-2- or 3-yl, 2- or 3-thienyl, 2- or 3-benzothienyl, 2-, 3-, 4-, 5-, 6- or 7-benzothiophenyl, methylenedioxyphenyl, benzodioxan-6- or 7-yl or 3,4-dihydro-1,5-benzodioxepin-6- or -7-yl, each independently from one another, unsubstituted, mono-, disubstituted or trisubstituted by Hal (preferably F or Cl), CN, $R^{3a}$, OH, $OR^{3a}$, $CONR^{4a}R^{4b}$, $NR^{3a}COR^{3b}$, $SO_2R^{3a}$, $SOR^{3a}$, $NR^{4a}R^{4b}$, $Ar^2$, $Het^2$, $(CH_2)_q$—$SR^{3a}$, $(CH_2)_q$—$N(R^{4a})_2$ and/or $(CH_2)_q$—$R^6$. In particular Y can denote phenyl, 1- or 2-naphthyl 2-, 3-, 4-, 5-, 6- or 7-benzofuryl 2,3-dihydrobenzofuran-2- or 3-yl, 2- or 3-thienyl, 2- or 3-benzothienyl or benzodioxan-6- or 7-yl, each independently from one another, unsubstituted, mono-, disubstituted or trisubstituted by F, Cl, CN, $CH_3$, $C_2H_5$, $CF_3$, $OCH_3$, $OC_2H_5$, $COCF_3$, $SCH_3$, $SC_2H_5$, $CH_2OCH_3$. $N(CH_3)_2$, $CH_2N(CH_3)_2$ or $N(C_2H_5)_2$. In case Y denotes a disubstituted phenyl the substituents are preferably in 2,4-, 2,5- or 3,4-position, most preferably in 2,4- or 3,4-position. In case Y denotes a trisubstituted phenyl the substituents are preferably in 2,3, 4-position.

In particular Y can denote o-, m- or p-tolyl, o-, m- or p-ethylphenyl, o-, m- or p-propylphenyl, o-, m- or p-isopropylphenyl, o-, m- or p-tert-butylphenyl, o-, m- or p-acetamidophenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-trifluormethyl-phenyl, o-, m- or p-trichloromethyl-phenyl, o-, m- or p-(methylsulfonyl)phenyl, o-, m- or p-phenoxyphenyl, o-, m- or p-methoxymethyl-phenyl further preferably 2,4-, 2,5-, 2,6- or 3,4-dimethylphenyl, 2,4-, 2,5- or 3,4-difluorophenyl, 2,4-, 2,5- or 3,4-dichloro-phenyl, 2,4-, 2,5- or 3,4-dibromophenyl, 2,5- or 3,4-dimethoxyphenyl, 2,3,4-, 2,3,5-, 2,3,6-, 2,4,6- or 3,4,5-trichlorophenyl, 2,3,4-, 2,3,5-, 2,3,6-, 2,4,6- or 3,4,5-trifluorophenyl, 2,3,4-, 2,3,5-, 2,3,6-, 2,4,6- or 3,4, 5-trimethylphenyl, 2,3,4-, 2,3,5-, 2,3,6-, 2,4,6- or 3,4,5-tris trifluormethyl-phenyl, 2,3,4-, 2,3,5-, 2,3,6-, 2,4,6- or 3,4,5- tristrichlormethyl-phenyl, 2,3,4-, 2,3,5-, 2,3,6-, 2,4,6- or 3,4,5-trimethoxymethyl-phenyl, 2,4,6-trimethoxyphenyl, p-iodophenyl, 2-fluoro-3-chlorophenyl, 2-fluoro-3-bromophenyl, 2,3-difluoro-4-bromophenyl, 3-bromo-3-methoxyphenyl, 2-chloro-3-methoxyphenyl, 2-fluoro-3-methoxyphenyl, 2-chloro-3-acetamidophenyl, 2-fluoro-3-methoxyphenyl, 2-chloro-3-acetamidophenyl, 2,3-dimethyl-4-chlorophenyl, 2,3-dimethyl-4-fluorophenyl.

Y can also denote 1- or 2-naphthyl, 4- or 5-indanyl, 1-, 2-, 4-, 5- or 6-azulenyl, 1- or 2-tetrahydronaphthalin 5- or 6-yl, 2- or 3-furyl, 2-, 3-, 4-, 5-, 6- or 7-benzofuryl, 2-, 3-, 4-, 5-, 6- or 7-benzothiophenyl, methylenedioxyphenyl, benzodioxan-6- or 7-yl or 3,4-dihydro-1,5-benzodioxepin-6- or -7-yl. Particular preferred substituents of Y are selected from a group comprising, Cl, CN, $CH_3$, $C_2H_5$, $CF_3$, $OCH_3$, $OC_2H_5$, $COCF_3$, $SCH_3$, $SC_2H_5$, $CH_2OCH_3$, $N(CH_3)_2$, $CH_2N(CH_3)_2$ or $N(C_2H_5)_2$.

$Ar^2$ denotes preferably phenyl, which is unsubstituted or mono- or disubstituted by Hal, CN, $R^{3a}$, $OR^{3a}$, $CONHR^{3a}$, $NH_2$, $NHR^{3a}$ and/or $N(R^{3a})_2$. Thus, $Ar^2$ preferably denotes e.g. phenyl, o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methyl-aminocarbonyl)phenyl, o-, m- or p-acetamidophenyl, o-, m- or p-methoxyphenyl, o-, m- or p-ethoxyphenyl, o-, m- or p-(N,N-dimethylamino)phenyl, o-, m- or p-(N-ethylamino) phenyl, o-, m- or p-(N,N-diethylamino)phenyl, o-, m- or p-fluorophenyl, o-, m- or p-bromophenyl, o-, m- or p-chlorophenyl, o-, m- or p-cyanophenyl.

$Het^2$ denotes preferably a saturated, unsaturated or aromatic 5- or 6-membered heterocycle having 1 to 4 N, O and/or S atoms, which is unsubstituted or mono- or disubstituted by Hal, CN, $R^{3a}$, $OR^{3a}$, $CONHR^{3a}$, $NH_2$, $NHR^{3a}$ and/or $N(R^{3a})_2$. Thus, $Het^2$ may e.g. denote 2- or 3-furyl, 2- or 3-thienyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, imidazolyl, morpholinyl or piperazinyl.

Alk denotes preferably methy, ethyl, propyl, isopropyl, butyl, isobutyl, sec-butyl or tert-butyl, pentyl or hexyl, most preferably methy, ethyl, propyl or isopropyl, most preferably methy, ethyl, n-propyl or isopropyl.

Hal denotes preferably F, Cl or Br, most preferably F or $C_1$.

m denotes preferably 0, 1 or 2, more 1 or 2 and most preferably 1.

q denotes preferably 0, 1, 2, 3 or 4 and even more preferably 0, 1 or 2.

Particular embodiments of the present invention comprise the compounds selected from the group consisting of:

[(1R)-2-[(3S)-2,3-dihydro-1-benzofuran-3-yl]-1-{[(1S,2R,4R)-7-oxabicyclo[2.2.1]heptan-2-yl]formamido}ethyl] boronic acid;

[(1R)-2-[(3S)-2,3-dihydro-1-benzofuran-3-yl]-1-{[(1R,2S,4S)-7-oxabicyclo[2.2.1]heptan-2-yl]formamido}ethyl] boronic acid;

[(1R)-1-{[(1S,2R,4R)-7-oxabicyclo[2.2.1]heptan-2-yl]formamido}-2-(thiophen-3-yl)ethyl]boronic acid;

[(1R)-2-(1-benzofuran-3-yl)-1-{[(1R,8S)-11-oxatricyclo[6.2.1.0$^{2,7}$]undeca-2(7),3,5-trien-1-yl]formamido}ethyl] boronic acid;

[(1S)-2-(1-benzofuran-3-yl)-1-{[(1R,8S)-11-oxatricyclo[6.2.1.0$^{2,7}$]undeca-2(7),3,5-trien-1-yl]formamido}ethyl] boronic acid;

[(1R)-2-(1-benzofuran-3-yl)-1-{[(1S,8R)-11-oxatricyclo[6.2.1.0$^{2,7}$]undeca-2(7),3,5-trien-1-yl]formamido}ethyl] boronic acid;

[(1S)-2-(1-benzofuran-3-yl)-1-{[(1S,8R)-11-oxatricyclo[6.2.1.0$^{2,7}$]undeca-2(7),3,5-trien-1-yl]formamido}ethyl] boronic acid;

[(1R)-2-(1-benzofuran-3-yl)-1-{[(1R,2S,4S)-7-oxabicyclo[2.2.1]heptan-2-yl]formamido}ethyl]boronic acid;

[(1R)-2-(1-benzofuran-3-yl)-1-{[(1S,2R,4R)-7-oxabicyclo[2.2.1]heptan-2-yl]formamido}ethyl]boronic acid;

[(1R)-2-(1-benzofuran-3-yl)-1-{[(1R,2R,4S)-7-oxabicyclo[2.2.1]heptan-2-yl]formamido}ethyl]boronic acid;

[(1S)-2-(1-benzofuran-3-yl)-1-{[(1R,2R,4S)-7-oxabicyclo[2.2.1]heptan-2-yl]formamido}ethyl]boronic acid;

[(1R)-2-(7-chloro-1-benzofuran-3-yl)-1-{[(1R,2S,4S)-7-oxabicyclo[2.2.1]heptan-2-yl]formamido}ethyl]boronic acid;

[(1R)-2-(7-chloro-1-benzofuran-3-yl)-1-{[(1S,2R,4R)-7-oxabicyclo[2.2.1]heptan-2-yl]formamido}ethyl]boronic acid;
[(1R)-2-[(3R)-7-methyl-2,3-dihydro-1-benzofuran-3-yl]-1-{[(1S,2R,4R)-7-oxabicyclo[2.2.1]heptan-2-yl]formamido}ethyl]boronic acid;
[(1R)-2-[(3S)-7-methyl-2,3-dihydro-1-benzofuran-3-yl]-1-{[(1S,2R,4R)-7-oxabicyclo[2.2.1]heptan-2-yl]formamido}ethyl]boronic acid;
[(1R)-2-[(3S)-2,3-dihydro-1-benzofuran-3-yl]-1-{[(1R,8S)-11-oxatricyclo[6.2.1.0$^{2,7}$]undeca-2(7),3,5-trien-1-yl]formamido}ethyl]boronic acid;
[(1R)-2-(1-benzofuran-3-yl)-1-{[(1S,6S,7R)-3-cyclopropyl-4-oxo-10-oxa-3-azatricyclo[5.2.1.0$^{1,5}$]dec-8-en-6-yl]formamido}ethyl]boronic acid;
[(1R)-2-[(3S)-2,3-dihydro-1-benzofuran-3-yl]-1-{[(1S,8R)-11-oxatricyclo[6.2.1.0$^{2,7}$]undeca-2(7),3,5-trien-1-yl]formamido}ethyl]boronic acid;
[(1R)-2-(7-methyl-1-benzofuran-3-yl)-1-{[(1R,8S)-11-oxatricyclo[6.2.1.0$^{2,7}$]undeca-2,4,6-trien-1-yl]formamido}ethyl]boronic acid;
[(1R)-2-(7-methyl-1-benzofuran-3-yl)-1-{[(1S,8R)-11-oxatricyclo[6.2.1.0$^{2,7}$]undeca-2,4,6-trien-1-yl]formamido}ethyl]boronic acid;
[(1R)-2-[(3S)-2,3-dihydro-1-benzofuran-3-yl]-1-{[(1S,8R)-8-methyl-11-oxatricyclo[6.2.1.0$^{2,7}$]undeca-2,4,6-trien-1-yl]formamido}ethyl]boronic acid;
[(1R)-2-(1-benzofuran-3-yl)-1-{[(1R,8S)-11-oxatricyclo[6.2.1.0$^{2,7}$]undeca-2(7),3,5-trien-9-yl]formamido}ethyl]boronic acid;
[(1R)-2-[(3S)-2,3-dihydro-1-benzofuran-3-yl]-1-{[(1R,8S)-8-methyl-11-oxatricyclo[6.2.1.0$^{2,7}$]undeca-2,4,6-trien-1-yl]formamido}ethyl]boronic acid;
[(1R)-2-(1-benzofuran-3-yl)-1-{[(1S,8R)-11-oxatricyclo[6.2.1.0$^{2,7}$]undeca-2(7),3,5-trien-9-yl]formamido}ethyl]boronic acid;
[(1R)-2-(2,4-dimethylphenyl)-1-{[(1S,2R,4R)-7-oxabicyclo[2.2.1]heptan-2-yl]formamido}ethyl]boronic acid;
[(1R)-2-cyclohexyl-1-{[(1S,2R,4R)-7-oxabicyclo[2.2.1]heptan-2-yl]formamido}ethyl]boronic acid;
[(1R)-1-{[(1S,2R,4R)-7-oxabicyclo[2.2.1]heptan-2-yl]formamido}-3-phenylpropyl]boronic acid;
[(1R)-3-methyl-1-{[(1S,2R,4R)-7-oxabicyclo[2.2.1]heptan-2-yl]formamido}butyl]boronic acid;
[(1S)-2-(1-benzofuran-3-yl)-1-{[(1S,2R,4R)-7-oxabicyclo[2.2.1]heptan-2-yl]formamido}ethyl]boronic acid;
[(1S)-2-(1-benzofuran-3-yl)-1-{[(1R,2S,4S)-7-oxabicyclo[2.2.1]heptan-2-yl]formamido}ethyl]boronic acid;
[(1R)-2-(1-benzofuran-3-yl)-1-{[(1S,2S,4R)-7-oxabicyclo[2.2.1]heptan-2-yl]formamido}ethyl]boronic acid;
[(1S)-2-(1-benzofuran-3-yl)-1-{[(1S,2S,4R)-7-oxabicyclo[2.2.1]heptan-2-yl]formamido}ethyl]boronic acid;
[(1R)-2-[(3S)-2,3-dihydro-1-benzofuran-3-yl]-1-{[(1S,2S,4R)-7-oxabicyclo[2.2.1]heptan-2-yl]formamido}ethyl]boronic acid;
[(1R)-2-[(3S)-2,3-dihydro-1-benzofuran-3-yl]-1-{[(1R,2R,4S)-7-oxabicyclo[2.2.1]heptan-2-yl]formamido}ethyl]boronic acid;
[(1S)-2-[(3S)-2,3-dihydro-1-benzofuran-3-yl]-1-{[(1S,2S,4R)-7-oxabicyclo[2.2.1]heptan-2-yl]formamido}ethyl]boronic acid;
[(1S)-2-[(3S)-2,3-dihydro-1-benzofuran-3-yl]-1-{[(1R,2R,4S)-7-oxabicyclo[2.2.1]heptan-2-yl]formamido}ethyl]boronic acid;
[(1R)-2-[(3R)-2,3-dihydro-1-benzofuran-3-yl]-1-{[(1S,2S,4R)-7-oxabicyclo[2.2.1]heptan-2-yl]formamido}ethyl]boronic acid;
[(1R)-2-[(3R)-2,3-dihydro-1-benzofuran-3-yl]-1-{[(1R,2R,4S)-7-oxabicyclo[2.2.1]heptan-2-yl]formamido}ethyl]boronic acid;
[(1S)-2-[(3R)-2,3-dihydro-1-benzofuran-3-yl]-1-{[(1S,2S,4R)-7-oxabicyclo[2.2.1]heptan-2-yl]formamido}ethyl]boronic acid;
[(1S)-2-[(3R)-2,3-dihydro-1-benzofuran-3-yl]-1-{[(1R,2R,4S)-7-oxabicyclo[2.2.1]heptan-2-yl]formamido}ethyl]boronic acid;
[(1S)-2-[(3S)-2,3-dihydro-1-benzofuran-3-yl]-1-{[(1S,2R,4R)-7-oxabicyclo[2.2.1]heptan-2-yl]formamido}ethyl]boronic acid;
[(1S)-2-[(3S)-2,3-dihydro-1-benzofuran-3-yl]-1-{[(1R,2S,4S)-7-oxabicyclo[2.2.1]heptan-2-yl]formamido}ethyl]boronic acid;
[(1R)-2-[(3R)-2,3-dihydro-1-benzofuran-3-yl]-1-{[(1S,2R,4R)-7-oxabicyclo[2.2.1]heptan-2-yl]formamido}ethyl]boronic acid;
[(1R)-2-[(3R)-2,3-dihydro-1-benzofuran-3-yl]-1-{[(1R,2S,4S)-7-oxabicyclo[2.2.1]heptan-2-yl]formamido}ethyl]boronic acid;
[(1S)-2-[(3R)-2,3-dihydro-1-benzofuran-3-yl]-1-{[(1S,2R,4R)-7-oxabicyclo[2.2.1]heptan-2-yl]formamido}ethyl]boronic acid;
[(1S)-2-[(3R)-2,3-dihydro-1-benzofuran-3-yl]-1-{[(1R,2S,4S)-7-oxabicyclo[2.2.1]heptan-2-yl]formamido}ethyl]boronic acid;

and prodrugs, solvates, tautomers, oligomers, adducts or stereoisomers thereof as well as the pharmaceutically acceptable salts of each of the foregoing, including mixtures thereof in all ratios.

The term solvates of the compounds is taken to mean adductions of inert solvent molecules onto the compounds which form owing to their mutual attractive force. Solvates are, for example, mono- or dihydrates or alkoxides.

It is understood, that the invention also relates to the solvates of the salts.

The term pharmaceutically acceptable derivatives is taken to mean, for example, the salts of the compounds according to the invention and also so-called prodrug compounds.

As used herein and unless otherwise indicated, the term "prodrug" means a derivative of a compound of formula (I) that can hydrolyze, oxidize, or otherwise react under biological conditions (in vitro or in vivo) to provide an active compound, particularly a compound of formula (I). Examples of prodrugs include, but are not limited to, derivatives and metabolites of a compound of formula (I) that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula (I), for example mixtures of two diastereomers, for example in the ratio 1:1, 1:2, 1:3, 1:4, 1:5, 1:10, 1:100 or 1:1000.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution.

The invention further comprises a process for the preparation of a compound of the formula (I) as described above and pharmaceutically acceptable salts, tautomers and stereoisomers thereof, characterized in that a compound of formula (III)

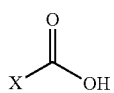

(III)

is coupled with a compound of formula (VI)

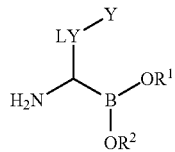

(IV)

wherein all residues of formula (III) and formula (IV) are as defined above and wherein the obtained compound of formula (Ib) may subsequently converted into a compound of formula (Ia), by treatment with HCl, HBr, HI and/or TFA, in the presence or absence of an excess of a small molecular weight boronic acid

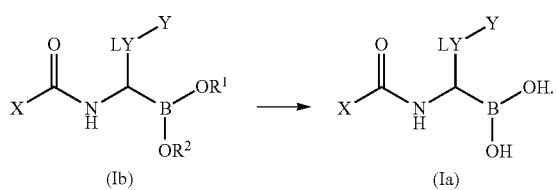

The following abbreviations refer to the abbreviations used below:

AcOH (acetic acid), ACN (acetonitrile), BINAP (2,2'-bis (disphenylphosphino)-1,1'-binaphthalene), dba (dibenzylidene acetone), tBu (tert-Butyl), tBuOK (potassium tert-butoxide), CDI (1,1'-Carbonyldiimidazole), DBU (1,8-dizabicyclo[5.4.0]undec-7-ene), DCC (dicyclohexylcarbodiimide), DCM (dichloromethane), DIAD (diisobutylazodicarboxylate), DIC (diisopropilcarbodiimide), DIEA (diisopropyl ethylamine), DMA (dimethyl acetamide), DMAP (4-dimethylaminopyridine), DMSO (dimethyl sulfoxide), DMF (N,N-dimethylformamide), EDC.HCl (1-ethyl-3-(3-dimethylaminopropyl)carbodiimide hydrochloride), EtOAc or EE (ethyl acetate), EtOH (ethanol), g (gram), cHex (cyclohexane), HATU (dimethylamino-([1,2,3]triazolo[4,5-b]pyridin-3-yloxy)-methylene]-dimethyl-ammonium hexafluorophosphate), HOBt (N-hydroxybenzotriazole), HPLC (high performance liquid chromatography), hr (hour), MHz (Megahertz), McOH (methanol), min (minute), mL (milliliter), mmol (millimole), mM (millimolar), mp (melting point), MS (mass spectrometry), MW (microwave), NMM (N-methyl morpholine), NMR (Nuclear Magnetic Resonance), NBS (N-bromo succinimide), PBS (phosphate buffered saline), PMB (para-methoxybenzyl), PyBOP (benzotriazol-1-yl-oxytripyrrolidinophosphonium hexafluorophosphate), rt (room temperature), TBAF (tetra-butylammonium fluoride), TBTU (N,N,N',N'-tetramethyl-O-(benzotriazol-1-yl)uronium tetrafluoroborate), T3P (propane phosphonic acid anhydride), TEA (triethyl amine), TFA (trifluoroacetic acid), THF (tetrahydrofuran), PetEther (petroleum ether), TBME (tert-butyl methyl ether), TLC (thin layer chromatography), TMS (trimethylsilyl), TMSI (trimethylsilyl iodide), UV (ultraviolet).

Generally, compounds of formula (I), wherein all residues are defined as above, can be obtained from a compound of formula (III) as outlined in Scheme 1.

Scheme 1

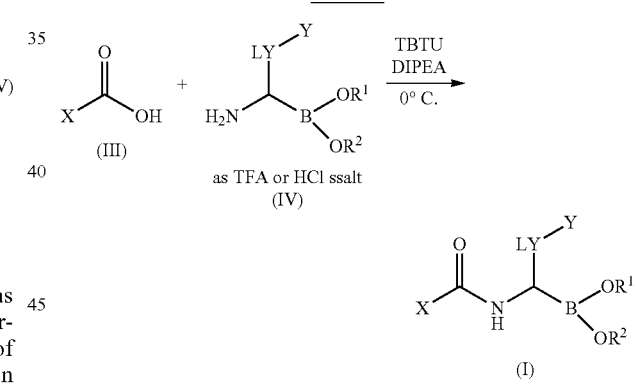

The first step consists in the reaction of a compound of formula (III), wherein X is defined as above, with a compound of formula (IV), wherein $R^1$, $R^2$, LY and Y are defined as above. The reaction is performed using conditions and methods well known to those skilled in the art for the preparation of amides from a carboxylic acid with standard coupling agents, such as but not limited to HATU, TBTU, polymer-supported 1-alkyl-2-chloropyridinium salt (polymer-supported Mukaiyama's reagent), 1-methyl-2-chloropyridinium iodide (Mukaiyama's reagent), a carbodiimide (such as DCC, DIC, EDC) and HOBt, PyBOP® and other such reagents well known to those skilled in the art, preferably TBTU, in the presence or absence of bases such as TEA, DIEA, NMM, polymer-supported morpholine, preferably DIEA, in a suitable solvent such as DCM, THF or DMF, at a temperature between −10° C. to 50° C., preferably at 0° C., for a few hours, e.g. one hour to 24 h. Alternatively, the compounds of formula (III) could be converted to carboxylic acid derivatives such as acyl halides or anhydrides, by methods well known to those skilled in the art, such as but not limited to treatment with $SOCl_2$, $POCl_3$, $PCl_5$, $(COCl)_2$, in the presence or absence of catalytic amounts of DMF, in the presence or absence of a suitable solvent such as toluene, DCM, THF, at a temperature rising from 20° C. to 100° C., preferably at 50° C., for a few hours, e.g. one hour to 24 h. Conversion of the carboxylic acid derivatives to compounds of formula (I), can be achieved using conditions and methods well known to those skilled in the art for the preparation of amides from a carboxylic acid derivative (e.g. acyl chloride) with alkyl amines, in the presence of bases such as TEA, DIEA, NMM in a suitable solvent such as DCM, THF or DMF, at a temperature rising from 20° C. to 100° C., preferably at 50° C., for a few hours, e.g. one hour to 24 h.

In the process described above the reaction between the compound of formula (III) and the compound of formula (IV) is preferably performed in the presence of a coupling agent selected from HATU, TBTU, polymer-supported 1-alkyl-2-chloropyridinium salt (polymer-supported Mukaiyama's reagent), 1-methyl-2-chloropyridinium iodide (Mukaiyama's reagent), a carbodiimide.

Compounds of formula (Ia), wherein X, LY and Y are defined as above and wherein $R^1$ and $R^2$ are H, can be prepared starting from compounds of formula (Ib), using methods well known to those skilled in the art for the hydrolysis of boronic esters, such as but not limited to treatment with HCl, HBr, HI, TFA, in the presence or absence of an excess of a small molecular weight boronic acid, such as but not limited to $iBuB(OH)_2$ (Scheme 2).

Scheme 2

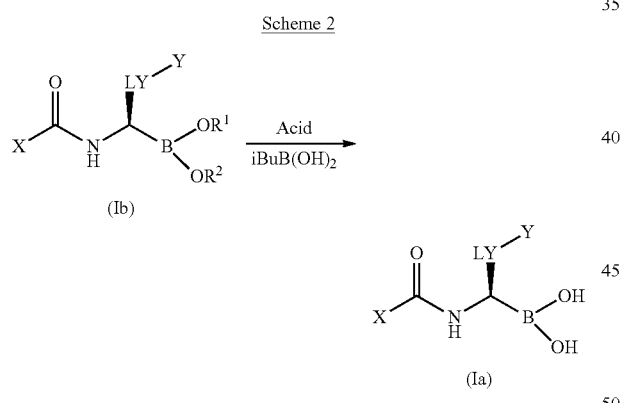

Compounds of formula (III) or (IV) are either commercially available or can be prepared by methods well known to those skilled in the art.

In general, compounds of formula (IV) are for example accessible by the following scheme 3a:

Boronate ester

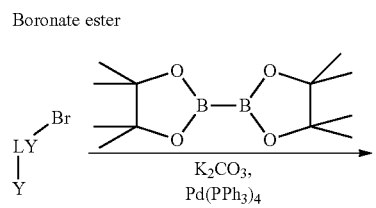

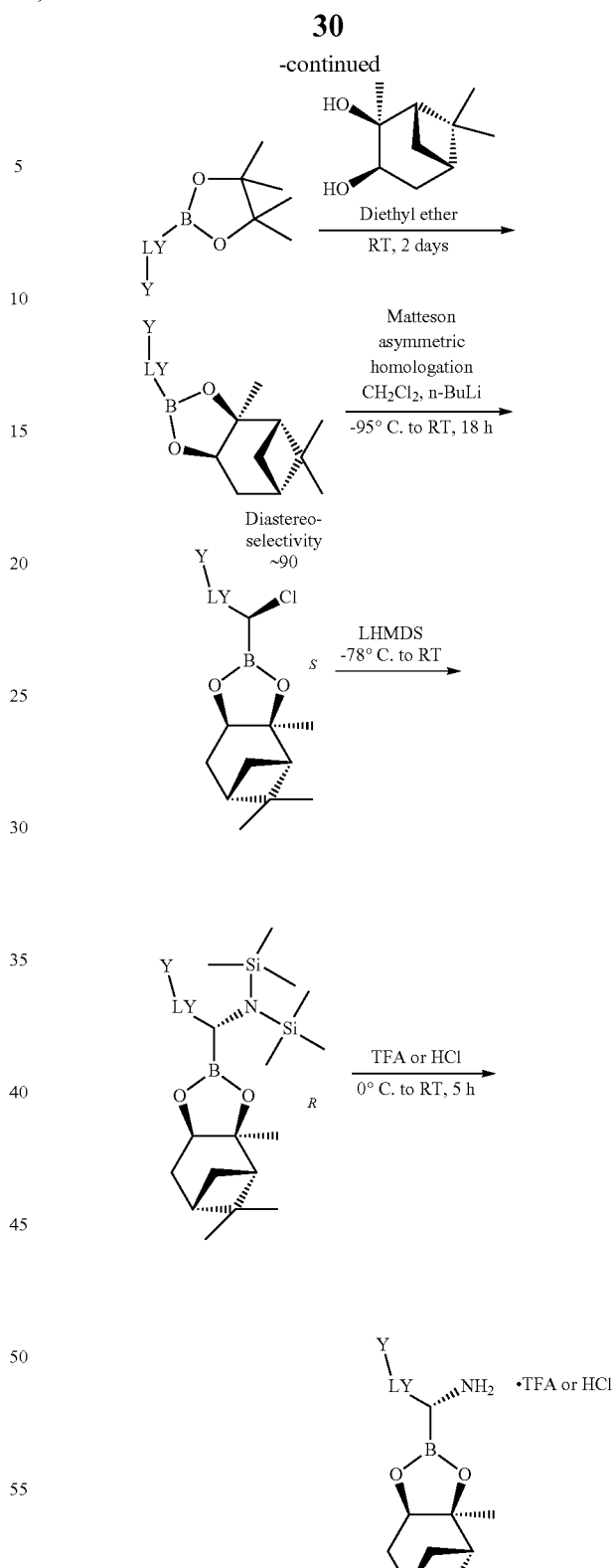

The synthesis of compounds of formula (IV) is further described in WO 2016/050356, WO 2016/050355, WO 2016/050359, and WO 2016/050358.

Compounds of formula (III) are for example accessible by the routes described in Scheme 4, 5 and 6:

Scheme 4
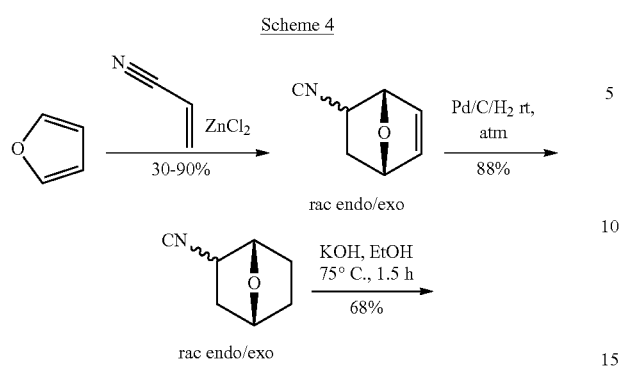
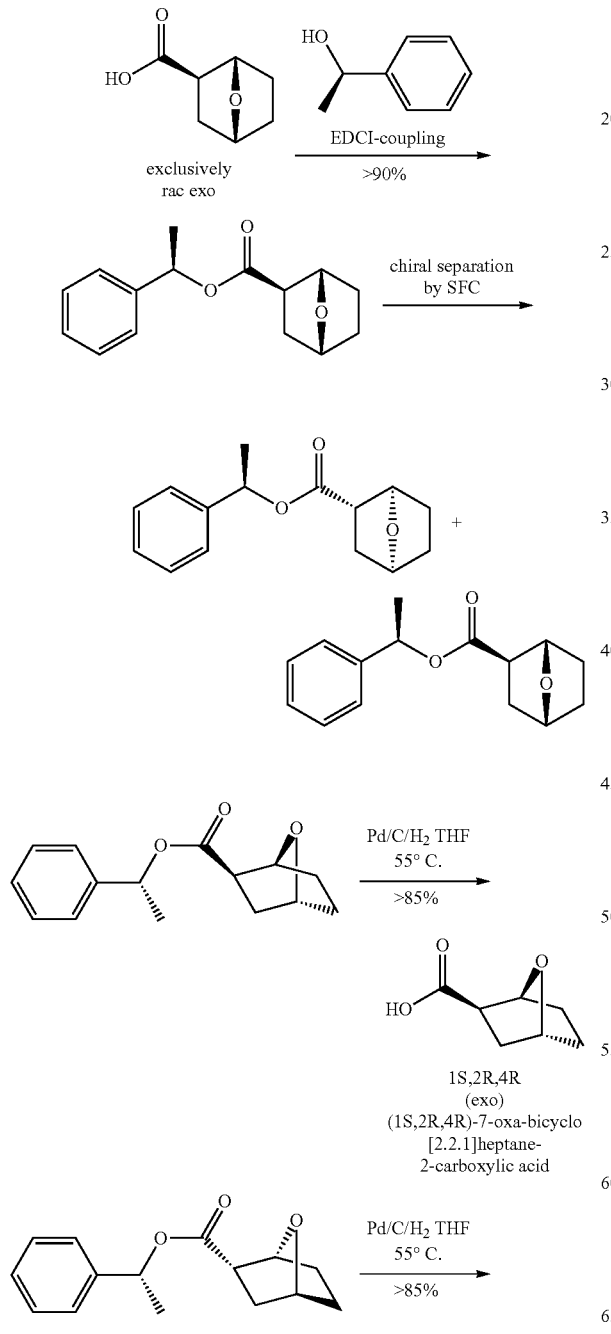
1S,2R,4R
(exo)
(1S,2R,4R)-7-oxa-bicyclo
[2.2.1]heptane-
2-carboxylic acid
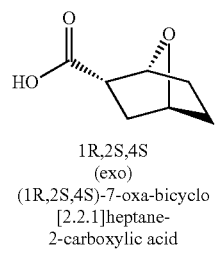
1R,2S,4S
(exo)
(1R,2S,4S)-7-oxa-bicyclo
[2.2.1]heptane-
2-carboxylic acid
By similar approaches also substituted 7-oxa-bicyclo[2.2.1]heptane-2-carboxylic acids can be synthesised.
Scheme 5
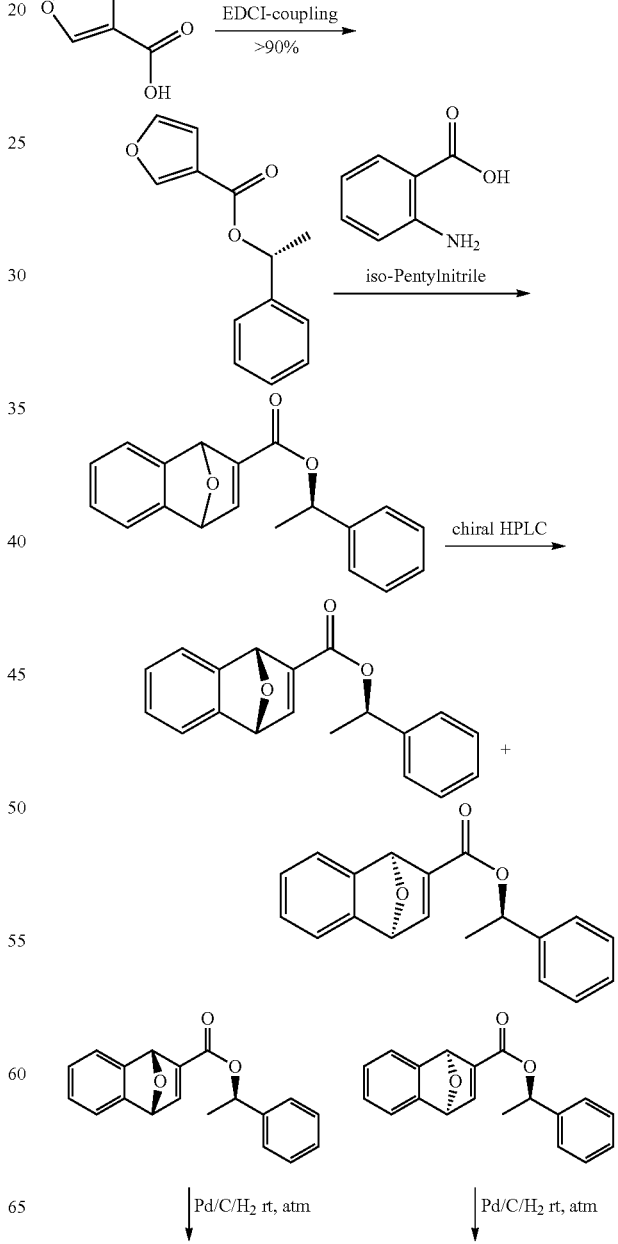

-continued

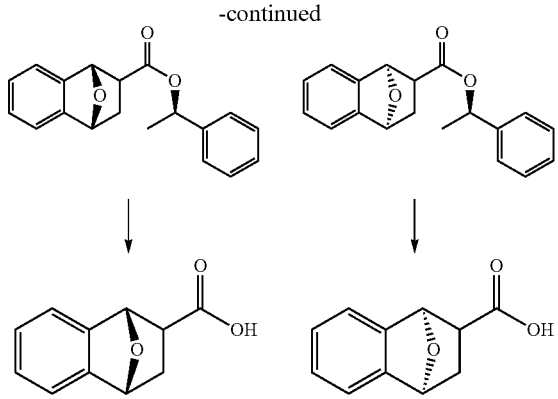

By similar approaches also substituted 11-oxatricyclo[6.2.1.0$^{2,7}$]undeca-2,4,6,9-tetraene-9-carboxylic acids can be synthesised.

Scheme 6

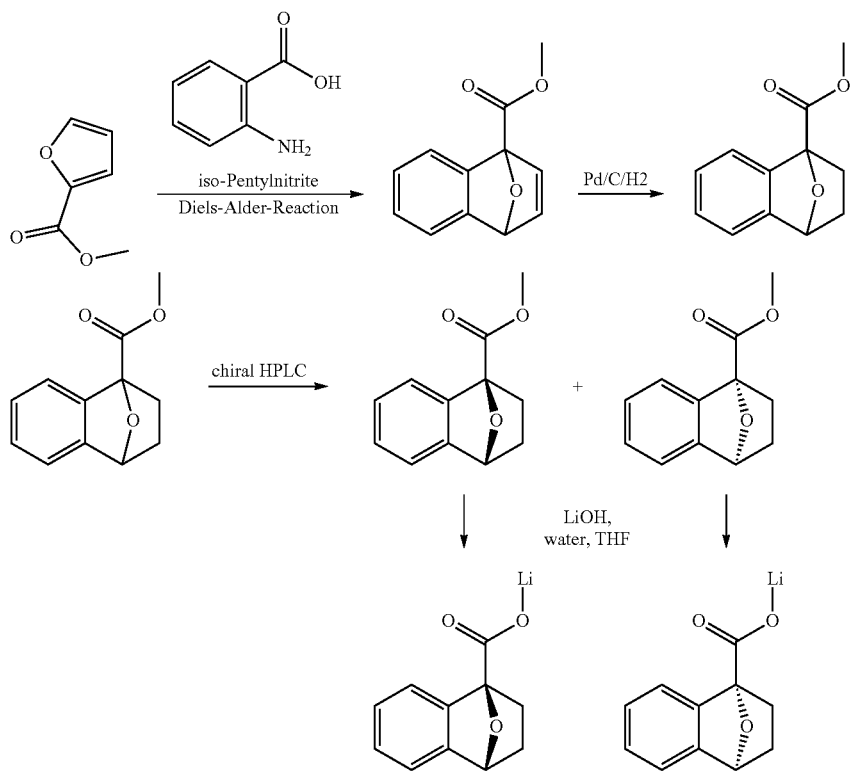

By similar approaches starting from substituted furane-2-carboxylic acids, substituted 11-oxatricyclo[6.2.1.0$^{2,7}$]undeca-2,4,6-triene-1-carboxylic acids can be synthesised. Also substituted anthranilic acids can be used to synthesise corresponding compounds which carry additional substituents in the aromatic moiety.

If the above set of general synthetic methods is not applicable to obtain compounds according to formula (I) and/or necessary intermediates for the synthesis of compounds of formula (I), suitable methods of preparation known by a person skilled in the art should be used.

In general, the synthesis pathways for any individual compounds of formula (I) will depend on the specific substitutents of each molecule and upon the ready availability of Intermediates necessary; again such factors being appreciated by those of ordinary skill in the art. For all the protection and de-protection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3rd Edition 1999.

Compounds of this invention can be isolated in association with solvent molecules by crystallization from evaporation of an appropriate solvent. The pharmaceutically acceptable acid addition salts of the compounds of formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compounds of formula (I), which contain an acid center, with a suitable base. Both types of salts may be formed or interconverted using ion-exchange resin techniques.

Depending on the conditions used, the reaction times are generally between a few minutes and 14 days, and the reaction temperature is between about −30° C. and 140° C., normally between −10° C. and 90° C., in particular between about 0° C. and about 70° C.

Compounds of the formula (I) can furthermore be obtained by liberating compounds of the formula (I) from one of their functional derivatives by treatment with a solvolysing or hydrogenolysing agent.

Preferred starting materials for the solvolysis or hydrogenolysis are those which conform to the formula (I), but contain corresponding protected amino and/or hydroxyl groups instead of one or more free amino and/or hydroxyl groups, preferably those which carry an amino-protecting group instead of an H atom bound to an N atom, in particular those which carry an R'—N group, in which R' denotes an amino-protecting group, instead of an HN group, and/or those which carry a hydroxyl-protecting group instead of the H atom of a hydroxyl group, for example those which conform to the formula (I), but carry a —COOR" group, in which R" denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxy-carbonyl, ethoxycarbonyl, 2,2,2-trichloroethoxycarbonyl, BOC (tert-butoxy-carbonyl) and 2-iodoethoxycarbonyl; aralkoxycarbonyl, such as CBZ ("carbo-benz-oxy"), 4-methoxybenzyloxycarbonyl and FMOC; and aryl-sulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitro-benzoyl, p-toluenesulfonyl, tert-butyl and acetyl, where benzyl and tert-butyl are particularly preferred.

The term "solvates of the compounds" is taken to mean adductions of inert solvent molecules onto the compounds which form owing to their mutual attractive force. Solvates are, for example, mono- or dihydrates or alcoholates.

The compounds of the formula (I) are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as THF or dioxane, amides, such as DMF, halogenated hydrocarbons, such as DCM, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (rt).

The BOC, OBut and Mtr groups can, for example, preferably be cleaved off using TFA in DCM or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, tri-fluoro-methylbenzene, chloroform or DCM; alcohols, such as methanol, ethanol, isopropanol, n-propanol, n-butanol or tert-butanol; ethers, such as diethyl ether, diisopropyl ether, tetrahydrofurane (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as EtOAc, or mixtures of the said solvents.

Esters can be saponified, for example, using LiOH, NaOH or KOH in water, water/THF, water/THF/ethanol or water/dioxane, at temperatures between 0 and 100° C. Furthermore, ester can be hydrolysed, for example, using acetic acid, TFA or HCl.

Free amino groups can furthermore be acylated in a conventional manner using an acyl chloride or anhydride or alkylated using an unsubstituted or substituted alkyl halide or reacted with $CH_3$—C(=NH)—OEt, advantageously in an inert solvent, such as DCM or THF and/or in the presence of a base, such as triethylamine or pyridine, at temperatures between −60° C. and +30° C.

Throughout the specification, the term leaving group preferably denotes Cl Br, I or a reactively modified OH group, such as, for example, an activated ester, an imidazolide or alkylsulfonyloxy having 1 to 6 carbon atoms (preferably methylsulfonyloxy or trifluoromethylsulfonyloxy) or arylsulfonyloxy having 6 to 10 carbon atoms (preferably phenyl- or p tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N-hydroxysuccinimide.

Pharmaceutical Salts and Other Forms

The said compounds of the formula (I) can be used in their final non-salt form. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds of the formula (I) are for the most part prepared by conventional methods. If the compound of the formula (I) contains an acidic center, such as a carboxyl group, one of its suitable salts can be formed by reacting the compound with a suitable base to give the corresponding base-addition salt. Such bases are, for example, alkali metal hydroxides, including potassium hydroxide and sodium hydroxide; alkaline earth metal hydroxides, such as magnesium hydroxide and calcium hydroxide; and various organic bases, such as piperidine, diethanolamine and N-methyl-glucamine (meglumine), benzathine, choline, diethanolamine, ethylenediamine, benethamine, diethylamine, piperazine, lysine, L-arginine, ammonia, triethanolamine, betaine, ethanolamine, morpholine and tromethamine. In the case of certain compounds of the formula I, which contain a basic center, acid-addition salts can be formed by treating these compounds with pharmaceutically acceptable organic and inorganic acids, for example hydrogen halides, such as hydrogen chloride or hydrogen bromide, other mineral acids and corresponding salts thereof, such as sulfate, nitrate or phosphate and the like, and alkyl- and monoaryl-sulfonates, such as methanesulfonate, ethanesulfonate, toluenesulfonate and benzenesulfonate, and other organic acids and corresponding salts thereof, such as carbonate, acetate, trifluoro-acetate, tartrate, maleate, succinate, citrate, benzoate, salicylate, ascorbate and the like. Accordingly, pharmaceutically acceptable acid-addition salts of the compounds of the formula (I) include the following: acetate, adipate, alginate, aspartate, benzoate, benzene-sulfonate (besylate), bisulfate, bisulfite, bromide, camphorate, camphor-sulfonate, caprate, caprylate, chloride, chlorobenzoate, citrate, cyclamate, cinnamate, digluconate, dihydrogen-phosphate, dinitrobenzoate, dodecyl-sulfate, ethanesulfonate, formate, glycolate, fumarate, galacterate (from mucic acid), galacturonate, glucoheptanoate, gluco-nate, glutamate, glycerophosphate, hemisuccinate, hemisulfate, heptanoate, hexanoate, hippurate, hydrochloride, hydrobromide, hydroiodide, 2-hydroxy-ethane-sulfonate, iodide, isethionate, isobutyrate, lactate, lactobionate, malate, maleate, malonate, mandelate, metaphosphate, methanesulfonate, methyl benzoate, mono-hydrogen-phosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction. Both types of salts may be formed or interconverted preferably using ion-exchange resin techniques.

Furthermore, the base salts of the compounds of the formula (I) include aluminium, ammonium, calcium, copper, iron (III), iron(II), lithium, magnesium, manganese(III), manganese(II), potassium, sodium and zink salts, but this is not intended to represent a restriction. Of the above-mentioned salts, preference is given to ammonium; the alkali metal salts sodium and potassium, and the alkaline earth metal salts calcium and magnesium. Salts of the compounds of the formula (I) which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzyl-ethylen-ediamine (benzathine), dicyclohexylamine, diethanolamine, diethyl-amine, 2-diethyl-amino-ethanol, 2-dimethyl-amino-ethanol, ethanolamine, ethylenediamine, N-ethylmorpholine, N-ethyl-piperidine, glucamine, glucosamine, histidine, hydrabamine, isopropyl-amine, lidocaine, lysine, meglumine (N-methyl-D-glucamine), morpholine, piperazine, piperidine, polyamine resins, procaine, purines, theobromine, triethanolamine, triethylamine, trimethylamine, tripropyl-amine and tris(hydroxy-methyl)-methylamine (tromethamine), but this is not intended to represent a restriction.

Compounds of the formula (I) of the present invention which contain basic nitrogen-containing groups can be quaternised using agents such as ($C_1$-$C_4$)-alkyl halides, for example methyl, ethyl, isopropyl and tert-butyl chloride, bromide and iodide; di($C_1$-$C_4$)alkyl sulfates, for example dimethyl, diethyl and diamyl sulfate; ($C_{10}$-$C_{18}$)alkyl halides, for example decyl, do-decyl, lauryl, myristyl and stearyl chloride, bromide and iodide; and aryl-($C_1$-$C_4$)alkyl halides, for example benzyl chloride and phenethyl bromide. Both water- and oil-soluble compounds of the formula (I) can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tro-meth-amine, but this is not intended to represent a restriction.

The acid-addition salts of basic compounds of the formula (I) are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula (I) are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds of the formula (I) are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound of the formula (I) contains more than one group which is capable of forming pharmaceutically acceptable salts of this type, the formula (I) also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the term "pharmaceutically acceptable salt" in the present connection is taken to mean an active ingredient which comprises a compound of the formula (I) in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Owing to their molecular structure, the compounds of the formula (I) are chiral and can accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the Intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the (R)- and (S)-forms of tartaric acid, diacetyltartaric acid, dibenzoyltartaric acid, mandelic acid, malic acid, lactic acid, suitable N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

Isotopes

There is furthermore intended that a compound of the formula (I) includes isotope-labelled forms thereof. An isotope-labelled form of a compound of the formula (I) is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula (I) by well-known methods include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{38}Cl$, respectively. A compound of the formula (I), a prodrug, thereof or a pharmaceutically acceptable salt of either which contains one or more of the above-mentioned isotopes and/or other isotopes of other atoms is intended to be part of the present invention. An isotope-labelled compound of the formula (I) can be used in a number of beneficial ways. For example, an isotope-labelled compound of the formula (I) into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula (I) has therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of the formula (I) can usually be prepared by carrying out the procedures disclosed in the synthesis schemes and the related description, in the example part and in the preparation part in the present text, replacing a non-isotope-labelled reactant by a readily available isotope-labelled reactant.

Deuterium ($^2H$) can also be incorporated into a compound of the formula (I) for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. If this rate difference is successfully applied to a compound of the formula (I) that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula (I) with improved stability through resistance to such oxidative metabolism. Significant improvements in the pharmacokinetic profiles of compounds of the formula (I) are thereby obtained, and can be expressed quantitatively in terms of increases in the in vivo half-life (t½), concentration at maximum therapeutic effect ($C_{max}$), area under the dose response curve (AUC), and F; and in terms of reduced clearance, dose and materials costs.

The following is intended to illustrate the above: a compound of the formula (I) which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula (I) can also be used to achieve a favourable modification of the metabolite spectrum of the starting compound in order to diminish or eliminate undesired toxic metabolites. For example, if a toxic metabolite arises through oxidative carbon-hydrogen (C H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The present invention relates to a pharmaceutical formulation (preferably for use in the treatment of an immunoregulatory abnormality or a cancer) comprising at least one compound of formula (I) (particularly a therapeutically effective amount of a compound of formula (I)), and/or a prodrug, solvate, tautomer, oligomer, adduct or stereoisomer thereof as well as a pharmaceutically acceptable salt of each of the foregoing, including mixtures thereof in all ratios, as active ingredient, together with a pharmaceutically acceptable carrier.

For the purpose of the present invention the term "pharmaceutical formulation" refers to a composition or product comprising one or more active ingredients, and one or more inert ingredients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical formulations of the present invention encompass any composition made by admixing at least one compound of the present invention and a pharmaceutically acceptable carrier, excipient or vehicle.

The pharmaceutical formulations of the present invention also encompass any composition that further comprises a second active ingredient and/or a prodrug or solvate thereof as well as a pharmaceutically acceptable salt of each of the foregoing, including mixtures thereof in all ratios, wherein that second active ingredient is other than a compound of formula (I) wherein all residues are defined above.

The pharmaceutical formulations according to the present invention can be used as medicaments in human and veterinary medicine.

For the purpose of the present invention an immunoregulatory abnormality is preferably an autoimmune or chronic inflammatory disease selected from the group consisting of: systemic lupus erythematosis, chronic rheumatoid arthritis, inflammatory bowel disease, multiple sclerosis, amyotrophic lateral sclerosis (ALS), atherosclerosis, scleroderma, autoimmune hepatitis, Sjogren Syndrome, lupus nephritis, glomerulonephritis, Rheumatoid Arthritis, Psoriasis, Myasthenia Gravis, Imunoglobuline A nephropathy, Vasculitis, Transplant rejection, Myositis, Henoch-Schonlein Purpura and asthma; cancer is preferably a hematological malignancy or a solid tumor, wherein the hematological malignancy is preferably a disease selected from the group of malignant B- and T/NK-cell non-Hodgkin lymphoma such as: multiple myeloma, mantle cell lymphoma, diffuse large B-cell lymphoma, plasmocytoma, follicular lymphoma, immunocytoma, acute lymphoblastic leukemia, chronic lymphocytic leukemia and myeloid leukemia; and wherein the solid tumor is preferably a disease selected from the group of: inflammatory breast, liver and colon cancer, lung cancer, head and neck cancer, prostate cancer, pancreas cancer, bladder cancer, renal cancer, hepatocellular cancer and gastric cancer.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medica-ment after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be formulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula (I) and salts, solvates and physiologically functional derivatives thereof and the other active ingredients can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula (I) and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropyl-methacrylamidophenol, polyhydroxyethylaspartamido-phenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or sus-pended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insuf-flators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

The compositions/formulations according to the invention can be used as medicaments in human and veterinary medicine.

A therapeutically effective amount of a compound of the formula (I) and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The invention further relates to a compound according to formula (I) or any specific embodiment described above and/or its prodrugs, solvates, tautomers, oligomers, adducts or stereoisomers thereof as well as the pharmaceutically acceptable salts of each of the foregoing, including mixtures thereof in all ratios, for use in the prevention and/or treatment of medical conditions that are affected by inhibiting LMP7.

The invention relates to a compound according to formula (I) or any specific embodiment described above and/or a prodrug, solvate, tautomers, oligomers, adducts or stereoisomers thereof as well as the pharmaceutically acceptable salts of each of the foregoing, including mixtures thereof in all ratios, for use in the treatment and/or prophylaxis (prevention) of an immunoregulatory abnormality or cancer (including in particular hematological malignancy and solid tumors).

The present invention furthermore relates to a method of treating a subject suffering from an immunoregulatory abnormality or a cancer, comprising administering to said subject a compounds of formula (I) in an amount that is effective for treating said immunoregulatory abnormality or a cancer. The present invention preferably relates to a method of treating a subject suffering from an autoimmune or chronic inflammatory disease, a hematological malignancy or a solid tumor.

The disclosed compounds of the formula (I) can be administered and/or used in combination with other known therapeutic agents (active ingredients), including anticancer agents. As used herein, the term "anticancer agent" relates to any agent which is administered to a patient with cancer for the purposes of treating the cancer.

The anti-cancer treatment defined above may be applied as a monotherapy or may involve, in addition to the herein disclosed compounds of formula (I), conventional surgery or radiotherapy or medicinal therapy. Such medicinal therapy, e.g. a chemotherapy or a targeted therapy, may include one or more, but preferably one, of the following anti-tumor agents:

Alkylating Agents
such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone;
apaziquone, fotemustine, glufosfamide, palifosfamide, pipobroman, trofosfamide, uramustine, TH-302[4], VAL-083[4];

Platinum Compounds
such as carboplatin, cisplatin, eptaplatin, miriplatine hydrate, oxaliplatin, lobaplatin, nedaplatin, picoplatin, satraplatin;

DNA Altering Agents
such as amrubicin, bisantrene, decitabine, mitoxantrone, procarbazine, trabectedin, clofarabine;
amsacrine, brostallicin, pixantrone, laromustine[1,3];

Topoisomerase Inhibitors
such as etoposide, irinotecan, razoxane, sobuzoxane, teniposide, topotecan; amonafide, belotecan, elliptinium acetate, voreloxin;

Microtubule Modifiers
such as cabazitaxel, docetaxel, eribulin, ixabepilone, paclitaxel, vinblastine, vincristine, vinorelbine, vindesine, vinflunine;
fosbretabulin, tesetaxel;

Antimetabolites
such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur; doxifluridine, elacytarabine, raltitrexed, sapacitabine, tegafur[2,3], trimetrexate;

Anticancer Antibiotics
such as bleomycin, dactinomycin, doxorubicin, epirubicin, idarubicin, levamisole, miltefosine, mitomycin C, romidepsin, streptozocin, vairubicin, zinostatin, zorubicin, daunurobicin, plicamycin; aclarubicin, peplomycin, pirarubicin;

Hormones/Antagonists
such as abarelix, abiraterone, bicalutamide, buserelin, calusterone, chlorotrianisene, degarelix, dexamethasone, estradiol, fluocortolone, fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol;
acolbifene, danazol, deslorelin, epitiostanol, orteronel, enzalutamide[1,3];

Aromatase Inhibitors such as aminoglutethimide, anastrozole, exemestane, fadrozole, letrozole, testolactone;

formestane;

Small Molecule Kinase Inhibitors such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib;

afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];

Photosensitizers such as methoxsalen[3];

porfimer sodium, talaporfin, temoporfin;

Antibodies such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3]; catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], nivolumab[1,3];

Cytokines such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates such as denileukin diftitox, ibritumomab tiuxetan, iobenguane I123, prednimustine, trastuzumab emtansine, estramustine, gemtuzumab, ozogamicin, aflibercept; cintredekin besudotox, edotreotide, inotuzumab ozogamicin, naptumomab estafenatox, oportuzumab monatox, technetium (99mTc) arcitumomab[1,3], vintafolide[3];

Vaccines such as sipuleuce[1,3]; vitespen[3], emepepimut-S[3], oncoVAX[4], rindopepimut[3], troVax[4], MGN-1601[4], MGN-1703[4];

Miscellaneous alitretinoin, bexarotene, bortezomib, everolimus, ibandronic acid, imiquimod, lenalidomide, lentinan, metirosine, mifamurtide, pamidronic acid, pegaspargase, pentostatin, sipuleuce[1,3], sizofiran, tamibarotene, temsirolimus, thalidomide, tretinoin, vismodegib, zoledronic acid, vorinostat; celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4];

[1]Prop. INN (Proposed International Nonproprietary Name)
[2]Rec. INN (Recommended International Nonproprietary Names)
[3]USAN (United States Adopted Name)
[4]no INN.

The invention furthermore relates to the use of compounds of formula (I), and related formulae in combination with at least one further medicament active ingredient, preferably medicaments used in the treatment of multiple sclerosis such as cladribine or another co-agent, such as interferon, e.g. pegylated or non-pegylated interferons, preferably interferon beta and/or with compounds improving vascular function or in combination with immunomodulating agents for example Fingolimod; cyclosporins, rapamycins or ascomycins, or their immunosuppressive analogs, e.g. cyclosporin A, cyclosporin G, FK-506, ABT-281, ASM981, rapamycin, 40-O-(2-hydroxy)ethyl-rapamycin etc.; corticosteroids; cyclophosphamide; azathioprene: methotrexate; leflunomide; mizoribine; mycophenolic add; mycophenolate mofetil; 15-deoxyspergualine; diflucortolone valerate; difluprednate; Alclometasone dipropionate; amcinonide; amsacrine; asparaginase; azathioprine; basiliximab; beclometasone dipropionate; betamethasone; betamethasone acetate; betamethasone dipropionate; betamethasone phosphate sodique; betamethasone valerate; budesonide; captopril; chlormethine chlorhydrate; cladribine; clobetasol propionate; cortisone acetate; cortivazol; cyclophosphamide; cytarabine; daclizumab; dactinomycine; desonide; desoximetasone; dexamethasone; dexamethasone acetate; dexamethasone isonicotinate; dexamethasone metasulfobenzoate sodique; dexamethasone phosphate; dexamethasone tebutate; dichlorisone acetate; doxorubicine chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone, hydrocortisone acetate, hydrocortisone butyrate, hydrocortisone hemisuccinate; melphalan; meprednisone; mercaptopurine; methylprednisolone; methylprednisolone acetate; methylprednisolone hemisuccinate; misoprostol; muromonab-cd3; mycophenolate mofetil; paramethasone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; teriflunomide; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD25, CD28, B7, CD40, CD45 or CD58 or their ligands; or other immunomodulatory compounds, e.g. CTLA4lg, or other adhesion molecule inhibitors, e.g. mAbs or low molecular weight inhibitors including Selectin antagonists and VLA-4 antagonists. A preferred composition is with Cyclosporin A, FK506, rapamycin or 40-(2-hydroxy)ethyl-rapamycin and Fingolimod. These further medicaments, such as interferon beta, may be administered concomitantly or sequentially, e.g. by subcutaneous, intramuscular or oral routes.

The invention furthermore relates to the use of compounds of formula (I), and related formulae in combination with at least one further medicament active ingredient, preferably medicaments used in the treatment of cancer (such as in particular the anticancer and/or antitumor agents described above).

The present invention further relates to a set (kit) consisting of separate packs of (a) an effective amount of a compound of the formula (I) and/or a prodrug, solvate, tautomer, oligomer, adduct or stereoisomer thereof as well as a pharmaceutically acceptable salt of each of the foregoing, including mixtures thereof in all ratios,
and
(b) an effective amount of a further medicament active ingredient.

The compounds of the present invention can be prepared according to the procedures of the following Schemes and Examples, using appropriate materials, and are further exemplified by the following specific examples.

Moreover, by utilizing the procedures described herein, in conjunction with ordinary skills in the art, additional compounds of the present invention claimed herein can be readily prepared. The compounds illustrated in the examples are not, however, to be construed as forming the only genus that is considered as the invention. The examples further illustrate details for the preparation of the compounds of the present invention. Those skilled in the art will readily understand that known variations of the conditions and processes of the following preparative procedures can be used to prepare these compounds.

The starting materials for the preparation of compounds of the present invention can prepared by methods as described in the examples or by methods known per se, as described in the literature of synthetic organic chemistry and known to the skilled artisan, or can be obtained commercially.

The synthesis of compounds of formula (IV) is described in WO 2016/050356, WO 2016/050355, WO 2016/050359, and WO 2016/050358.

Examples
LCMS:
Method A: Agilent 70108359—Chromolith Speed Rod RP18e 50-4.6 mm; polar.m; 2.4 mL/min; 220 nm; buffer A: 0.05% HCOOH/H$_2$O, buffer B: 0.04% HCOOH/ACN; 0.0-2.8 min 4%-100% buffer B; 2.8-3.3 min 100% buffer B; 3.3-3.4 min 100%-4% buffer B.

Method B: Waters XBrigde C8 3.5 μm; 4.6×50 mm; EliteLa Chrom 70173815; 8.1 min; 2 ml/min; 215 nm; buffer A: 0.05% TFA/H$_2$O; buffer B: 0.04% TFA/ACN; 0.0-0.2 min 5% buffer B; 0.2-8.5 min 5%-100% buffer B; 8.5-10.0 min 99%-5% buffer.

RT: Retention rime.

The invention will be illustrated, but not limited, by reference to the specific embodiments described in the following examples. Unless otherwise indicated in the schemes, the variables have the same meaning as described above.

Unless otherwise specified, all starting materials are obtained from commercial suppliers and used without further purifications. Unless otherwise specified, all temperatures are expressed in ° C. and all reactions are conducted at rt. Compounds can be purified by common means such as in particular silica chromatography or preparative HPLC.

Unless stated otherwise all structures indicated below, where no specific stereochemistry is indicated, refer to mixtures of the stereoisomers.

Intermediate 1

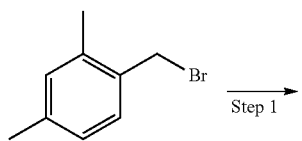

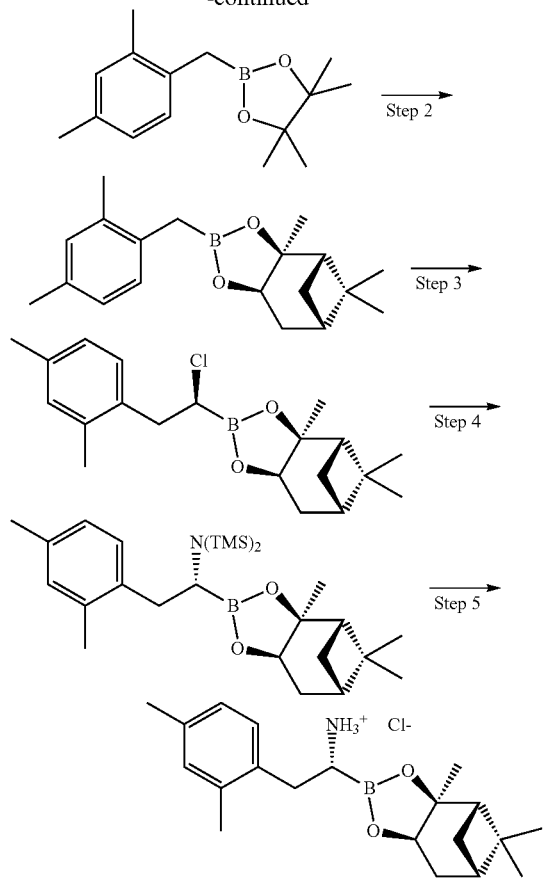

Step 1: 2-(2,4-Dimethyl-benzyl)-4,4,5,5-tetramethyl-[1,3,2]dioxaborolane

To a solution of 1-Bromomethyl-2,4-dimethyl-benzene (25.00 g; 114.40 mmol; 1.00 eq.) in degased Dioxane (250.00 ml), Bis(pinacolato)diboron (35.21 g; 137.28 mmol; 1.20 eq.), dried K$_2$CO$_3$ (47.91 g; 343.19 mmol; 3.00 eq.) and Tetrakis(triphenylphosphine)palladium(0) (6623 mg; 5.72 mmol; 0.05 eq.) are added. The reaction mixture is then heated at 100° C. under nitrogen atmosphere for 16 h. The reaction mixture is diluted with dichloromethane and passed through celite. The filtrate is concentrated. The residue is dissolved in ethyl acetate and washed with brine. The organic layer is dried over anhydrous Na$_2$SO$_4$, filtered and concentrated. The crude is purified by column chromatography using 1% ethyl acetate in petroleum ether to get 2-(2,4-Dimethyl-benzyl)-4,4,5,5-tetramethyl-[1,3,2]dioxaborolane (11.50 g; 37.84 mmol; 33.1%) as colorless liquid.
$^1$H NMR (400 MHz, CDCl$_3$) δ 7.04-7.02 (m, 1H), 6.95-6.93 (m, 1H), 6.92-6.90 (m, 1H), 2.28 (s, 3H), 2.25 (s, 3H), 2.23 (s, 2H), 1.24 (s, 12H).

Step 2: (1S,2S,6R,8S)-4-(2,4-Dimethyl-benzyl)-2,9,9-Dimethyl-3,5-dioxa-4-bora-tricyclo[6.1.1.0$^{2,6}$]decane To an ice-cooled solution of 2-(2,4-Dimethyl-benzyl)-4,4,5,5-tetramethyl-[1,3,2]dioxaborolane (24.00 g; 79.3 mmol; 1.0 eq.) in Diethyl ether (240.00 ml) under nitrogen atmosphere, (1S,2S,3R,5S)-2,6,6-Trimethyl-bicyclo[3.1.1]

heptane-2,3-diol (20.68 g; 119.07 mmol; 1.50 eq.) is added and the reaction mixture is stirred at rt for 14 h. TLC analysis showed completion of reaction. The reaction mixture is washed with brine. The organic layer is dried over anhydrous $Na_2SO_4$ and concentrated. The crude is purified by flash column chromatography using 2% ethyl acetate in petroleum ether to get (1S,2S,6R,8S)-4-(2,4-Dimethyl-benzyl)-2,9,9-trimethyl-3,5-dioxa-4-bora-tricyclo[6.1.1.0$^{2,6}$]decane (28.00 g; 82.96 mmol; 90.0%) as colorless oil.

$^1$H NMR (400 MHz, CDCl$_3$): δ 7.05-7.03 (m, 1H), 6.95-6.94 (m, 1H), 6.92-6.90 (m, 1H), 4.27-4.25 (m, 1H), 2.33-2.30 (m, 9H), 2.27-2.17 (m, 1H), 2.05 (t, J=5.76 Hz, 1H), 1.90-1.89 (m, 1H), 1.84-1.80 (m, 1H), 1.38 (s, 3H), 1.28 (s, 3H), 1.11-1.09 (m, 1H), 0.91 (s, 3H)

GCMS: m/z: 298.3.

Step 3: (1S,2S,6R,8S)-4-[(S)-1-Chloro-2-(2,4-dimethyl-phenyl)-ethyl]-2,9,9-timethyl-3,5-dioxa-4-bora-tricyclo[6.1.1.0$^{2,6}$]decane Dichloromethane (37.33 ml; 583.45 mmol; 3.00 eq.) in Tetrahydrofuran (140.00 ml) is taken in a RB-flask (round bottom flask) under a positive pressure of nitrogen and cooled to −99° C. using liquid nitrogen-ethanol mixture. To this n-butyl lithium (1.6 M in THF) (133.71 ml; 213.93 mmol) is added dropwise through the sides of the RB-flask (at a medium rate, addition took about 35 min.) so that the internal temperature is maintained between −92° C. and −102° C. After addition, the reaction mixture is stirred for 25 minutes. During the course of the reaction a white precipitate is formed (The internal temperature is maintained between −90° C. and −96° C.). Then a solution of (1S,2S,6R,8S)-4-(2,4-Dimethyl-benzyl)-2,9,9-trimethyl-3,5-dioxa-4-bora-tricyclo[6.1.1.0$^{2,6}$]decane (58.00 g; 194.5 mmol) in THF (300.00 ml) is added dropwise through the sides of the RB-flask (about 40 min) so that the internal temperature is maintained between −94° C. and 100° C. After addition the reaction mixture is stirred for 10 min. Then zinc chloride (0.5 M in THF) (388.97 ml; 194.48 mmol) is added dropwise through the sides of the RB-flask (at a medium rate, addition took about 35 min.) so that the internal temperature is maintained between −94° C. and −99° C. The reaction mixture is then slowly allowed to reach 20° C. and stirred at 20° C. for 2.5 h. An aliquot of the reaction mixture is worked-up and analysed by $^1$H NMR which showed the completion of reaction. The reaction mixture is concentrated (temperature of the bath 30° C.). The residue is partitioned between diethyl ether and saturated NH$_4$Cl solution. The organic layer is dried over anhydrous Na$_2$SO$_4$ and concentrated (temperature of bath 30° C.) to afford (1S,2S,6R,8S)-4-[(S)-1-Chloro-2-(2,4-dimethyl-phenyl)-ethyl]-2,9,9-trimethyl-3,5-dioxa-4-bore-tricyclo[6.1.1.0$^{2,6}$]decane (75.70 g; 154.83 mmol; 79.6%) as white solid.

$^1$H NMR (400 MHz, CDCl$_3$): □ 7.12 (d, J=7.64 Hz, 1H), 6.98 (s, 1H), 6.96 (d, J=7.68 Hz, 1H), 4.38-4.36 (m, 1H), 3.67-3.62 (m, 1H), 3.18-3.11 (m, 2H), 2.40-2.36 (m, 2H), 2.32 (s, 3H), 2.30 (s, 3H), 2.23-2.20 (m, 1H), 2.08 (t, J=5.96 Hz, 1H), 1.93-1.87 (m, 2H), 1.36 (s, 3H), 1.30 (s, 3H), 1.14-1.11 (m, 1H), 0.84 (s, 3H). 7.18-7.08 (m, 5H), 4.37 (dd, J=1.32, 8.74 Hz, 1H), 3.77-3.75 (m, 1H), 3.67-3.63 (m, 1H), 3.19-3.17 (m, 1H), 3.10-3.08 (m, 1H), 2.36-2.31 (m, 5H), 2.09 (t, J=5.84 Hz, 1H), 1.93-1.86 (m, 4H), 1.39 (s, 3H), 1.30 (s, 3H), 1.13-1.10 (m, 1H), 0.84 (s, 3H).

GCMS: m/z: 346.3.

Step 4: (1S,2S,6R,8S)-4-[(R)-2-(2,4-Dimethyl-phenyl)-1-(1,1,1,3,3,3-hexamethyl-disilazan-2-yl)-ethyl]-2,9,9-trimethyl-3,5-dioxa-4-bora-tricyclo[6.1.1.0$^{2,6}$]decane A solution of (1S,2S,6R,8S)-4-[(S)-1-Chloro-2-(2,4-dimethyl-phenyl)-ethyl]-2,9,9-trimethyl-3,5-dioxa-4-bora-tricyclo[6.1.1.0$^{2,6}$]decane (75.70 g; 218.35 mmol; 1.00 eq.) in THF (400.00 ml) under a positive pressure of nitrogen atmosphere is cooled to −78° C. To this a solution of Lithium (bistrimethylsilyl)amide (1.0 M in THF) (262 ml; 262 mmol; 1.20 eq.) is added dropwise over a period of 30 minutes. The reaction mixture is allowed to attain rt and stirred at rt for 18 h. The reaction mixture is evaporated at a temperature 30° C. The residue is triturated with hexane and the solid formed is filtered. The filtrate is allowed to stand for some time under vacuum and any solid if formed is filtered again. The filtrate is concentrated at a temperature 30° C. to get (1S,2S,6R,8S)-4-[(R)-2-(2,4-Dimethyl-phenyl)-1-(1,1,1,3,3,3-hexamethyl-disilazan-2-yl)-ethyl]-2,9,9-trimethyl-3,5-dioxa-4-bora-tricyclo[6.1.1.0$^{2,6}$]decane (80.10 g; 169.84 mmol; 77.8%; brown oil).

$^1$H NMR (400 MHz, CDCl$_3$): δ: 7.06 (d, J=7.64 Hz, 1H), 6.94 (s, 1H), 6.90 (d, J=7.80 Hz, 1H), 4.29-4.27 (m, 1H), 3.15-3.10 (m, 1H), 2.87-2.83 (m, 1H), 2.58-2.53 (m, 1H), 2.34-2.32 (m, 2H), 2.30 (s, 3H), 2.28 (s, 3H), 2.15-2.13 (m, 1H), 2.03 (t, J=5.88 Hz, 1H), 1.90-1.88 (m, 1H), 1.81-1.77 (m, 1H), 1.39 (s, 3H), 1.32 (s, 3H), 1.01-0.98 (m, 1H), 0.93 (s, 3H), 0.85 (s, 3H), 0.09 (s, 18H).

Step 5: (R)-2-(2,4-Dimethyl-phenyl)-1-((1S,2S,6R,8S)-2,9,9-trimethyl-3,5-dioxa-4-bora-tricyclo[6.1.1.0$^{2,6}$]dec-4-yl)-ethylamine Hydrochloride A stirred solution of (1S,2S,6R,8S)-4-[(R)-2-(2,4-Dimethyl-phenyl)-1-(1,1,1,3,3,3-hexamethyl-disilazan-2-yl)-ethyl]-2,9,9-timethyl-3,5-dioxa-4-bora-tricyclo[6.1.1.0$^{2,5}$]decane (80.10 g; 169.84 mmol; 1.00 eq.) in diethyl ether (400.00 ml) under nitrogen atmosphere is cooled to −10° C. To this 2M solution of Hydrochloric acid in diethylether (212.30 ml; 424.59 mmol; 2.50 eq.) is added dropwise. The reaction mixture is stirred at rt for 2 h. The reaction mixture is evaporated under reduced pressure to get (R)-2-(2,4-Dimethyl-phenyl)-1-((1S,2S,6R,8S)-2,9,9-timethyl-3,5-dioxa-4-bora-tricyclo[6.1.1.0$^{2,6}$]dec-4-yl)-ethylamine hydrochloride (63.00 g; 72.61 mmol; 42.8%; brown solid).

$^1$H NMR (400 MHz, DMSO-d6): δ 8.19 (s, 3H), 7.05 (d, J=7.68 Hz, 1H), 6.95 (s, 1H), 6.90 (d, J=8.16 Hz, 1H), 4.31 (dd, J=1.80, 8.76 Hz, 1H), 3.02-3.00 (m, 1H), 2.99-2.92 (m, 1H), 2.87-2.84 (m, 1H), 2.26-2.24 (m, 3H), 2.26 (s, 3H), 2.24 (s, 3H), 2.03-2.00 (m, 1H), 1.91 (t, J=5.68 Hz, 1H), 1.82-1.80 (m, 1H), 1.71-1.66 (m, 1H), 1.31 (s, 3H), 1.21 (s, 3H), 0.98-0.96 (m, 1H), 0.77 (s, 3H).

By similar sequences described for intermediate 1 the following compounds can be prepared

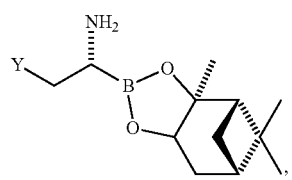

wherein the group Y denotes one of the following groups:

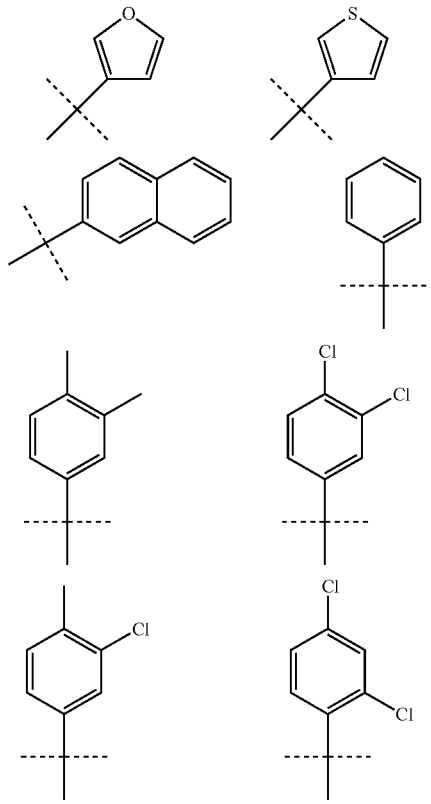

Intermediate 2

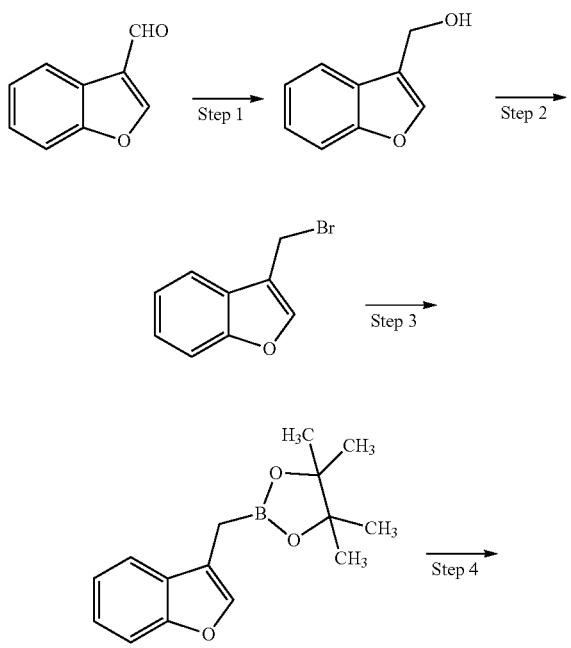

-continued

Step 5

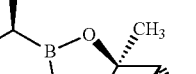

Step 6

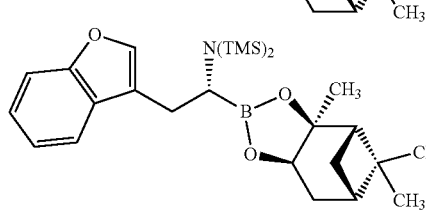

Step 7

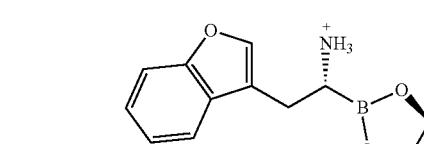

Step 1: Benzofuran-3-ylmethanol

A solution of 1-Benzofuran-3-carbaldehyde (5 g, 34.2 mmol) in methanol (50 mL) is cooled with ice and sodium borohydride (1.9 g, 51.3 mmol) is added portionwise. The reaction mixture is stirred at room temperature for 1 h. The reaction mixture is concentrated and the residue is partitioned between saturated ammonium chloride and ethylacetate. The organic layer is separated, dried over sodium sulfate and concentrated (5.0 g, colourless liquid, 98%).
$^1$H NMR (400 MHz, CDCl$_3$): δ 7.70-7.68 (m, 1H), 7.62 (s, 1H), 7.52-7.50 (m, 1H), 7.36-7.26 (m, 2H), 4.86 (s, 2H).

Step 2: 3-(bromomethyl)benzofuran

A cold (0° C.) solution of benzofuran-3-ylmethanol (5.0 g, 33.7 mmol) in diethyl ether (50 mL) is treated with phosphorus tribromide (1.1 mL, 11.2 mmol) and the reaction mixture is stirred at 0° C. for 30 min. The reaction mixture is then poured into ice and extracted with ether. The organic layer is dried over sodium sulfate and concentrated (7.1 g, yellow liquid, 100%).
$^1$H NMR (400 MHz, CDCl$_3$): δ 7.74-7.71 (m, 2H), 7.53 (s, 1H), 7.39-7.31 (m, 2H), 4.65 (s, 2H).

Step 3: 2-(benzofuran-3-ylmethyl)-4,4,5,5-tetramethyl-1,3,2-dioxaborolane

A solution of 3-(bromomethyl)benzofuran (7.1 g, 33.8 mmol) in degassed 1,4-dioxane (70 ml) is treated with bis(pinacolato)diboron (10.3 g, 40.5 mmol), potassium carbonate (13.9 g, 101.0 mmol), tetrakis(triphenylphosphine)palladium(0) (1.9 g, 1.7 mmol) and the mixture heated at 100° C. for 12 h The contents of the flask are cooled to room temperature and filtered through a celite bed. Filtrate is concentrated and the crude is purified by flash column chromatography on silica gel, eluting with 2-5% of ethylacetate in petroleum ether to get the title compound (6.1 g, 69%) as yellow oil.

$^1$H NMR (400 MHz, CDCl$_3$) b 7.57-7.52 (m, 2H), 7.46-7.44 (m, 1H), 7.30-7.21 (m, 2H), 2.23 (s, 2H), 1.29 (s, 12H).

Step 4: 2-(benzofuran-3-ylmethyl)boronic Acid (+)-pinanediol Ester

A solution of 2-(benzofuran-3-ylmethyl)-4,4,5,5-tetramethyl-1,3,2-dioxaborolane (6.1 g, 23.6 mmol) in diethyl ether (60 ml) is treated with (1S,2S, 3R, 5S)-(+)-pinanediol (6.0 g, 35.4 mmol). The reaction mixture is stirred at room temperature for 12 h then the mixture is washed with water twice, then with brine and dried over anhydrous sodium sulphate, then concentrated. The crude product is purified by flash column chromatography on silica gel, eluting with 5% of ethyl acetate in petroleum ether, to afford the title compound (6.3 g. 82%).

$^1$H NMR (400 MHz, CDCl$_3$): δ 7.58-7.56 (m, 1H), 7.55-7.53 (m, 1H), 7.46-7.44 (m, 1H), 7.28-7.23 (m, 2H), 4.33 (dd, J=1.88, 8.76 Hz, 1H), 2.34-2.32 (m, 1H), 2.28 (s, 2H), 2.22-2.21 (m, 1H), 2.08 (t, J=5.88 Hz, 1H), 1.42 (s, 3H), 1.29 (s, 3H), 1.13 (d, J=10.92 Hz, 1H), 0.85 (s, 3H). GCMS: m/z: 310.

Step 5: [(1S)-1-chloro-2-(benzofuran-3-ylmethyl) boronic Acid (+)-pinanediol Ester To a cooled (−100° C.) mixture of dichloromethane (6.3 ml, 60.9 mmol) and anhydrous tetrahydrofuran (36 ml) is added n-butyl lithium (1.6 M in hexanes, 14.0 ml, (22.3 mmol) over 20 min. After stirring for 20 min. at −100° C., a solution of 2-(benzofuran-3-ylmethyl)boronic acid (+)-pinanediol ester (6.3 g, 20.3 mmol) in anhydrous THF (22 ml) is added over 20 min. Then a solution of zinc chloride (0.5 M in THF, 36.5 mL, 18.2 mmol) is added at 100° C. over 30 min. The mixture is allowed to reach room temperature and stirred for 18 h and concentrated. To the resulting oil is added diethyl ether and saturated ammonium chloride. The organic layer is dried over anhydrous sodium sulphate and concentrated in vacuo (residue: 7.3 g, 99%).

$^1$H NMR (400 MHz, DMSO-d6): δ 7.60-7.57 (m, 2H), 7.49-7.47 (m, 1H), 7.31-7.25 (m, 2H), 4.36-4.34 (m, 1H), 3.31-3.29 (m, 1H), 3.24-3.22 (m, 1H), 2.35-2.31 (m, 1H), 2.14-2.12 (m, 1H), 2.06 (t, J=5.84 Hz, 1H), 1.90-1.86 (m, 2H), 1.42 (s, 3H), 1.04 (d, J=11.04 Hz, 1H), 0.85 (s, 3H). GCMS: m/z: 358.2.

Step 6: [(1R)-1-[bis(trimethylsilyl)amino]-2-(benzofuran-3-ylmethyl) Boronic Acid (+)-pinanediol Ester To a cooled (−78° C.) solution of [(1S)-1-chloro-2-(benzofuran-3-ylmethyl)boronic acid (+)-pinanediol ester (7.3 g, 20.3 mmol) in 40 ml of anhydrous tetrahydrofuran is added lithium bis(trimethylsilyl)amide (1M in THF, 25.5 ml, 25.5 mmol). The mixture is allowed to room temperature, stirred for 18 h and concentrated to dryness. To the resulting residue is added hexane, and then the precipitated solid is filtered off. The filtrate is concentrated to give the required crude product (6.7 g, 68%).

$^1$H NMR (400 MHz, CDCl$_3$): δ 7.60-7.59 (m, 1H), 7.50-7.45 (m, 2H), 7.28-7.24 (m, 2H), 4.31 (dd, J=1.56, 8.70 Hz, 1H), 3.18-3.14 (m, 1H), 2.92-2.90 (m, 1H), 2.75-2.72 (m, 1H), 2.34-2.30 (m, 1H), 2.15-2.14 (m, 1H), 2.03 (t, J=5.68 Hz, 1H), 1.88-1.80 (m, 2H), 1.39 (s, 3H), 1.30 (s, 3H), 1.01 (d, J=10.88 Hz, 1H), 0.84 (s, 3H), 0.09 (s, 18H).

Step 7: [(1R)-1-amino-2-(benzofuran-3-ylmethyl) boronic Acid (+)-pinanediol Ester Trifluroacetate A cooled (0° C.) solution of [(1R)-1-[bis(trimethylsilyl)amino]-2-(benzofuran-3-ylmethyl)boronic acid (+)-pinanediol ester (6.7 g, 13.9 mmol) in diethyl ether (30 ml) is treated with trifluoroacetic acid (3.2 ml, 41.7 mmol) dropwise. The reaction mixture is then stirred at rt for 3 h. Precipitation is seen. The reaction mixture is cooled to 0° C. and filtered. The filtered solid is washed with cold ether and dried under vacuum to afford the title compound (2.3 g, white solid, 36%).

$^1$H NMR (400 MHz, DMSO-d$_6$): δ 7.66 (s, 1H), 7.61-7.60 (m, 1H), 7.47-7.45 (m, 1H), 7.29-7.20 (m, 2H), 4.30-4.28 (m, 1H), 3.27-3.16 (m, 3H), 2.25-2.13 (m, 3H), 1.94 (t, J=5.56 Hz, 1H), 1.86-1.81 (m, 2H), 1.25 (s, 6H), 1.01 (d, J=8.00 Hz, 1H), 0.75 (s, 3H).

Intermediate 3: 2-(7-Methyl-benzofuran-3-yl)-1-((1S,2S,6R,8S)-2,9,9-trimethyl-3,5-dioxa-4-boratricyclo[6.1.1.0$^{2,6}$]dec-4-yl)-ethylamine Hydrochloride

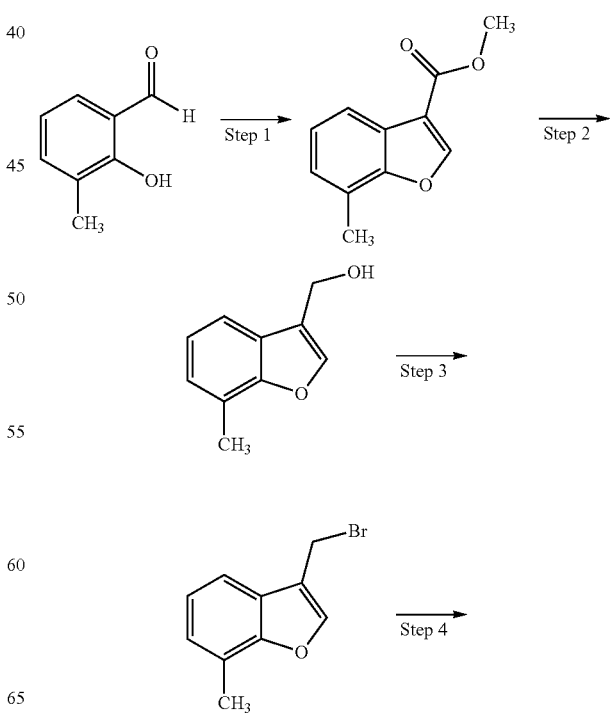

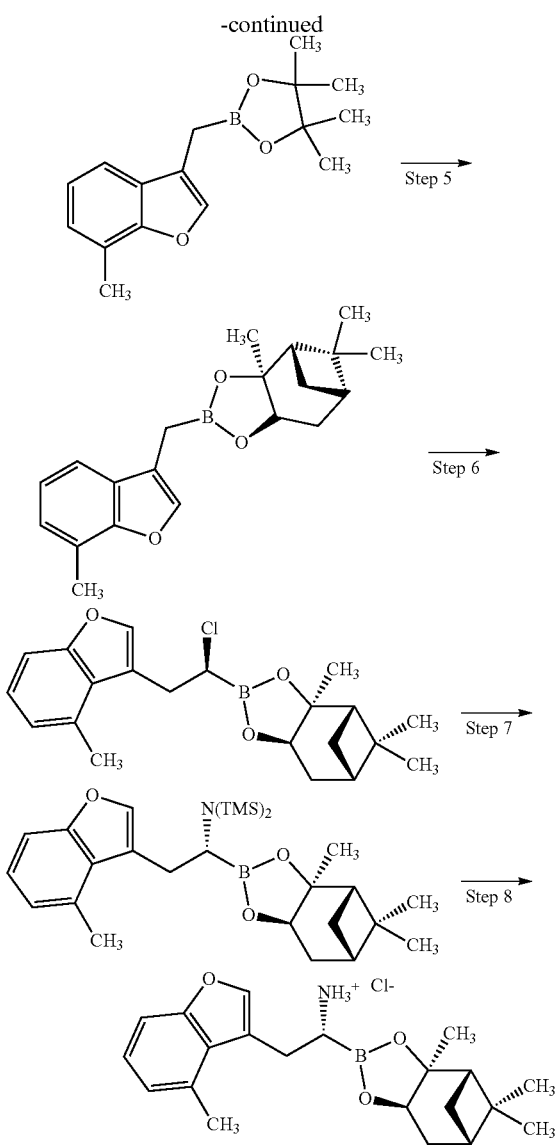

Step 1: 7-Methyl-benzofuran-3-carboxylic Acid Ethyl Ester

To a solution of 2-Hydroxy-3-methyl-benzaldehyde (20.00 g; 139.55 mmol; 1.00 eq.) in dichloromethane (120 mL) is added Tetrafluoroboric acid diethylether complex (1.88 ml; 13.96 mmol; 0.10 eq.). To the resulting dark red mixture, Ethyldiazoacetate (31.70 ml; 300.04 mmol; 2.15 eq.) in dichloromethane (80 mL) is added drop wise slowly at 25-30° C. (internal temperature) for about 50 min. After 16 h, concentrated $H_2SO_4$ is added. The reaction mixture is stirred for 30 min. The reaction mixture is then neutralized with solid $NaHCO_3$, filtered through celite and the filtrate is concentrated to get a crude residue. The residue is purified by column chromatography using 2% ethyl acetate in petroleum ether to afford 7-Methyl-benzofuran-3-carboxylic acid ethyl ester (19.00 g; 86.83 mmol; 62.2%; yellow oil).

HPLC (method A): RT 4.98 min (HPLC purity 93%)

$^1$H NMR, 400 MHz, $CDCl_3$: 8.27 (s, 1H), 7.88-7.90 (m, 1H), 7.25-7.29 (m, 1H), 7.17 (d, J=7.32 Hz, 1H), 4.39-4.45 (m, 2H), 2.55 (s, 3H), 1.44 (t, J=7.16 Hz, 3H).

Step 2: (7-Methyl-benzofuran-3-yl)-methanol

To a solution of 7-Methyl-benzofuran-3-carboxylic acid ethyl ester (19.00 g; 86.83 mmol; 1.00 eq.) in Dichloromethane (190.00 ml) under nitrogen is added Diisobutyl Aluminium Hydride (1.0 M in Toluene) (191.03 ml; 191.03 mmol; 2.20 eq.) drop wise at −78° C. The reaction mixture is allowed to come to rt and stirred for 1 h. The reaction mixture is cooled with ice bath and quenched with an aqueous solution of 1.5N HCl. The resultant mixture (which had sticky solid mass suspended in solvent) is diluted with ethylacetate and filtered through celite. The celite bed is washed thoroughly with ethylacetate and dichloromethane. The filtrate is evaporated to get a crude residue. The solid which remained in the celite bed is taken and triturated with ethylacetate and filtered. The filtrate is mixed together with the crude residue and evaporated. The residue thus obtained is taken in ethylacetate and washed with an aqueous solution of 1.5 N HCl and brine. The organic layer is dried over anhydrous $Na_2SO_4$ and concentrated. The residue obtained is purified by flash column chromatography using 40-50% ethyl acetate in petroleum ether as eluent to get (7-Methyl-benzofuran-3-yl)-methanol (8.20 g; 48.40 mmol; 55.7%; light yellow oil).

HPLC (method A): RT 3.33 min., (HPLC purity 95.7%).

$^1$H NMR, 400 MHz, $CDCl_3$: 7.64 (s, 1H), 7.50-7.52 (m, 1H), 7.17-7.21 (m, 1H), 7.14 (d, J=7.20 Hz, 1H), 4.86-4.86 (m, 2H), 2.54 (s, 3H).

Step 3: 3-(bromomethyl)-7-methyl-benzofuran

To an ice-cooled solution of (7-Methyl-benzofuran-3-yl)-methanol (8.20 g; 48.40 mmol; 1.00 eq.) in Diethyl ether (82.00 ml) under nitrogen atmosphere is added phosphorus tribromide (1.53 ml; 16.12 mmol; 0.33 eq.) drop wise and the reaction mixture is stirred at ice cold condition for 30 minutes. The reaction mixture is poured into ice and extracted with diethyl ether. The organic layer is dried over anhydrous $Na_2SO_4$ and concentrated to afford 3-Bromomethyl-7-methyl-benzofuran (10.00 g; 44.43 mmol; 91.8%; colorless oil).

$^1$H NMR, 400 MHz, $CDCl_3$: 7.71 (s, 1H), 7.53-7.55 (m, 1H), 7.21-7.25 (m, 1H), 7.16 (d, J=7.32 Hz, 1H), 4.65 (s, 2H), 2.48 (s, 3H).

Step 4: 7-Methyl-3-(4,4,5,5-tetramethyl-[1,3,2]dioxaborolan-2-ylmethyl)-benzofuran To a solution of 3-Bromomethyl-7-methyl-benzofuran (10.00 g; 44.43 mmol; 1.00 eq.) in degased Dioxane-1,4 (100.00 ml) are added Bis(pinacolato)diboron (13.68 g; 53.31 mmol; 1.20 eq.), dried $K_2CO_3$ (18.61 g; 133.28 mmol: 3.00 eq.) and tetrakis(triphenylphosphine)palladium(0) (2.57 g; 2.22 mmol; 0.05 eq.). The reaction mixture is then heated at 100° C. under nitrogen atmosphere for 16 h. The reaction mixture is diluted with dichloromethane and filtered through celite. The filtrate is concentrated. The residue is dissolved in ethyl acetate and washed with brine. The organic layer is dried over anhydrous $Na_2SO_4$ and concentrated. The crude is purified by column chromatography using 2% ethyl acetate in petroleum ether to get 7-Methyl-3-(4,4,5,5-tetramethyl-[1,3,2]dioxaborolan-2-ylmethyl)-benzofuran (5.00 g; 18.37 mmol; 41.4%; colorless liquid).

$^1$H NMR, 400 MHz, DMSO-d6: 7.65 (s, 1H), 7.33-7.35 (m, 1H), 7.07-7.13 (m, 2H), 2.43 (s, 3H), 2.13 (s, 2H), 1.16 (s, 12H).

Step 5: Trimethyl-4-(7-methyl-benzofuran-3-ylmethyl)-3,5-dioxa-4-bora-tricyclo[6.1.1.0$^{2,6}$]decane To an ice-cooled solution of 7-Methyl-3-(4,4,5,5-tetramethyl-[1,3,2]dioxaborolan-2-ylmethyl)-benzofuran (5.00 g; 18.37 mmol; 1.00 eq.) in Et$_2$O (50.00 ml) under nitrogen atmosphere is added 1S, 2S, 3R, 5S-(+)-2,3-pinane diol (4.69 g; 27.56 mmol; 1.50 eq.) and the reaction mixture is stirred at rt for 14 h. TLC analysis showed completion of reaction. The reaction mixture is washed with brine. The organic layer is dried over anhydrous Na$_2$SO$_4$ and concentrated. The crude is purified by flash column chromatography using 2% ethyl acetate in petroleum ether to get (1S, 2S,6R,8S)-2,9,9-Trimethyl-4-(7-methyl-benzofuran-3-ylmethyl)-3,5-dioxa-4-bora-tricyclo[6.1.1.0$^{2,6}$]decane (5.00 g; 13.00 mmol; 70.7%; colorless liquid).

GCMS: m/z: 324.2

$^1$H NMR, 400 MHz, CDCl$_3$: 7.53-7.55 (m, 1H), 7.39-7.40 (m, 1H), 7.12-7.27 (m, 1H), 7.06-7.08 (m, 1H), 4.31-4.34 (m, 1H), 2.53 (s, 3H), 2.30-2.37 (m, 1H), 2.26 (s, 2H), 2.18-2.23 (m, 1H), 2.07 (t, J=5.76 Hz, 1H), 1.84-1.93 (m, 2H), 1.42 (s, 3H), 1.29 (s, 3H), 1.12-1.15 (m, 1H), 0.85 (s, 3H).

Step 6: (1S,2S,6R,8S)-4-[1-Chloro-2-(7-methyl-benzofuran-3-yl)-ethyl]-2,9,9-trimethyl-3,5-dioxa-4-bora-tricyclo[6.1.1.0$^{2,6}$]decane Dichloromethane (2.96 ml; 46.26 mmol; 3.00 eq.) in THF (40 mL) is taken in a RB-flask under a positive pressure of nitrogen and cooled to −95° C. using liquid nitrogen-ethanol mixture. To this n-butyl lithium (1.6 M in hexanes) (10.60 ml; 16.96 mmol; 1.10 eq.) is added drop wise through the sides of the RB-flask (at a medium rate, addition took about 30 min.) so that the internal temperature is maintained between −95° C. and −100° C. After addition, the reaction mixture is stirred for 20 minutes. During the course of the reaction a white precipitate is formed (The internal temperature is maintained between −95° C. and −100° C.). Then a solution of (1S,2S,6R,8S)-2,9,9-Trimethyl-4-(7-methyl-benzofuran-3-yl methyl)-3,5-dioxa-4-bora-tricyclo[6.1.1.0$^{2,6}$]decane (5.00 g; 15.42 mmol; 1.00 eq.) in THF (20 mL) is added drop wise through the sides of the RB-flask (about 25 min) so that the internal temperature is maintained between −95° C. and −100° C. After addition, immediately zinc chloride (0.5 M in THF) (27.76 ml; 13.88 mmol; 0.90 eq.) is added drop wise through the sides of the RB-flask (at a medium rate, addition took about 45 min.) so that the internal temperature is maintained between −95° C. and −100° C. The reaction mixture is then slowly allowed to attain rt and stirred at rt for 16 h. The reaction mixture is concentrated (temperature of the bath 30° C.). The residue is partitioned between diethylether and saturated NH$_4$Cl solution. The organic layer is separated, dried over anhydrous Na$_2$SO$_4$ and concentrated (temperature of bath 30° C.) to afford (1S,2S,6R,8S)-4-[1-Chloro-2-(7-methyl-benzofuran-3-yl)-ethyl]-2,9,9-trimethyl-3,5-dioxa-4-bora-tricyclo[6.1.1.0$^{2,6}$]decane (5.90 g; 15.83 mmol; 102.7%; brown liquid).

$^1$H NMR, 400 MHz, CDCl$_3$: 7.57 (s, 1H), 7.42-7.44 (m, 1H), 7.27 (s, 1H), 7.09-7.18 (m, 1H), 4.34-4.36 (m, 1H), 3.74-3.76 (m, 1H), 3.28-3.30 (m, 1H), 3.20-3.22 (m, 1H), 2.52 (s, 3H), 2.32-2.34 (m, 1H), 2.07 (t, J=5.88 Hz, 1H), 1.85-1.91 (m, 2H), 1.42 (s, 3H), 1.29 (s, 3H), 1.06-1.09 (m, 1H), 0.85 (s, 3H).

Step 7: ((1S,2S,6R,8S)-4-[1-(1,1,1,3,3,3-Hexamethyl-disilazan-2-yl)-2-(7-methyl-benzofuran-3-yl)-ethyl]-2,9,9-trimethyl-3,5-dioxa-4-bora-tricyclo[6.1.1.0$^{2,6}$]decane A solution of (1S,2S,6R,8S)-4-[1-Chloro-2-(7-methyl-benzofuran-3-yl)-ethyl]-2,9,9-trimethyl-3,5-dioxa-4-bora-tricyclo[6.1.1.0$^{2,6}$]decane (5.90 g; 15.83 mmol; 1.00 eq.) in THF (40.00 ml) under a positive pressure of nitrogen atmosphere is cooled to −78° C. To this a solution of lithium (bistrimethylsilyl)amide (1.0 M in THF) (17.41 ml; 17.41 mmol; 1.10 eq.) is added drop wise over a period of 30 minutes. The reaction mixture is allowed to attain rt and stirred at rt for 18 h. The reaction mixture is evaporated at 30° C. The residue is triturated with n-hexane and the solid formed is filtered. The filtrate is concentrated at 30° C. to get (1S,2S,6R,8S)-4-[1-(1,1,1,3,3,3-Hexamethyl-disilazan-2-yl)-2-(7-methyl-benzofuran-3-yl)-ethyl]-2,9,9-trimethyl-3,5-dioxa-4-bora-tricyclo[6.1.1.0$^{2,6}$]decane (6.00 g; 12.06 mmol; 76.2%; brown dark oil).

$^1$H NMR, 400 MHz, CDCl$_3$: 7.50 (s, 1H), 7.41-7.43 (m, 1H), 7.12-7.16 (m, 1H), 7.06-7.08 (m, 1H), 4.29-4.32 (m, 1H), 3.17-3.09 (m, 1H), 2.70-2.89 (m, 1H), 2.52-2.70 (m, 1H), 2.52 (s, 3H), 2.28-2.31 (m, 1H), 2.14-2.14 (m, 1H), 2.03 (t, J=5.68 Hz, 1H), 1.78-1.89 (m, 2H), 1.39 (s, 3H), 1.31 (s, 3H), 1.01-1.04 (m, 1H), 0.90-0.92 (m, 2H), 0.88 (s, 3H), 0.12 (s, 18H).

Step 8: 2-(7-Methyl-benzofuran-3-yl)-1-((1S,2S,6R, 8S)-2,9,9-trimethyl-3,5-dioxa-4-bora-tricyclo[6.1.1.0$^{206}$]dec-4-yl)-ethylamine Hydrochloride A stirred solution of (1S,2S,6R,8S)-4-[1-(1,1,1,3,3,3-Hexamethyl-disilazan-2-yl)-2-(7-methyl-benzofuran-3-yl)-ethyl]-2,9,9-trimethyl-3,5-dioxa-4-bora-tricyclo[6.1.1.0$^{2,6}$]decane (6.00 g; 12.06 mmol; 1.00 eq.) in Diethyl ether (60.00 ml) under nitrogen atmosphere is cooled to −10° C. To this 2M solution of Hydrochloric acid in diethylether (15.07 ml; 30.14 mmol; 2.50 eq.) is added drop wise. The reaction mixture is stirred at rt for 2 h. The reaction mixture is evaporated at 30° C. To the residue diethyl ether (20 mL) is added and the solid formed is filtered off, washed with cold diethyl ether and dried under vacuum to get 2-(7-Methyl-benzofuran-3-yl)-1-((1S,2S,6R,8S)-2,9,9-trimethyl-3,5-dioxa-4-bora-tricyclo[6.1.1.0$^{2,6}$]dec-4-yl)-ethylamine hydrochloride (3.50 g; 8.98 mmol; 74.5%; brown orange solid).

$^1$H NMR, 400 MHz, DMSO-d6: 8.09 (s, 3H), 7.83 (s, 1H), 7.52-7.53 (m, 1H), 7.12-7.19 (m, 2H), 4.39 (dd, J=1.84, 8.62 Hz, 1H), 3.07-3.13 (m, 1H), 3.03-3.07 (m, 2H), 2.43 (s, 4H), 2.28-2.30 (m, 1H), 2.07-2.08 (m, 1H), 1.92 (t, J=5.68 Hz, 1H), 1.82-1.84 (m, 1H), 1.71-1.75 (m, 1H), 1.19-1.25 (m, 8H), 1.00-1.08 (m, 1H), 0.78 (s, 3H).

Intermediate 4: 2-(7-Chloro-benzofuran-3-yl)-1-((1S,2S,6R,8S)-2,9,9-trimethyl-3,5-dioxa-4-bora-tricyclo[6.1.1.0$^{1a}$]dec-4-yl)-ethylamine Hydrochloride

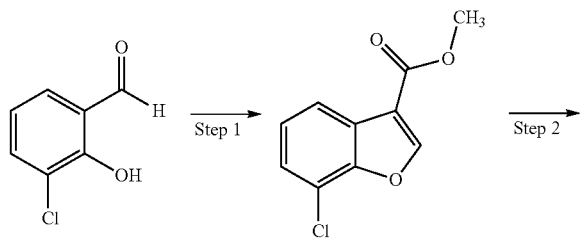

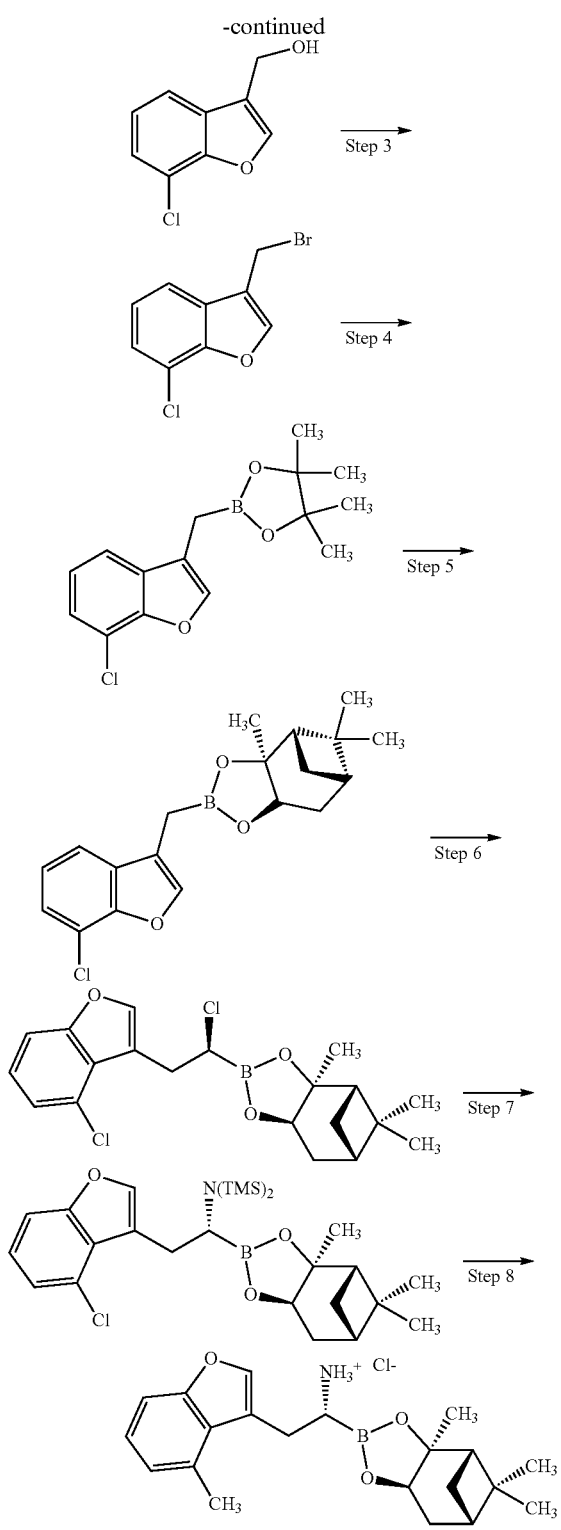

Step 1: 7-Chloro-benzofuran-3-carboxylic Acid Ethyl Ester

To a solution of 3-Chloro-2-hydroxy-benzaldehyde (25.00 g; 156.48 mmol; 1.00 eq.) in dichloromethane (250 ml), tetrafluoroboric acid diethylether complex (2.11 ml; 15.65 mmol; 0.10 eq.) is added. To the resulting dark red mixture, ethyldiazoacetate (35.55 ml; 336.44 mmol; 2.15 eq.) taken in dichloromethane (50 mL) is added dropwise slowly at 25-30° C. (internal temperature) for about 50 min. After 16 h, concentrated $H_2SO_4$ is added. The reaction mixture is stirred for 15 minutes. The reaction mixture is then neutralized with solid $NaHCO_3$, filtered through celite and the filtrate is concentrated to get a crude residue. The residue is purified by column chromatography using 2% ethyl acetate in petroleum ether to afford 7-chloro-benzofuran-3-carboxylic acid ethyl ester 2 (18.20 g; 81.02 mmol; 51.8%; colorless liquid).

$^1$H NMR, 400 MHz, DMSO-d6: 8.88 (s, 1H), 7.95-7.93 (m, 1H), 7.57-7.55 (m, 1H), 7.42 (t, J=7.8 Hz, 1H), 4.38-4.33 (m, 2H), 1.35 (t, J=7.1 Hz, 3H).

Step 2: (7-Chloro-benzofuran-3-yl)-methanol

To a stirred solution of 7-chloro-benzofuran-3-carboxylic acid ethyl ester (450 g; 2.0089 mol; 1.00 eq.) in DCM (4500 ml) at −78° C. is added diisobutyl aluminium hydride 1.0 M in toluene (4017 ml; 4.0178 mol; 2.20 eq.). The reaction mixture is then slowly allowed to attain room temp. and stirred at rt for 2 h. After completion of reaction as confirmed by TLC, the reaction mixture is quenched with 1.5N HCL (500 mL), passed through celite, washed with DCM (2000 mL). The filtrate is washed with brine solution (1×2000 mL). The organic layer is separated, dried over $Na_2SO_4$, filtered and concentrated in vacuum. The crude product is subjected to column chromatography and eluted with 15% ethyl acetate in petroleum ether to afford (7-Chloro-benzofuran-3-yl)-methanol 3 (365 g; 2.0054 mol; 99.8%; white solid foam).

$^1$H NMR, 400 MHz, DMSO-d6: 7.99 (s, 1H), 7.66 (dd, J=1.0, 7.8 Hz, 1H), 7.41 (dd, J=0.8, 7.8 Hz, 1H), 7.26 (t, J=7.8 Hz, 1H), 5.24 (t, J=5.6 Hz, 1H), 4.63-4.62 (m, 2H).

Step 3: 3-Bromomethyl-7-chloro-benzofuran

To an ice-cooled solution of (7-chloro-benzofuran-3-yl)-methanol (365 g; 2.0054 mol; 1.00 eq.) in diethyl ether (3650 ml) is added phosphorus tribromide (62.2 ml; 0.6618 mol; 0.33 eq.) dropwise under a nitrogen atmosphere. The reaction mixture is stirred under ice bath cooling for 30 minutes. Subsequently, the reaction mixture is poured into ice and extracted with diethyl ether. The organic layer is dried over anhydrous $Na_2SO_4$, filtered and concentrated to afford 3-bromomethyl-7-chloro-benzofuran (480 g; mol; 97.71%; white solid).

$^1$H NMR, 400 MHz, DMSO-d6: 8.29 (s, 1H), 7.72 (dd, J=1.0, 7.8 Hz, 1H), 7.49 (dd, J=0.8, 7.8 Hz, 1H), 7.36 (t, J=7.8 Hz, 1H), 4.90 (s, 2H).

Step 4: 7-Chloro-3-(4,4,5,5-tetramethyl-[1,3,2]dioxaborolan-2-ylmethyl)-benzofuran To a solution of 3-bromomethyl-7-chloro-benzofuran (480 g; 1.9591 mol; 1.00 eq.) in degased dioxane-1,4 (4800 ml) are added bis(pinacolato)diboron (596.9 g; 2.3510 mol; 1.20 eq.), dried potassium acetate (576.8 g; 5.877 mol; 3.00 eq.) and [1,1′-bis(diphenylphosphino)ferrocene]dichloropalladium(II), complex with dichloromethane (70.339; 0.0979 mol; 0.05 eq.). The reaction mixture is then heated at 100° C. under nitrogen atmosphere for overnight. The reaction mixture is diluted with dichloromethane and passed through celite. The filtrate is concentrated. The residue is dissolved in ethyl acetate and washed with brine (1000 mL×1). The organic layer is dried over anhydrous $Na_2SO_4$, filtered and concentrated in vacuo. The crude material is purified by column chromatography using 2% ethyl acetate in petroleum ether to obtain 7-chloro-3-(4,4,5,5-tetramethyl-[1,3,2] dioxaborolan-2-ylmethyl)-benzofuran (480 g; 1.6438 mol; 83.9%; yellow semi solid).

GCMS: m/z: 292 (Column: DB-5 ms (15 m×0.25 mm×0.25 μm); Carrier gas: helium, flow rate: 2.0 mL/min).

$^1$H NMR, 400 MHz, DMSO-d6: 7.79 (s, 1H), 7.52 (dd, J=1.0, 7.8 Hz, 1H), 7.38 (dd, J=0.8, 7.8 Hz, 1H), 7.27-7.23 (m, 1H), 2.17 (s, 2H), 1.18 (s, 12H).

Step 5: (1S,2S,6R,8S)-4-(7-Chloro-benzofuran-3-yl-methyl)-2,9,9-trimethyl-3,5-dioxa-4-bora-tricyclo [6.1.1.0$^{2,6}$]decane To an ice-cooled solution of 7-chloro-3-(4,4,5,5-tetramethyl-[1,3,2]dioxaborolan-2-ylmethyl)-benzofuran (480 g; 1.6438 mol; 1.00 eq.) in diethyl ether (5000 ml) and under a nitrogen atmosphere is added 1S, 2S, 3R, 5S-(+)-2,3-pinane diol (335.7 g; 1.9726 mol; 1.20 eq.). The reaction mixture is stirred at rt for 16 h. The reaction mixture is washed with water (2000 mL×1) and brine (1500 mL×1). The organic layer is dried over anhydrous Na$_2$SO$_4$, filtered and concentrated. The crude material is purified by flash chromatography using 1% ethyl acetate in petroleum ether to afford (1S,2S,6R,8S)-4-(7-chloro-benzofuran-3-yl-methyl)-2,9,9-trimethyl-3,5-dioxa-4-bora-tricyclo[6.1.1.0$^{2,6}$]decane (520 g; 1.510 mol; 91.9%; pale yellow semi-solid).

GCMS: m/z: 344 (Column: HP-5 MS (12 m×0.20 D mm×0.33 μm); Carrier gas: helium, flow rate: 2.0 mL/min)

$^1$H NMR, 400 MHz, DMSO-d6: 7.80 (s, 1H), 7.54 (dd, J=0.9, 7.8 Hz, 1H), 7.38 (dd, J=0.7, 7.8 Hz, 1H), 7.24 (t, J=7.8 Hz, 1H), 4.33 (t, J=6.9 Hz, 1H), 2.29-2.24 (m, 3H), 2.14-2.10 (m, 1H), 1.93 (t, J=5.4 Hz, 1H), 1.84-1.81 (m, 1H), 1.70-1.65 (m, 1H), 1.31 (s, 3H), 1.21 (s, 3H), 0.98 (d, J=10.72 Hz, 1H), 0.78 (s, 3H).

Step 6: (1S,2S,6R,8S)-4-[(S)-1-Chloro-2-(7-chloro-benzofuran-3-yl)-ethyl]-2,9,9-trimethyl-3,5-dioxa-4-bora-tricyclo[6.1.1.0$^{2,6}$]decane Dichloromethane (95.7 ml; 1.499 mol; 3.00 eq.) in THF (1200 mL) is taken in a RB-flask under a positive pressure of nitrogen and cooled to −95° C. using liquid nitrogen-ethanol mixture. To this n-butyl lithium (1.6 M in THF) (343.6 ml; 0.549 mol; 1.10 eq.) is added dropwise through the side neck of the RB-flask (at a medium rate, addition took about 45 min.) so that the internal temperature is maintained between −95° C. and −100° C. After addition, the reaction mixture is stirred for 30 minutes. During the course of the reaction a white precipitate is formed (internal temperature is maintained between −95° C. and −100° C.). Then, a solution of (1S,2S,6R,8S)-4-(7-chloro-benzofuran-3-ylmethyl)-2,9,9-trimethyl-3,5-dioxa-4-bora-tricyclo [6.1.1.0$^{2,6}$]decane (172 g; 0.4999 mol; 1.00 eq.) in THF (500 mL) is added dropwise through the side neck of the RB-flask (about 25 min) so that the internal temperature is again maintained between −95° C. and −100° C. After finishing addition, Zinc chloride (0.5 M in THF) (1599.6 ml; 0.7998 mol; 1.6 eq.) is immediately added dropwise through the side neck of the RB-flask (at a medium rate, addition took about 40 min.) so that the internal temperature is maintained between −95° C. and −100° C. The reaction mixture is then slowly allowed to attain −5° C. and stirred at −5° C. for 1.5 h. The reaction mixture is quenched by adding saturated NH$_4$Cl solution (500 mL). The reaction mixture is concentrated in vacuo (temperature of the bath 30° C.). The residue is partitioned between diethylether and saturated NH$_4$Cl solution. The organic layer is separated, dried over anhydrous Na$_2$SO$_4$ and concentrated (temperature of bath 30° C.) to afford (1S,2S,6R,8S)-4-[(S)-1-chloro-2-(7-chloro-benzofuran-3-yl)-ethyl]-2,9,9-trimethyl-3,5-dioxa-4-bora-tricyclo [6.1.1.0$^{2,6}$]decane (205 g; 0.5214 mol; 104.5%; orange oil).

GCMS: m/z: 392 (Column: ZB-1MS (10 m×0.101D mm×0.1 μm); Carrier gas: helium, flow rate: 2.0 mL/min)

$^1$H NMR, 400 MHz, CDCl$_3$: 7.64 (s, 1H), 7.50 (d, J=8.00 Hz, 1H), 7.33-7.31 (m, 1H), 7.23-7.21 (m, 1H), 4.36-4.34 (m, 1H), 3.29-3.27 (m, 1H), 3.22-3.20 (m, 1H), 2.34-2.32 (m, 1H), 2.15-2.14 (m, 1H), 2.06 (t, J=5.60 Hz, 1H), 1.91-1.83 (m, 7H), 1.36 (s, 3H), 1.29 (s, 3H), 1.05-1.02 (m, 1H), 0.85 (s, 3H).

Step 7: (1S,2S,6R,8S)-4-[(R)-2-(7-Chloro-benzofuran-3-yl)-1-(1,1,1,3,3,3-hexamethyl-disilazan-2-yl)-ethyl]-2,9,9-trimethyl-3,5-dioxa-4-bore-tricyclo [6.1.1.0$^{2,6}$]decane A solution of (1S,2S,6R,8S)-4-[(S)-1-chloro-2-(7-chloro-benzofuran-3-yl)-ethyl]-2,9,9-trimethyl-3,5-dioxa-4-bora-tricyclo[6.1.1.0$^{2,6}$]decane (205 g; 0.5214 mol; 1.00 eq.) in THF (2050 ml) under a positive pressure of nitrogen atmosphere is cooled to −78° C. To this a solution of lithium (bis-trimethylsilyl)-amide (1.0 M in THF) (625 ml; 0.6257 mol; 1.20 eq.) is added dropwise over a period of 30 minutes. The reaction mixture is allowed to attain rt and stirred at rt for 18 h. The solvent of the reaction mixture is evaporated at 30° C. The residue is triturated with hexane and the solid formed is filtered. The filtrate is allowed to stand for some time under vacuum and any solid if formed is filtered again. The filtrate is concentrated at 30° C. to obtain (1S,2S,6R,8S)-4-[(R)-2-(7-chloro-benzofuran-3-yl)-1-(1,1,1,3,3,3-hexamethyl-disilazan-2-yl)-ethyl]-2,9,9-trimethyl-3,5-dioxa-4-bora-tricyclo[6.1.1.0$^{2,6}$]decane (180 g; 0.3481 mol; 66.7%; orange oil).

$^1$H NMR, 400 MHz, CDCl$_3$: 7.63 (s, 1H), 7.51-7.49 (m, 1H), 7.29-7.27 (m, 1H), 7.19-7.15 (m, 1H), 4.32-4.29 (m, 1H), 3.63-3.61 (m, 1H), 3.14-3.12 (m, 1H), 2.87-2.85 (m, 1H), 2.26-2.24 (m, 1H), 2.14-2.12 (m, 1H), 1.88-1.86 (m, 1H), 1.88-1.76 (m, 2H), 1.33 (s, 3H), 1.30 (s, 3H), 1.02-0.99 (m, 1H), 0.85 (s, 3H), 0.07 (s, 18H).

Step 8: (R)-2-(7-Chloro-benzofuran-3-yl)-1-((1S,2S, 6R,8S)-2,9,9-trimethyl-3,5-dioxa-4-bora-tricyclo [6.1.1.0$^{2,6}$]dec-4-yl)-ethylamine Hydrochloride A stirred solution of (1S,2S,6R,8S)-4-[(R)-2-(7-chloro-benzofuran-3-yl)-1-(1,1,1,3,3,3-hexamethyl-disilazan-2-yl)-ethyl]-2,9,9-trimethyl-3,5-dioxa-4-bora-tricyclo [6.1.1.0$^{2,6}$]decane (180 g; 0.348 mol) in diethyl ether (1800 ml) under a nitrogen atmosphere is cooled to −10° C. To this solution, hydrochloric acid in diethyl ether (strength 2.0 M; 435.2 ml; 0.870 mol; 2.50 eq.) is added dropwise. The reaction mixture is stirred at rt for 2 h (precipitation of solid is observed during the course of the reaction). The reaction mixture is evaporated to dryness and the obtained solid is triturated with diethyl ether (500 mL) and subsequently filtered. The filter cake is washed with diethyl ether (3×300 mL) and dried under vacuum to afford (R)-2-(7-chloro-benzofuran-3-yl)-1-((1S,2S,6R,8S)-2,9,9-trimethyl-3,5-dioxa-4-bora-tricyclo[6.1.1.0$^{2,6}$]dec-4-yl)-ethylamine hydrochloride (81.5 g; 0.1992 mol; 57.2%; off-white solid).

$^1$H NMR, 400 MHz, CDCl$_3$: 8.09 (s, 3H), 7.97 (s, 1H), 7.73 (dd, J=1.52 Hz, 7.76 Hz, 1H), 7.44 (d, J=7.76 Hz, 1H), 7.31 (d, J=7.80 Hz, 1H), 4.42-4.40 (m, 1H), 3.16-3.07 (m,

3H), 2.32-2.27 (m, 1H), 2.10-2.04 (m, 1H), 1.93 (t, J=5.56 Hz, 1H), 1.83-1.71 (m, 2H), 1.27 (s, 3H), 1.25 (s, 3H), 1.08-1.02 (m, 1H), 0.79 (s, 3H).

Intermediate 5: (R)-2-(2,3-Dihydro-benzofuran-3-yl)-1-((1S,2S,6R,8S)-2,9,9-trimethyl-3,5-dioxa-4-bora-tricyclo[6.1.1.0$^{2,6}$]dec-4-yl)-ethylamine Hydrochloride Step 1: (1S,2S,6R,8S)-4-(2,3-Dihydro-benzofuran-3-ylmethyl)-2,9,9-trimethyl-3,5-dioxa-4-bora-tricyclo[6.1.1.0$^{2,6}$]decane

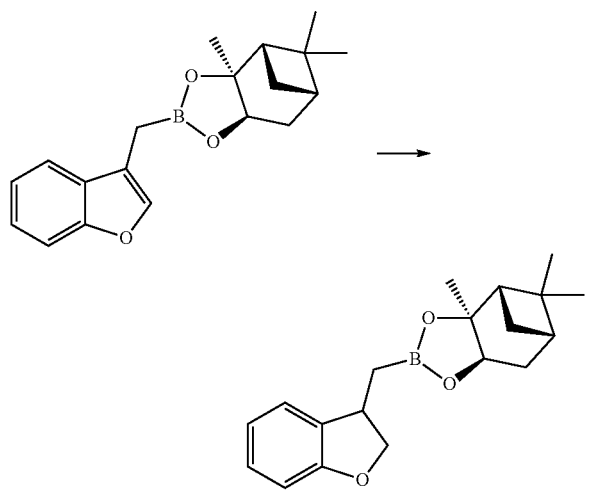

To a solution of (1S,2S,6R,8S)-4-Benzofuran-3-ylmethyl-2,9,9-trimethyl-3,5-dioxa-4-bora-tricyclo[6.1.1.0$^{2,6}$]decane (5.00 g; 10.72 mmol; 1.00 eq.) in methanol (100.00 ml) in a tiny clave is added palladium on carbon (10 wt %) (2.28 g; 2.14 mmol; 0.20 eq.). The contents are hydrogenated under a H$_2$ pressure of 5 Kg/cm$^2$ for 3 h. TLC analysis revealed complete conversion. The reaction mixture is filtered through celite and the filtrate is evaporated. The crude is purified by Biotage-isolera column chromatography (C$_{18}$ column; mobile phase: ACN/H$_2$O; 50:50 isocratic) to get a (1S,2S,6R,8S)-4-(2,3-Dihydro-benzofuran-3-yl methyl)-2,9,9-trimethyl-3,5-dioxa-4-bora-tricyclo[6.1.1.0$^{2,6}$]decane (4.10 g; 13.13 mmol; 122.5%; pale yellow liquid).

GCMS: m/z: 312.3.

Step 2: (1S,2S,6R,8S)-4-(1-Chloro-2-(7-methyl-benzofuran-3-yl)-ethyl]-2,9,9-trimethyl-3,5-dioxa-4-bora-tricyclo[6.1.1.0$^{2,6}$]decane

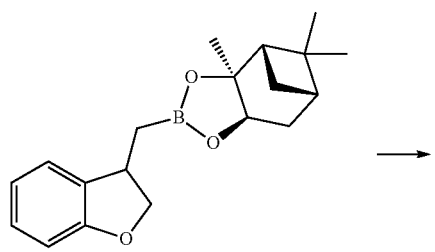

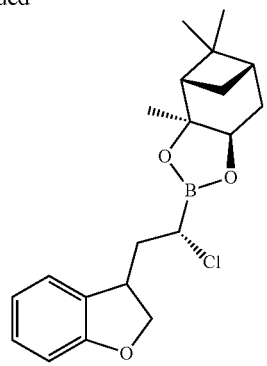

Dichloromethane (2.46 ml; 38.44 mmol; 3.00 eq.) in THF (40.00 ml) is taken in a RB-flask under a positive pressure of nitrogen and cooled to −95° C. using liquid nitrogen-ethanol mixture. To this n-butyl lithium (1.6 M in THF) (8.81 ml; 14.09 mmol; 1.10 eq.) is added drop wise through the sides of the RB-flask (at a medium rate, addition took about 20 min.) so that the internal temperature is maintained between −95° C. and −100° C. After addition, the reaction mixture is stirred for 25 minutes. During the course of the reaction a white precipitate is formed (The internal temperature is maintained between −95° C. and −100° C.). Then a solution of (1S,2S,6R,8S)-4-(2,3-Dihydro-benzofuran-3-ylmethyl)-2,9,9-trimethyl-3,5-dioxa-4-bora-tricyclo[6.1.1.0$^{2,6}$]decane (4.00 g; 12.81 mmol; 1.00 eq.) in THF (15.00 ml) is added drop wise through the sides of the RB-flask (about 25 min) so that the internal temperature is maintained between −95° C. and −100° C. After addition, immediately zinc chloride (0.5 M in THF) (25.62 ml; 12.81 mmol; 1.00 eq.) is added drop wise through the sides of the RB-flask (at a medium rate, addition took about 25 min.) so that the internal temperature is maintained between −95° C. and −100° C. The reaction mixture is then slowly allowed to attain rt and stirred at rt for 18 h. The reaction mixture is concentrated (temperature of the bath 30° C.). The residue is partitioned between diethylether and saturated NH$_4$Cl solution. The organic layer is dried over anhydrous Na$_2$SO$_4$ and concentrated (temperature of bath 30° C.) to afford (1S,2S,6R,8S)-4-[(S)-1-Chloro-2-(2,3-dihydro-benzofuran-3-yl)-ethyl]-2,9,9-trimethyl-3,5-dioxa-4-bora-tricyclo[6.1.1.0$^{2,6}$] decane (4.60 g; 12.75 mmol; 99.5%; yellow oil).

1H NMR, 400 MHz, CDCl$_3$: 7.29 (d, J=6.72 Hz, 1H), 7.21-7.10 (m, 1H), 6.90-6.77 (m, 2H), 4.68-4.65 (m, 1H), 4.32-4.29 (m, 2H), 3.65-3.60 (m, 1H), 2.40-2.08 (m, 4H), 1.94-1.85 (m, 2H), 1.42 (s, 3H), 1.33 (5, 3H), 1.22 (s, 3H), 1.17-1.15 (m, 1H), 0.86 (s, 3H).

Step 3: (1S,2S,6R,8S)-4-[(R)-2-(2,3-Dihydro-benzo-furan-3-yl)-1-(1,1,1,3,3,3-hexamethyl-disilazan-2-yl)-ethyl]-2,9,9-trimethyl-3,5-dioxa-4-bore-tricyclo [6.1.1.0$^{2,6}$]decane Step 4: (R)-2-(2,3-Dihydro-benzofuran-3-yl)-1-((1S, 2S,6R,8S)-2,9,9-trimethyl-3,5-dioxa-4-bora-tricyclo [6.1.1.0$^{2,6}$]dec-4-yl)-ethylamine Hydrochloride

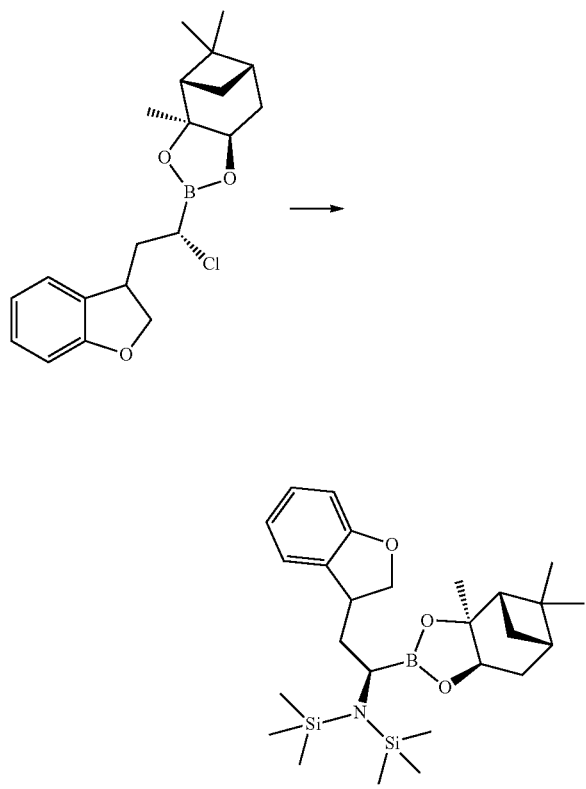 [SMILES: CC1(C)[C@@H]2C[C@H]3OB([C@H](Cl)CC4COc5ccccc54)O[C@@]3(C)[C@H]1C2 ; CC1(C)[C@@H]2C[C@H]3OB([C@H](CC4COc5ccccc54)N([Si](C)(C)C)[Si](C)(C)C)O[C@@]3(C)[C@H]1C2]

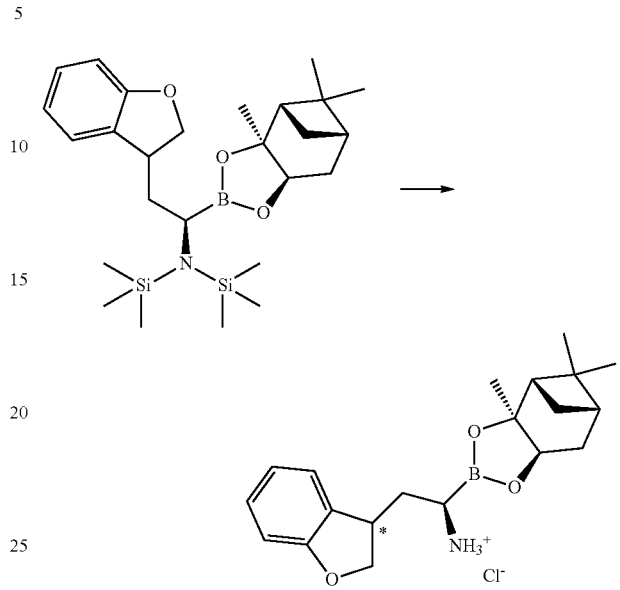

A solution of (1S,2S,6R,8S)-4-[(S)-1-Chloro-2-(2,3-di-hydro-benzofuran-3-yl)-ethyl]-2,9,9-trimethyl-3,5-dioxa-4-bora-tricyclo[6.1.1.0$^{2,6}$]decane (4.60 g; 12.75 mmol; 1.00 eq.) in THF (45.00 ml) under a positive pressure of nitrogen atmosphere is cooled to −78° C. To this a solution of Lithium(bistrimethylsilyl)amide (1.0 M in THF) (16.58 ml; 16.58 mmol; 1.30 eq.) is added drop wise over a period of 30 minutes. The reaction mixture is allowed to attain rt and stirred at rt for 18 h. The reaction mixture is evaporated at 30° C. The residue is triturated with hexane and the solid formed is filtered. The filtrate is allowed to stand for some time under vacuum and any solid if formed is filtered again. The filtrate is concentrated at 30° C. to get (1S,2S,6R,8S)-4-[(R)-2-(2,3-Dihydro-benzofuran-3-yl)-1-(1,1,1,3,3,3-hexamethyl-disilazan-2-yl)-ethyl]-2,9,9-trimethyl-3,5-dioxa-4-bora-tricyclo[6.1.1.0$^{2,6}$]decane (3.77 g; 7.76 mmol; 60.9%; yellow oil). 1H NMR, 400 MHz, CDCl$_3$: 7.22-7.10 (m, 2H), 6.90-6.79 (m, 2H), 4.62-4.59 (m, 1H), 4.33-4.27 (m, 1H), 2.34-2.20 (m, 2H), 2.07-2.05 (m, 1H), 1.94-1.84 (m, 2H), 1.40 (s, 3H), 1.30 (s, 3H), 1.15-1.13 (m, 1H), 0.86 (s, 3H), 0.10 (s, 18H).

A stirred solution of (1S,2S,6R,8S)-4-[(R)-2-(2,3-Di-hydro-benzofuran-3-yl)-1-(1,1,1,3,3,3-hexamethyl-disila-zan-2-yl)-ethyl]-2,9,9-trimethyl-3,5-dioxa-4-bora-tricyclo [6.1.1.0$^{2,6}$]decane (3.77 g; 7.76 mmol; 1.00 eq.) in Et$_2$O (35.00 ml) under nitrogen atmosphere is cooled to −10° C. To this 2 N HCl in diethylether (9.70 ml; 19.41 mmol; 2.50 eq.) is added drop wise. The reaction mixture is stirred at rt for 2 h. The reaction mixture is evaporated to dryness under reduced pressure to get a solid. The solid formed is triturated with diethylether, filtered, washed with diethylether and dried under vacuum get (R)-2-(2,3-Dihydro-benzofuran-3-yl)-1-((1S,2S,6R,8S)-2,9,9-trimethyl-3,5-dioxa-4-bora-tri-cyclo[6.1.1.0$^{2,6}$]dec-4-yl)-ethylamine hydrochloride (2.30 g; 5.25 mmol; yield 67.7%; pale brown solid). Analysis showed the presence of isomers (~65.50%+20.75%) at the indicated (*) position.

LCMS: 4.73 min., 86.25% (max), 80.47% (220 nm), 342.20 (M+1).

$^1$H NMR, 400 MHz, DMSO-d6: 8.11 (s, 3H), 7.23-7.19 (m, 1H), 7.13-7.10 (m, 1H). 6.85 (t, J=7.40 Hz, 1H), 6.77 (d, J=8.04 Hz, 1H), 4.61-4.57 (m, 1H), 4.48-4.45 (m, 1H), 4.25-4.22 (m, 1H), 3.68-3.62 (m, 1H), 2.90-2.85 (m, 1H), 2.34-2.32 (m, 1H), 2.19-2.17 (m, 1H), 2.02-1.99 (m, 2H), 1.89-1.77 (m, 3H), 1.39 (s, 3H), 1.25 (s, 3H), 1.17-1.14 (m, 1H), 0.82 (s, 3H).

By similar sequences described for intermediates 2-4 other examples of the following moiety can be prepared

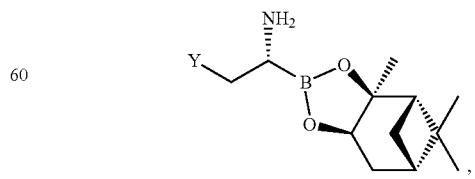

such as in particular compounds wherein the group Y denotes one of the following groups:

69

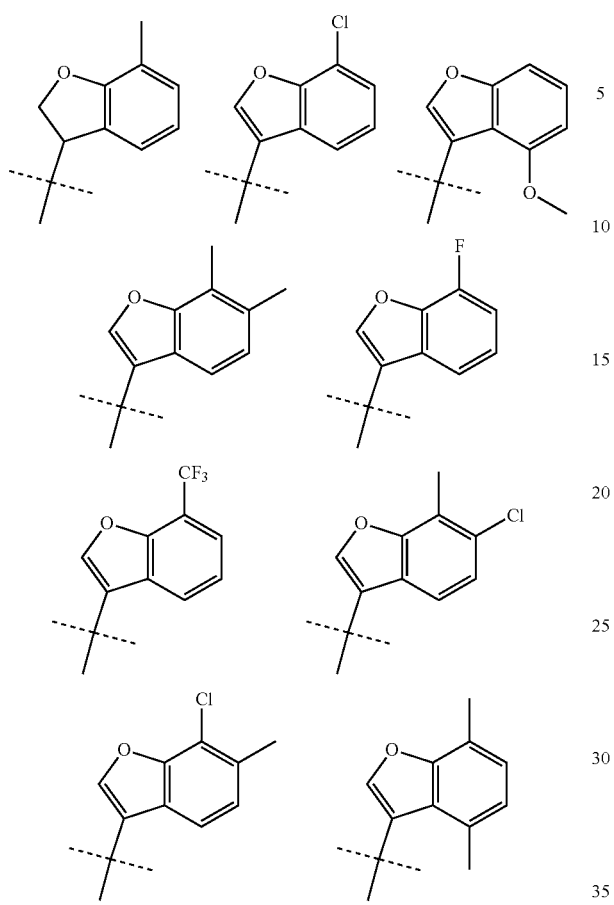

Acid Intermediate 1: (1S,2R,4R)-7-oxabicycio[2.2.1]heptane-2-carboxylic Acid

Step 1: (1S,2R,4R)-7-Oxa-bicyclo[2.2.1]heptane-2-carboxylic acid (R)-1-phenyl-ethyl Ester

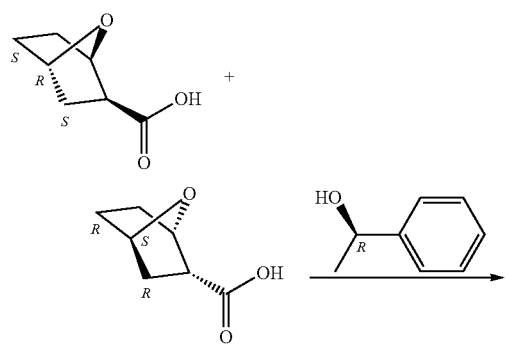

70

-continued

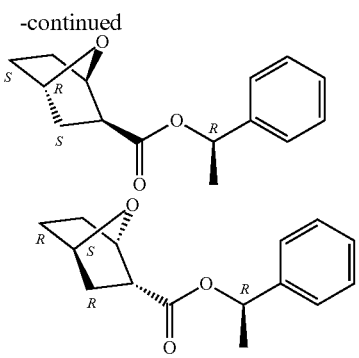

To a solution of 7-oxa-bicyclo[2.2.1]heptane-2-carboxylic acid (4.680 g; 31.276 mmol, racemic) in dry dichloromethane (max. 0,005% $H_2O$) SeccoSolv® (100 ml) under an atmosphere of argon are added (R)-1-phenyl-ethanol (4.623 ml; 37.531 mmol), 4-(dimethylamino)pyridine for synthesis (DMAP) (3.821 g; 31.276 mmol) and (3-dimethylamino-propyl)-ethyl-carbodiimide hydrochloride (EDCl) (6.730 g; 34.404 mmol) under stirring at 0° C. Subsequently, the clear reaction solution is stirred over night at room temperature. After completion of the ester formation, the reaction is quenched by adding sat. $NH_4Cl$ (aq) solution. Then, the mixture is extracted twice with $CH_2Cl_2$. The organic layer is washed trice with sat. $NaHCO_3$ (aq) and brine, dried over $Na_2SO_4$, filtrated and evaporated to dryness. The crude product is purified by flash chromatography (silica gel; n-heptane/ethyl acetate 0-30% ethyl acetate) to obtain 7.496 g (30.43 mmol, 97.3%) of a colorless oil (HPLC: 100% pure mixture of diastereomers).

The mixture of diastereomers is separated by preparative, chirale HPLC (Chiralcel OD-H; n-heptane/2-propanol 95:5; 220 nm) to obtain (1R,2S,4S)-7-Oxa-bicyclo[2.2.1]heptane-2-carboxylic acid (R)-1-phenyl-ethyl ester (3.22 g, colorless oil, yield 41.8%, chiral HPLC 100%) and (1S,2R,4R)-7-Oxa-bicyclo[2.2.1]heptane-2-carboxylic acid (R)-1-phenyl-ethyl ester (3.14 g, oil, yield 40.7% chiral HPLC 100%).

Step 2: (1S,2R,4R)-7-oxabicyclo[2.2.1]heptane-2-carboxylic Acid

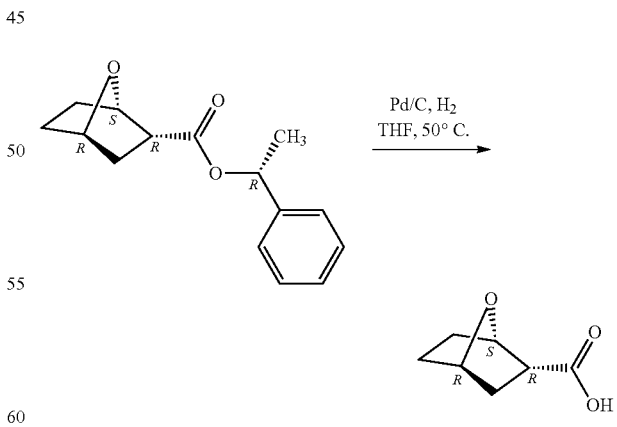

To a solution of (1S,2R,4R)-7-Oxa-bicyclo[2.2.1]heptane-2-carboxylic acid (R)-1-phenyl-ethyl ester (46.74 g; 182.75 mmol; 1.00 eq.) in THF (233.70 ml), palladium on carbon (10% w/w) (1.94 g; 1.83 mmol; 0.01 eq.) is added. The contents are hydrogenated under a $H_2$ atmosphere at 50° C. and 5 bar pressure for 16 h. After completion of the hydrogenation, the reaction mixture is filtered through celite, the filtrate is evaporated to dryness and taken up in pentane. The organic layer is extracted trice with water. Subsequently, the water layer is lyophilized to obtain (1S,2R,4R)-7-oxabicyclo[2.2.1]heptane-2-carboxylic acid (22.62 g; 159.09 mmol; yield 87.1%) as a colorless solid.

TLC: Chloroform/methanol (9.5/0.5) Rf 0.5. $^1$H-NMR 400 MHz, DMSO-d6: 12.16 (s, 1H), 4.66 (d, J=4.4 Hz, 1H), 4.54 (t, J=4.4 Hz, 1H), 2.57 (d, J=35.2 Hz, 1H), 1.91-1.86 (m, 1H), 1.65-1.37 (m, 4H), 1.34-1.33 (m, 1H). Optical rotation [□]$^{20}$ $^D$=+31.9°; □D20=+0.0644° (ethanol, 20.16 mg/10 ml).

Acid Intermediate 2: (1R,2S,4S)-7-oxabicyclo[2.2.1]heptane-2-carboxylic Acid

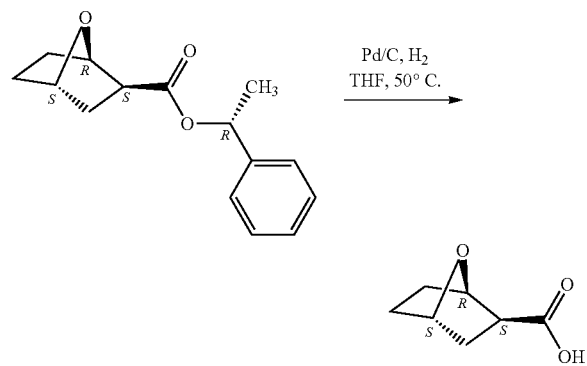

To a solution of (1R,2S,4S)-7-Oxa-bicyclo[2.2.1]heptane-2-carboxylic acid (R)-1-phenyl-ethyl ester (4.52 g; 17.98 mmol; 1.00 eq.) in THF (22.60 ml) Palladium on carbon (10% w/w) (0.19 g; 0.18 mmol; 0.01 eq.) is added. The contents are hydrogenated under a H$_2$ atmosphere at 50° C. for 12 h. TLC analysis revealed starting is completed. The reaction mixture is filtered through Celite and the filtrate is evaporated to get (1R,2S,4S)-7-Oxa-bicyclo[2.2.1]heptane-2-carboxylic acid (2.10 g; 14.77 mmol; 82.1%; off white solid)

$^1$H-NMR 400 MHz, DMSO-d6: 12.16 (s, 1H), 4.66 (d, J=4.4 Hz, 1H), 4.54 (t, J=4.4 Hz, 1H), 2.57 (d, J=35.2 Hz, 1H), 1.91-1.86 (m, 1H), 1.65-1.37 (m, 4H), 1.34-1.33 (m, 1H).

Acid Intermediate 3: (1S,8R)-8-Methyl-11-oxa-tricyclo[6.2.1.0$^{2,7}$]undeca-2,4,6-triene-1-carboxylic Acid Lithium (Salt)

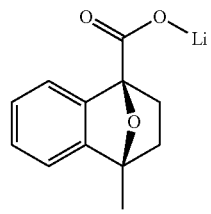

Step 1: 8-Methyl-11-oxa-tricyclo[6.2.1.0$^{2,7}$]undeca-2,4,6,9-tetraene-1-carboxylic Acid Methyl Ester

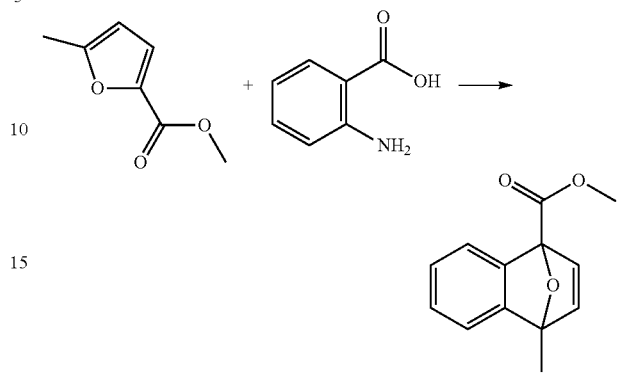

Isopentyl nitrite (3.64 ml; 27.12 mmol) is added to a solution of 3.72 g anthranilic acid (27.12 mmol) and trifluoroacetic acid (0.26 ml; 3.39 mmol) in 45 ml dried THF at 0° C. The resulting solution is stirred vigorously for a few minutes at 0° C. and then warmed up to rt. After stirring for 1 h at rt, the color of the suspension turned into yellow. The brown solid is filtered off and washed with dry THF before transferring it into a flask containing a solution of 5-methyl-furan-2-carboxylic acid methyl ester (2.00 g; 13.56 mmol) in ethylene glycol dimethyl ether for synthesis (45.00 ml). The resulting mixture is then gradually heated to 100° C. until decomposition is complete and stirred for another hour at 100° C. After evaporation of the solvent the reaction mixture is purified by flash chromatography (silica gel; EE/heptane gradient; 0-25% EE) to obtain 8-methyl-11-oxa-tricyclo [6.2.1.0$^{2,7}$]undeca-2,4,6,9-tetraene-1-carboxylic acid methyl ester (1.82 g; 53.7%; yellow gum) as a 1:1 mixture of stereoisomers.

LCMS Method A: (M+H) 217.0; Rt 2.03 min.

Step 2: (1S,8R)-8-Methyl-11-oxa-tricyclo[6.2.1.0$^{2,7}$]undeca-2,4,6-triene-1-carboxylic Acid Methyl Ester and (1R,8S)-8-Methyl-11-oxa-tricyclo[6.2.1.0$^{2,7}$]undeca-2,4,6-triene-1-carboxylic Acid Methyl Ester

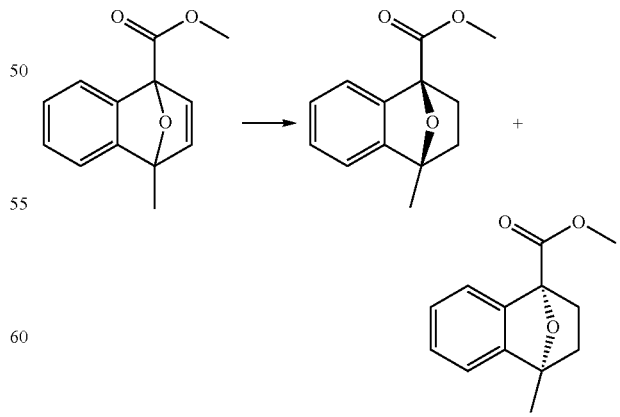

A solution 8-methyl-11-oxa-tricyclo[6.2.1.0$^{2,7}$]undeca-2,4,6,9-tetraene-1-carboxylic acid methyl ester (1.82 g, 7.28 mmol) in 18 ml EE is hydrogenated at rt and normal pressure using 500 mg Pd/C (54% water) until the reaction is complete. The reaction mixture is filtrated and the filtrate is concentrated. The residual sticky oil (mixture of stereoisomers) is separated using chiral preparative SFC (Chiral Cel 00-H; $CO_{2/2}$-propanol 58.5: 1.5; 220 nm) to obtain (1S,8R)-8-methyl-11-oxa-tricyclo[6.2.1.0$^{2,7}$]undeca-2,4,6-triene-1-carboxylic acid methyl ester (439 mg, yield 25.3%) and (1R,8S)-8-methyl-11-oxa-tricyclo[6.2.1.0$^{2,7}$]undeca-2,4,6-triene-1-carboxylic acid methyl ester (449 mg, yield 25.9%), both as colourless oils.

LCMS Method A: (M+H) not detected; Rt 2.09 min (same for both compounds).

Step 3: (1S,8R)-8-Methyl-11-oxa-tricyclo[6.2.1.0$^{2,7}$]undeca-2,4,6-triene-1-carboxylic Acid Lithium (Salt)

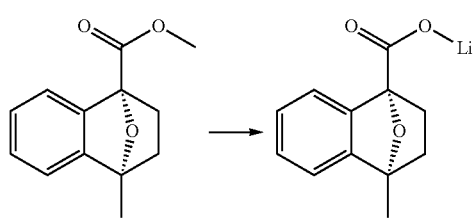

(1S,8R)-8-Methyl-11-oxa-tricyclo[6.2.1.0$^{2,7}$]undeca-2,4,6-triene-1-carboxylic acid methyl ester (0.439 g; 1.84 mmol) is taken up in 5 ml deionised water and 2.5 ml THF. LiOH (44 mg, 1.84 mmol) is added, the mixture is stirred under argon at rt for 1 h and evaporated to yield the title compound, which is used without further purification.

LCMS Method A: (M−Li+H−18) 187; Rt 1.71 min.

Acid Intermediate 4: (1R,8S)-8-Methyl-11-oxa-tricyclo[6.2.1.0$^{2,7}$]undeca-2,4,6-triene-1-carboxylic Acid Lithium

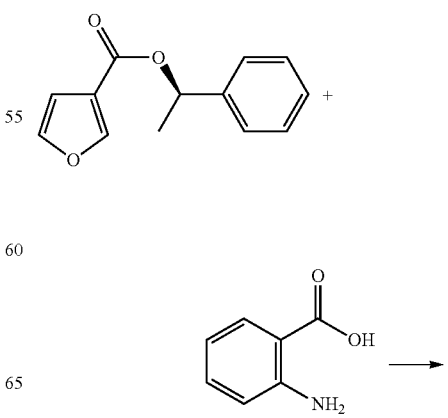

(1R,8S)-8-Methyl-11-oxa-tricyclo[6.2.1.0$^{2,7}$]undeca-2,4,6-triene-1-carboxylic acid methyl ester (purity 91%; 0.449 g; 1.88 mmol) is taken up in ml deionised water and 2.5 ml THF. LiOH (45 mg, 1.88 mmol) is added, the mixture is stirred under argon at rt for 1 h and evaporated to yield the title compound.

LCMS Method A: (M−Li+H−18) 187; Rt 1.71 min.

Acid Intermediate 5: (1S,8R)-11-Oxa-tricyclo[6.2.1.0$^{2,7}$]undeca-2,4,6-triene-9-carboxylic Acid

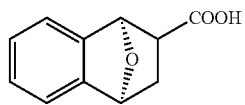 [SMILES: O=C(O)C1C[C@@H]2O[C@H]1c1ccccc12]

Step 1: Furan-3-carboxylic acid (R)-1-phenyl-ethyl Ester

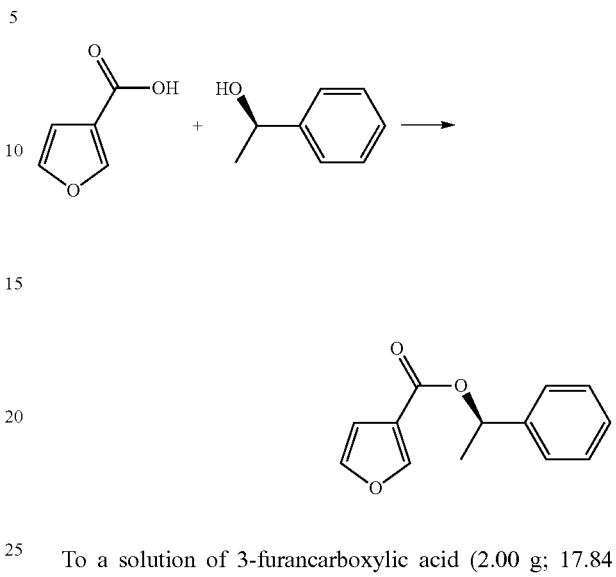

To a solution of 3-furancarboxylic acid (2.00 g; 17.84 mmol) in 40 ml dry dichloromethane are added (R)-1-phenyl-ethanol (2.64 ml; 21.41 mmol), 4-dimethylamino-pyridine (2.18 g; 17.85 mmol) and (3-dimethylamino-propyl)-ethyl-carbodiimide hydrochloride (3.84 g; 19.63 mmol) under argon-atmosphere at 0° C. The clear reaction solution is stirred without further cooling for 3 h. The reaction solution is quenched with sat. NH$_4$Cl and extracted with dichloromethane. The organic layer is washed 3× with sat. NaHCO$_3$ solution and brine, dried over Na$_2$SO$_4$, and filtrated. After evaporation of the solvent the reaction mixture is purified by flash chromatography (silica gel; EE/heptane gradient; 0-30% EE) to obtain furan-3-carboxylic acid (R)-1-phenyl-ethyl ester (3.55 g; yield 90%; yellow oil).

LCMS Method A: (M+H) not detected; Rt 2.46 min.

Step 2: (1R,8R)-11-Oxa-tricyclo[6.2.1.0$^{2,7}$]undeca-2,4,6,9-tetraene-9-carboxylic acid (R)-1-phenyl-ethyl ester and (1S,8S)-11-Oxa-tricyclo[6.2.1.0$^{2,7}$]undeca-2,4,6,9-tetraene-9-carboxylic acid (R)-1-phenyl-ethyl Ester

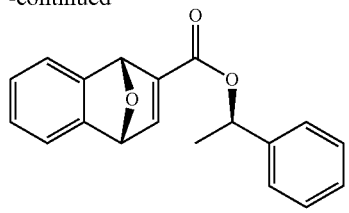

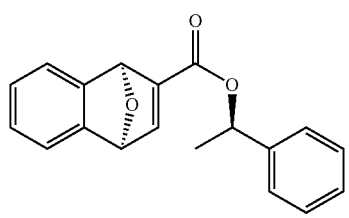

Isopentyl nitrite (1.91 ml; 14.18 mmol) is added to a solution of anthranilic acid (1.94 g, 14.18 mmol) and trifluoroacetic acid (0.137 ml; 1.77 mmol) in 22 ml dried THF at 0° C. The resulting solution is stirred vigorously for a few minutes at 0° C. then warmed up to rt. After stirring for 1 h at rt the color of the suspension turned into yellow. The liquid is removed by decantation and the remaining brown solid is washed with dry THF before transferring it into a flask containing a solution of furan-3-carboxylic acid (R)-1-phenyl-ethyl ester (1.60 g; 7.09 mmol) in ethylene glycol dimethyl ether for synthesis (22 ml). The resulting mixture is then gradually heated to 100° C. until decomposition is complete and stirred for another hour at 100° C. After evaporation of the solvent the reaction mixture is purified by flash chromatography (silica gel; EE/heptane gradient; 0-35% EE) to obtain 677 mg 11-Oxa-tricyclo[6.2.1.0$^{2,7}$]undeca-2,4,6,9-tetraene-9-carboxylic acid (R)-1-phenyl-ethyl ester (677 mg, colorless oil) as a mixture of diastereomers. This mixture is separated using chiral preparative HPLC (Chiral Pak AD; n-heptan/ethanol 1:1; 220 nm) to obtain (1R,8R)-11-Oxa-tricyclo[6.2.1.0$^{2,7}$]undeca-2,4,6,9-tetraene-9-carboxylic acid (R)-1-phenyl-ethyl ester (190 mg, chiral HPLC>97%; Rt 7.73 min) and (1S,8S)-11-Oxa-tricyclo[6.2.1.0$^{2,7}$]undeca-2,4,6,9-tetraene-9-carboxylic acid (R)-1-phenyl-ethyl ester (180 mg; chiral HPLC>96%; Rt 12.53 min).

Step 3: (1S,8R)-11-Oxa-tricyclo[6.2.1.0$^{2,7}$]undeca-2,4,6-triene-9-carboxylic acid (R)-1-phenyl-ethyl Ester

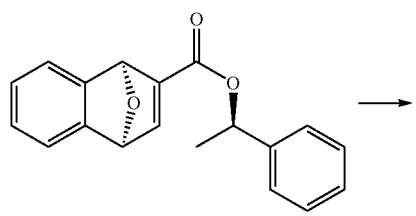

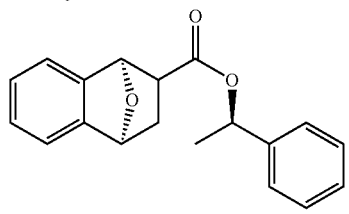

A solution (1S,8S)-11-Oxa-tricyclo[6.2.1.0$^{2,7}$]undeca-2,4,6,9-tetraene-9-carboxylic acid (R)-1-phenyl-ethyl ester (0.470 g, 1.190 mmol) in 10 ml THF is hydrogenated at rt and normal pressure using 500 mg Pd/C (54% water) until the reaction is complete. The reaction mixture is filtrated, the filtrate is concentrated and purified by flash chromatography (silica gel; EE/heptane gradient; 0-60% EE) to obtain (1S,8R)-11-Oxa-tricyclo[6.2.1.0$^{2,7}$]undeca-2,4,6-triene-9-carboxylic acid (R)-1-phenyl-ethyl ester (184 mg) as colourless oil.

LCMS Method A: (M+H) not detected; Rt 2.51 min.

Step 4: (1S,8R)-11-Oxa-tricyclo[6.2.1.0$^{2,7}$]undeca-2,4,6-triene-9-carboxylic Acid

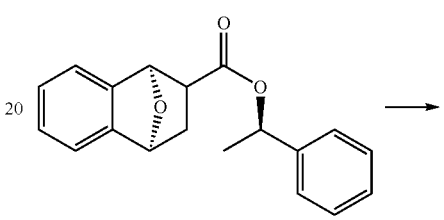

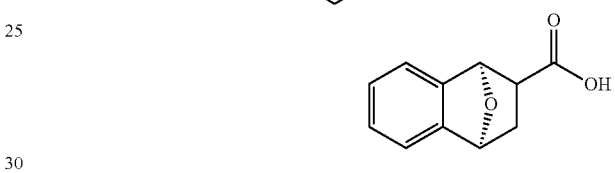

A solution of (1S,8R)-11-Oxa-tricyclo[6.2.1.0$^{2,7}$]undeca-2,4,6-triene-9-carboxylic acid (R)-1-phenyl-ethyl ester (0.184 g, 0.626 mmol) in 10 ml THF is hydrogenated at rt and normal pressure using 200 mg Pd/C (54% water) overnight. The reaction mixture is filtrated and the filtrate is evaporated to obtain 130 mg (1S,8R)-11-Oxa-tricyclo [6.2.1.0$^{2,7}$]undeca-2,4,6-triene-9-carboxylic acid as white solid.

LCMS Method A: (M−18) 174; Rt 1.42 min.

Acid Intermediate 6: (1R,8S)-11-Oxa-tricyclo [6.2.1.0$^{2,7}$]undeca-2,4,6-triene-9-carboxylic Acid

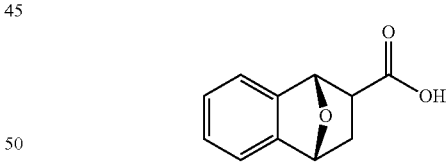

Step 1: (1R,8S)-11-Oxa-tricyclo[6.2.1.0$^{2,7}$]undeca-2,4,6-triene-9-carboxylic Acid (R)-1-phenyl-ethyl Ester

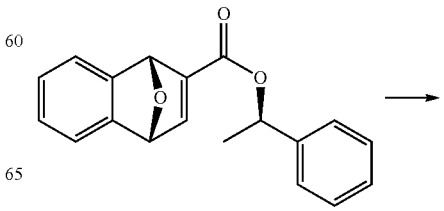

77
-continued

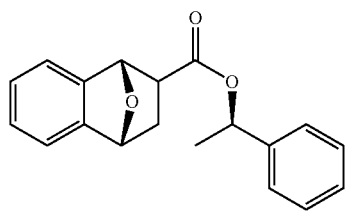

A solution (1R,8R)-11-Oxa-tricyclo[6.2.1.0$^{2,7}$]undeca-2,4,6,9-tetraene-9-carboxylic acid (R)-1-phenyl-ethyl ester (0.470 g, purity 76%, 1.22 mmol) in 10 ml THF is hydrogenated at rt and normal pressure using 100 mg Pd/C (54% water) until the reaction is complete (5 min). The reaction mixture is filtrated, the filtrate is concentrated and purified by flash chromatography (silica gel; EE/heptane gradient; 0-50% EE) to obtain (1R,8S)-11-Oxa-tricyclo[6.2.1.0$^{2,7}$]undeca-2,4,6-triene-9-carboxylic acid (R)-1-phenyl-ethyl ester (107 mg, yield 30%) as colourless wax.

LCMS Method A: (M+H) not detected; Rt 2.52 min.

Step 2: (1R,8S)-11-Oxa-tricyclo[6.2.1.0$^{2,7}$]undeca-2,4,6-triene-9-carboxylic Acid

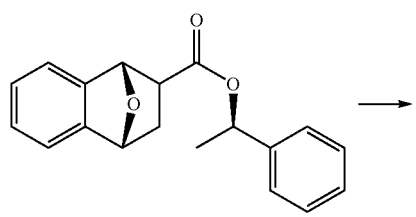

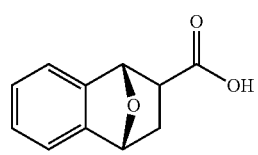 [SMILES: O=C(O)C1C[C@H]2O[C@@H]1c1ccccc12]

A solution of (1S,8R)-11-Oxa-tricyclo[6.2.1.0$^{2,7}$]undeca-2,4,6-triene-9-carboxylic acid (R)-1-phenyl-ethyl ester (0.107 g, 0.364 mmol) in 10 ml THF is hydrogenated at rt and normal pressure using 100 mg Pd/C (54% water) overnight. The reaction mixture is filtrated and the filtrate is evaporated to obtain (1R,8S)-11-Oxa-tricyclo[6.2.1.0$^{2,7}$]undeca-2,4,6-triene-9-carboxylic acid (69 mg; 92% yield) as white solid.

LCMS Method A: (M+H) not detected; Rt 1.36 min.

78

Example 1: [(1R)-2-[(3S)-2,3-dihydro-1-benzofuran-3-yl]-1-{[(1S,2R,4R)-7-oxabicyclo[2.2.1]heptan-2-yl]formamido}ethyl]boronic Acid (Compound No. 1)

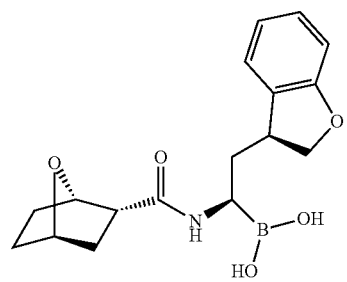 [SMILES: O=C(N[C@@H](C[C@@H]1COc2ccccc21)B(O)O)[C@@H]1C[C@H]2CC[C@@H]1O2]

Step 1: (1S,2R,4R)-7-Oxa-bicyclo[2.2.1]heptane-2-carboxylic Acid [(R)-2-(S)-2,3-dihydro-benzofuran-3-yl-1-((1S,2S,6R,8S)-2,9,9-trimethyl-3,5-dioxa-4-bora-tricyclo[6.1.1.0$^{2,6}$]dec-4-yl)-ethyl]-amide

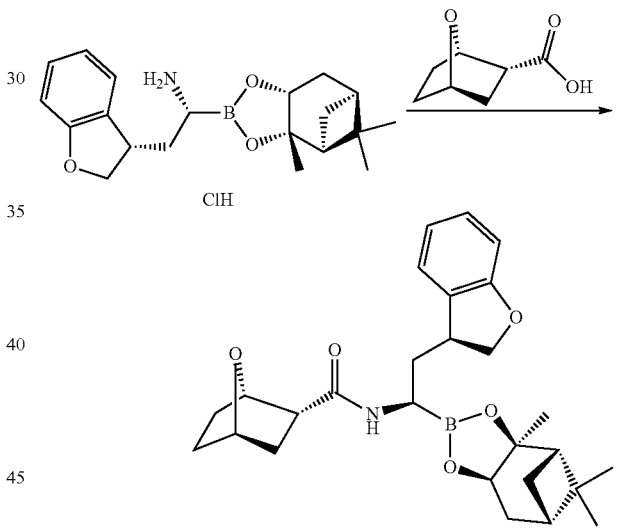

To a solution of (R)-2-(S)-2,3-Dihydro-benzofuran-3-yl-1-((1S,2S,6R,8S)-2,9,9-trimethyl-3,5-dioxa-4-bora-tricyclo[6.1.1.0$^{2,6}$]dec-4-yl)-ethylamine hydrochloride (0.250 g; 0.66 mmol) in 5 ml dried DMF is added at –15° C. and argon atmosphere (1S,2R,4R)-7-oxa-bicyclo[2.2.1]heptane-2-carboxylic acid (0.113 g; 0.79 mmol), ethyl-diisopropyl-amine (0.34 ml; 1.99 mmol) and TBTU (0.70 g; 2.18 mmol). The yellow reaction solution is stirred 1 h at –10° C., than 1 h at rt. The reaction solution is cooled with ice and diluted with ethyl acetate. After separation the organic phase is washed with brine and sat. NaHCO$_3$-solution, dried over sodium sulfate, filtered and concentrated in vacuo (bath-temp 30° C.). The obtained orange oil is first purified by flash chromatography (silica-gel; heptane/EE gradient, 0-100% EE) to yield a mixture of diastereomers, which is separated using chiral SFC (ChiralPak AD, CO$_2$: Methanol (88:12)). 122 mg of the title compound (yield 39.6%) are obtained as colourless oil.

LCMS Method A: (M+H) 466.2; Rt 2.49 min

Step 2: [(1R)-2-[(3S)-2,3-dihydro-1-benzofuran-3-yl]-1-{[(1S,2R,4R)-7-oxabicyclo[2.2.1]heptan-2-yl]formamido}ethyl]boronic Acid (Compound No. 1)

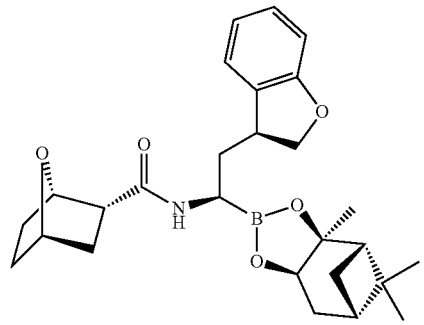

To a two phase system of (1S,2R,4R)-7-Oxa-bicyclo[2.2.1]heptane-2-carboxylic acid [(R)-2-(S)-2,3-dihydro-benzofuran-3-yl-1-((1S,2S,6R,8S)-2,9,9-trimethyl-3,5-dioxa-4-bora-tricyclo[6.1.1.0$^{2,6}$]dec-4-yl)-ethyl]-am ide (0.206 g; 0.44 mmol) in 27 ml n-pentane and 20.6 ml methanol is added at 0° C. isobutylboronic acid (0.180 g; 1.77 mmol) and 2 N HCl (1.99 ml; 3.98 mmol). The reaction is stirred at rt overnight. The pentane phase is separated and the methanolic aqueous phase is washed 5× with pentane. The methanolic phase is concentrated in vacuo, diluted with ice water and alkalised with 1 N NaOH. Afterwards is extracted with DCM (2×). The aqueous phase is acidified 1 N HCl and extracted with DCM (5×). This organic phase is dried over Na$_2$SO$_4$, filtrated and evaporated. The residue is solved in acetonitrile/water and lyophilized to give 104 mg (yield: 71%) of the title compound as white solid.

$^1$H NMR (500 MHz, DMSO-d$_6$/D$_2$O) d 7.23-7.20 (m, 1H), 7.13-7.09 (m, 1H), 6.86 (td, J=7.4, 1.0 Hz, 1H), 6.76 (d, J=7.8 Hz, 1H), 4.60 (d, J=4.7 Hz, 1H), 4.59-4.53 (m, 2H), 4.21 (dd, J=9.0, 6.7 Hz, 1H), 3.47-3.38 (m, 1H), 2.94-2.89 (m, 1H), 2.59 (dd, J=9.0, 4.9 Hz, 1H), 1.91-1.84 (m, 2H), 1.71 (dd, J=12.0, 9.1 Hz, 1H), 1.64-1.42 (m, 5H).

LCMS Method A: (M+H) 314.2; Rt 1.57 min

Example 2: [(1R)-2-(1-benzofuran-3-yl)-1-{[(1S,2R,4R)-7-oxabicyclo[2.2.1]heptan-2-yl]formamido}ethyl]boronic Acid (Compound No. 9)

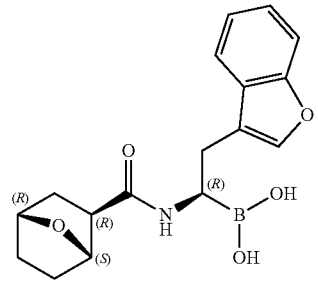

Step 1: (1S,2R,4R)-7-Oxa-bicyclo[2.2.1]heptane-2-carboxylic Acid [(R)-2-(benzofuran-3-yl)-1-((1S,2S,6R,8S)-2,9,9-trimethyl-3,5-dioxa-4-bora-tricyclo[6.1.1.0$^{2,6}$]dec-4-yl)-ethyl]-amide

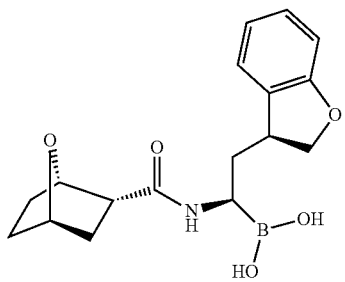

To a solution of (1S,2R,4R)-7-Oxa-bicyclo[2.2.1]heptane-2-carboxylic acid (1.87 g; 13.18 mmol), [Dimethyl-amino-([1,2,3]triazolo[4,5-b]pyridin-3-yloxy)-methylene]-dimethyl-ammonium hexafluoro phosphate (HATU) (4.62 g; 14.37 mmol) and 4-Methyl-morpholine (3.29 ml; 29.94 mmol) in 70 ml dry DMF is added under ice cooling and argon atmosphere (R)-2-(benzofuran-3-yl)-1-((1S,2S,6R,8S)-2,9,9-trimethyl-3,5-dioxa-4-boratricyclo[6.1.1.0$^{2,6}$]dec-4-yl)-ethylamine hydrochloride (4.50 g; 11.98 mmol). The yellow solution is stirred for 2.5 h at rt. The reaction mixture is poured into 500 ml ice cooled, saturated NaHCO$_3$-solution and stirred for 15 min. The precipitate is collected by vacuum-filtration and washed with water. The obtained solid is triturated with acetonitrile, diluted with MTB-ether, and sucked off to yield (1S,2R,4R)-7-Oxa-bicyclo[2.2.1]heptane-2-carboxylic acid [(R)-2-(benzofuran-3-yl)-1-((1S, 2S,6R,8S)-2,9,9-trimethyl-3,5-dioxa-4-bora-tricyclo[6.1.1.0²,⁶]dec-4-yl)-ethyl]-amide (3.26 g, yield: 58.8%) as white solid (purity 100%).

LCMS Method A: (M+H) 464.2; Rt 2.57 min

Step 2: [(1R)-2-(1-benzofuran-3-yl)-1-{[(1S,2R,4R)-7-oxabicyclo[2.2.1]heptan-2-yl]formamido}ethyl]boronic Acid

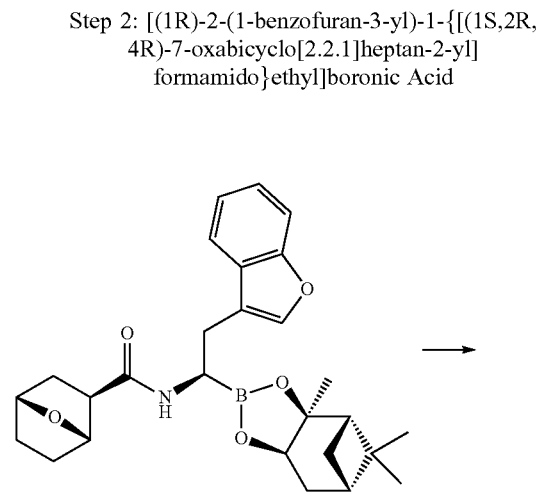

To a two phase system of (1S,2R,4R)-7-Oxa-bicyclo[2.2.1]heptane-2-carboxylic acid [(R)-2-benzofuran-3-yl-1-((1S,2S,6R,8S)-2,9,9-trimethyl-3,5-dioxa-4-bora-tricyclo[6.1.1.0²,⁶]dec-4-yl)-ethyl]-amide (ee=97%, 3.45 mmol; 1.60 g) in 150 ml n-pentane and 50 ml methanol is added at 0° C. isobutylboronic acid (13.81 mmol; 1.41 g) and 1N Hydrochloric acid (15.54 mmol; 15.54 ml). The reaction is stirred at rt overnight. The pentane phase is separated and the methanolic phase is washed with pentane (3×80 mL). The methanolic phase is concentrated (bath temp below 30° C.) in vacuo, diluted with ice water and alkalized with 1 N NaOH (pH 11-12). This basic solution is extracted with DCM (3×80 mL). The aqueous phase is acidified with 1 N HCl (pH 2) and extracted with DCM (5×80 mL) again. The combined organic phases are dried over Na₂SO₄, filtrated and evaporated. The residue is solved in acetonitrile/water and lyophilized to give 0.697 g (yield 61.3%) of the title compound as white solid.

Analytical data: see Table 2

Example 3: [(1R)-2-(7-chloro-1-benzofuran-3-yl)-1-{[(1S,2R,4R)-7-oxabicyclo[2.2.1]heptan-2-yl]formamido}ethyl]boronic Acid (Compound No. 13)

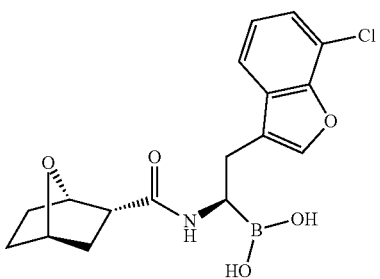 [SMILES: O=C(N[C@@H](Cc1coc2c(Cl)cccc12)B(O)O)[C@@H]1C[C@H]2CC[C@@H]1O2]

Step 1: (1S,2R,4R)-7-Oxa-bicyclo[2.2.1]heptane-2-carboxylic Acid [(R)-2-(7-chloro-benzofuran-3-yl)-1-((1S,2S,6R,8S)-2,9,9-trimethyl-3,5-dioxa-4-bora-tricyclo[6.1.1.0²⁶]dec-4-yl)-ethyl]-amide To a solution of (1S,2R,4R)-7-Oxa-bicyclo[2.2.1]heptane-2-carboxylic acid (3.77 g; 26.55 mmol), [Dimethylamino-([1,2,3]triazolo[4,5-b]pyridin-3-yloxy)-methylene]-dimethyl-ammonium hexafluoro phosphate (HATU) (9.30 g; 28.97 mmol) and 4-Methyl-morpholine (6.63 ml; 60.34 mmol) in dry 148 ml DMF is added under ice cooling and argon atmosphere (R)-2-(7-Chloro-benzofuran-3-yl)-1-((1S,2S,6R,8S)-2,9,9-trimethyl-3,5-dioxa-4-bora-tricyclo[6.1.1.0²,⁶]dec-4-yl)-ethylamine hydrochloride (9.90 g; 24.14 mmol). The yellow solution is stirred for 3 h at rt. The reaction mixture is poured into 1 l ice cooled, saturated NaHCO₃-solution and stirred for 15 min. The precipitate is collected by vacuum-filtration and washed with water. The obtained solid is triturated with acetonitrile, diluted with MTB-ether, and sucked off to yield (1S,2R,4R)-7-Oxa-bicyclo[2.2.1]heptane-2-carboxylic acid [(R)-2-(7-chloro-benzofuran-3-yl)-1-((1S,2S,6R,8S)-2,9,9-trimethyl-3,5-di-oxa-4-bora-tricyclo[6.1.1.0$^{2,6}$]dec-4-yl)-ethyl]-amide (6.9 g, yield: 56.6%) as white solid (purity 95%).

LCMS Method A: (M+H) 498.2; Rt 2.70 min

Step 2: [(1R)-2-(7-chloro-1-benzofuran-3-yl)-1-{[(1S,2R,4R)-7-oxabicyclo[2.2.1]heptan-2-yl]formamido}ethyl]boronic Acid (Compound No. 13)

To a two phase system of (1S,2R,4R)-7-Oxa-bicyclo[2.2.1]heptane-2-carboxylic acid [(R)-2-(7-chloro-benzo-furan-3-yl)-1-((1S,2S,6R,8S)-2,9,9-trimethyl-3,5-dioxa-4-bora-tricyclo[6.1.1.0$^{2,6}$]dec-4-yl)-ethyl]-amide (ee=99%, 12.39 mmol; 6.26 g) in 220 ml n-pentane and 125 ml methanol is added at 0° C. isobutylboronic acid (37.17 mmol; 3.79 g) and 1N Hydrochloric acid (55.760 mmol; 55.760 ml). The reaction is stirred at rt overnight. The pentane phase is separated and the methanolic phase is washed with pentane (3×200 mL). The methanolic phase is concentrated (bath temp below 30° C.) in vacuo, diluted with 200 mL ice water and alkalized with 1 N NaOH (pH 12-13). This basic solution is extracted with DCM (3×200 mL). The aqueous phase is acidified with 1 N HCl (pH 2-3) and extracted with DCM (5×220 mL) again. The combined organic phases are dried over Na$_2$SO$_4$, filtrated and evaporated. The residue is solved in acetonitrile/water and lyophilized to give 3.277 g of the title compound as white solid.

$^1$H NMR (500 MHz, DMSO-d$_6$/D$_2$O) d 7.78 (s, 1H), 7.64-7.60 (m, 1H), 7.42-7.39 (m, 1H), 7.29 (t, J=7.8 Hz, 1H), 4.54-4.50 (m, 1H), 4.48-4.45 (m, 1H), 3.15-3.09 (m, 1H), 2.89 (dd, J=14.9, 5.8 Hz, 1H), 2.77 (dd, J=14.9, 8.4 Hz, 1H), 2.50 (dd, J=9.0, 4.9 Hz, 1H), 1.82-1.75 (m, 1H), 1.65 (dd, J=11.9, 9.0 Hz, 1H), 1.58-1.49 (m, 2H), 1.49-1.39 (m, 2H).

Waters XBridge C8 3.5 µm 4.6×50 mm (A19/533—La Chrom Elite; 70173815); 8.1 min; 2 mL/min; 215 nm; buffer A: 0.05% TFA/H2O; buffer B: 0.04% TFA/ACN; 0.0-0.2 min 5% buffer B; 0.2-8.1 min 5%-100% buffer B; 8.1-10.0 min 100%-5% buffer B: %; Rt 4.24 min.

UPLC MS Waters Acquity UPLC; CORTECS C18 1.6 µm 50-2.1 mm; A: H2O+0.05% HCOOH; B: MeCN+0.04% HCOOH; T: 30° C.; Flow: 0.9 ml/min; 2%≥ 100% B: 0≥1.0 min; 100% B: 1.0-≥1.3 min: 346.1 [M+H−H$_2$O]; RT 0.61 min.

Starting from commercial available acids (or acids synthetised by saponification of commercial available esters) or acids described in the literature the following compounds have been synthetised according to example 1 or 2 steps 1 and 2:

TABLE 1

List of exemplary compounds

| Compound No. | Structure | Name |
|---|---|---|
| 1 | 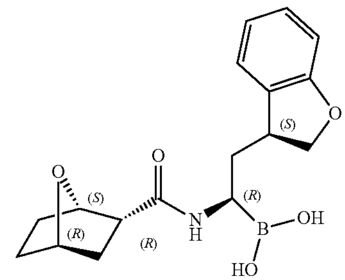 | [(1R)-2-[(3S)-2,3-dihydro-1-benzofuran-3-yl]-1-{[(1S,2R,4R)-7-oxabicyclo[2.2.1]heptan-2-yl]formamido}ethyl]boronic acid |
| 2 | 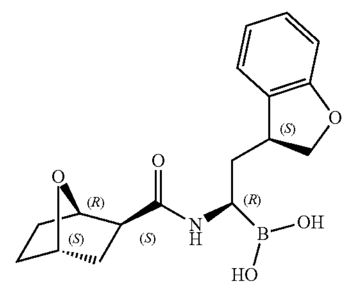 | [(1R)-2-[(3S)-2,3-dihydro-1-benzofuran-3-yl]-1-{[(1R,2S,4S)-7-oxabicyclo[2.2.1]heptan-2-yl]formamido}ethyl]boronic acid |
| 3 | 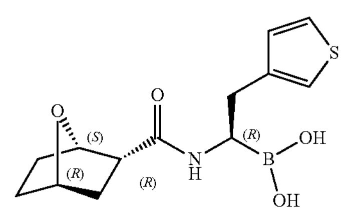 | [(1R)-1-{[(1S,2R,4R)-7-oxabicyclo[2.2.1]heptan-2-yl]formamido}-2-(thiophen-3-yl)ethyl]boronic acid |
| 4 | 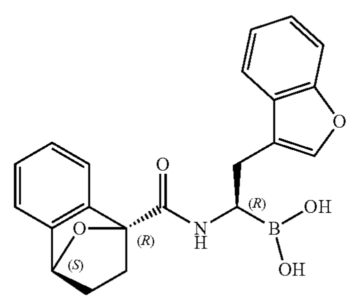 | [(1R)-2-(1-benzofuran-3-yl)-1-{[(1R,8S)-11-oxatricyclo[6.2.1.0$^{2,7}$]undeca-2(7),3,5-trien-1-yl]formamido}ethyl]boronic acid |
| 5 | 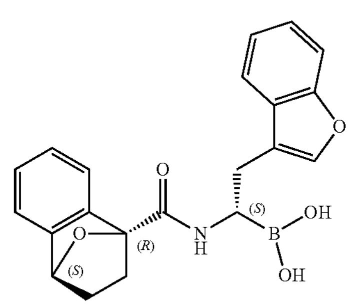 | [(1S)-2-(1-benzofuran-3-yl)-1-{[(1R,8S)-11-oxatricyclo[6.2.1.0$^{2,7}$]undeca-2(7),3,5-trien-1-yl]formamido}ethyl]boronic acid |

TABLE 1-continued

List of exemplary compounds

| Compound No. | Structure | Name |
|---|---|---|
| 6 | 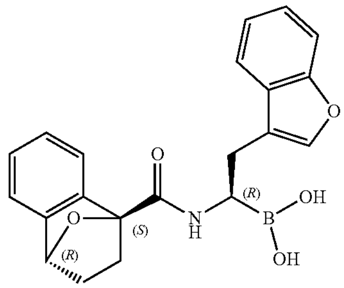 | [(1R)-2-(1-benzofuran-3-yl)-1-{[(1S,8R)-11-oxatricyclo[6.2.1.0²,⁷]undeca-2(7),3,5-trien-1-yl]formamido}ethyl]boronic acid |
| 7 | 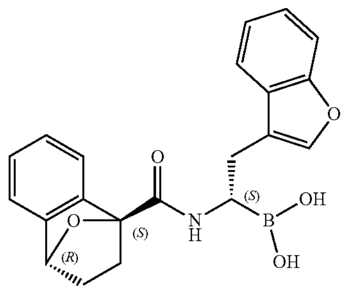 | [(1S)-2-(1-benzofuran-3-yl)-1-{[(1S,8R)-11-oxatricyclo[6.2.1.0²,⁷]undeca-2(7),3,5-trien-1-yl]formamido}ethyl]boronic acid |
| 8 | 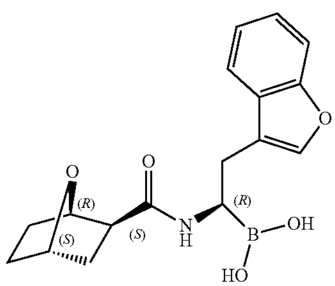 | [(1R)-2-(1-benzofuran-3-yl)-1-{[(1R,2S,4S)-7-oxabicyclo[2.2.1]heptan-2-yl]formamido}ethyl]boronic acid |
| 9 | 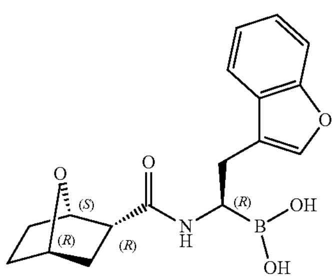 | [(1R)-2-(1-benzofuran-3-yl)-1-{[(1S,2R,4R)-7-oxabicyclo[2.2.1]heptan-2-yl]formamido}ethyl]boronic acid |
| 10 | 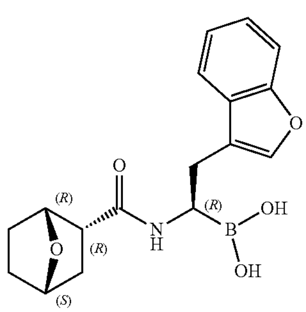 | [(1R)-2-(1-benzofuran-3-yl)-1-{[(1R,2R,4S)-7-oxabicyclo[2.2.1]heptan-2-yl]formamido}ethyl]boronic acid |
| 11 | | [(1S)-2-(1-benzofuran-3-yl)-1-{[(1R,2R,4S)-7-oxabicyclo[2.2.1]heptan-2-yl]formamido}ethyl]boronic acid |
| 12 | | [(1R)-2-(7-chloro-1-benzofuran-3-yl)-1-{[(1R,2S,4S)-7-oxabicyclo[2.2.1]heptan-2-yl]formamido}ethyl]boronic acid |
| 13 | | [(1R)-2-(7-chloro-1-benzofuran-3-yl)-1-{[(1S,2R,4R)-7-oxabicyclo[2.2.1]heptan-2-yl]formamido}ethyl]boronic acid |
| 14 | | [(1R)-2-[(3R)-7-methyl-2,3-dihydro-1-benzofuran-3-yl]-1-{[(1S,2R,4R)-7-oxabicyclo[2.2.1]heptan-2-yl]formamido}ethyl]boronic acid |
| 15 | | [(1R)-2-[(3S)-7-methyl-2,3-dihydro-1-benzofuran-3-yl]-1-{[(1S,2R,4R)-7-oxabicyclo[2.2.1]heptan-2-yl]formamido}ethyl]boronic acid |

TABLE 1-continued

List of exemplary compounds

| Compound No. | Structure | Name |
|---|---|---|
| 16 | 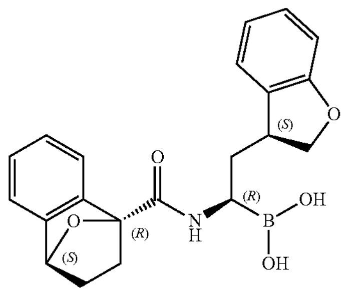 | [(1R)-2-[(3S)-2,3-dihydro-1-benzofuran-3-yl]-1-{[(1R,8S)-11-oxatricyclo[6.2.1.0²,⁷]undeca-2(7),3,5-trien-1-yl]formamido}ethyl]boronic acid |
| 17 | 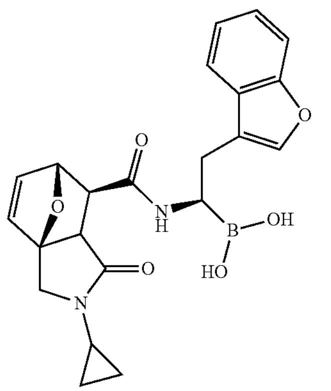 [SMILES: O=C(N[C@@H](Cc1coc2ccccc12)B(O)O)[C@H]1C2C(=O)N(C3CC3)C[C@]23C=C[C@H]1O3] | [(1R)-2-(1-benzofuran-3-yl)-1-{[(1S,6S,7R)-3-cyclopropyl-4-oxo-10-oxa-3-azatricyclo[5.2.1.0¹,⁵]dec-8-en-6-yl]formamido}ethyl]boronic acid |
| 18 | 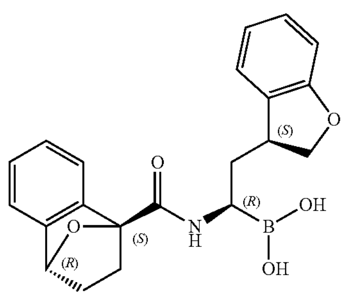 | [(1R)-2-[(3S)-2,3-dihydro-1-benzofuran-3-yl]-1-{[(1S,8R)-11-oxatricyclo[6.2.1.0²,⁷]undeca-2(7),3,5-trien-1-yl]formamido}ethyl]boronic acid |
| 19 | 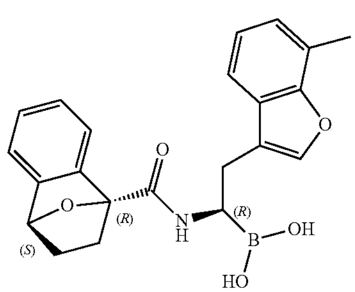 | [(1R)-2-(7-methyl-1-benzofuran-3-yl)-1-{[(1R,8S)-11-oxatricyclo[6.2.1.0²,⁷]undeca-2,4,6-trien-1-yl]formamido}ethyl]boronic acid |
| 20 | 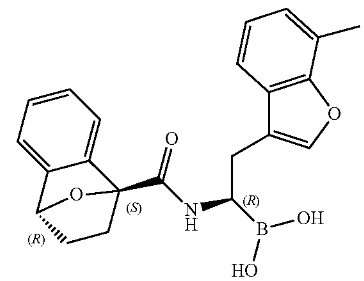 | [(1R)-2-(7-methyl-1-benzofuran-3-yl)-1-{[(1S,8R)-11-oxatricyclo[6.2.1.0²,⁷]undeca-2,4,6-trien-1-yl]formamido}ethyl]boronic acid |
| 21 | 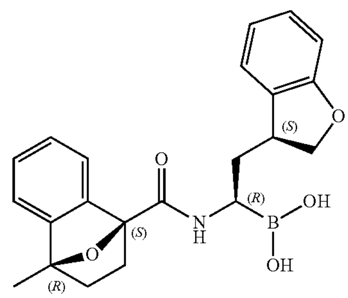 | [(1R)-2-[(3S)-2,3-dihydro-1-benzofuran-3-yl]-1-{[(1S,8R)-8-methyl-11-oxatricyclo[6.2.1.0²,⁷]undeca-2,4,6-trien-1-yl]formamido}ethyl]boronic acid |
| 22 | 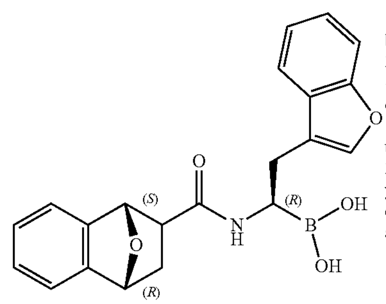 | [(1R)-2-(1-benzofuran-3-yl)-1-{[(1R,8S)-11-oxatricyclo[6.2.1.0²,⁷]undeca-2(7),3,5-trien-9-yl]formamido}ethyl]boronic acid |
| 23 | 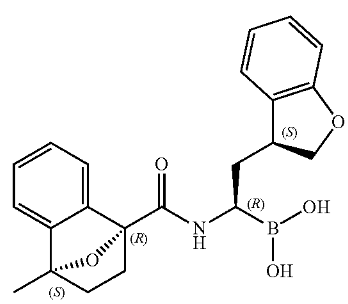 | [(1R)-2-[(3S)-2,3-dihydro-1-benzofuran-3-yl]-1-{[(1R,8S)-8-methyl-11-oxatricyclo[6.2.1.0²,⁷]undeca-2,4,6-trien-1-yl]formamido}ethyl]boronic acid |
| 24 | 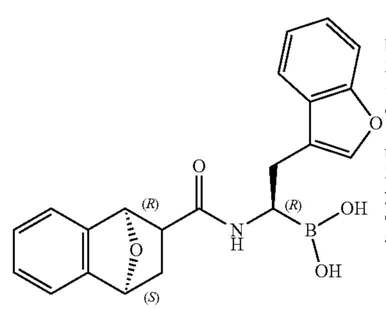 | [(1R)-2-(1-benzofuran-3-yl)-1-{[(1S,8R)-11-oxatricyclo[6.2.1.0²,⁷]undeca-2(7),3,5-trien-9-yl]formamido}ethyl]boronic acid |

TABLE 1-continued

List of exemplary compounds

| Compound No. | Structure | Name |
|---|---|---|
| 25 | 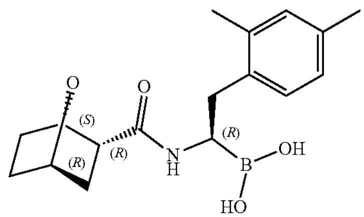 | [(1R)-2-(2,4-dimethylphenyl)-1-{[(1S,2R,4R)-7-oxabicyclo[2.2.1]heptan-2-yl]formamido}ethyl]boronic acid |
| 26 | 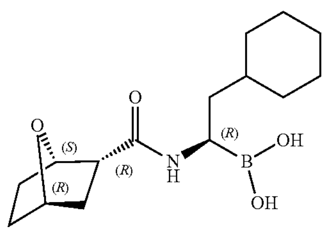 | [(1R)-2-cyclohexyl-1-{[(1S,2R,4R)-7-oxabicyclo[2.2.1]heptan-2-yl]formamido}ethyl]boronic acid |
| 27 | 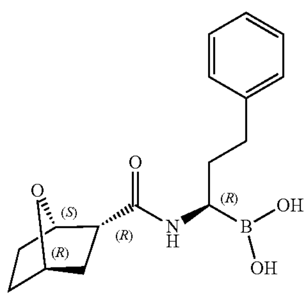 | [(1R)-1-{[(1S,2R,4R)-7-oxabicyclo[2.2.1]heptan-2-yl]formamido}-3-phenylpropyl]boronic acid |
| 28 | 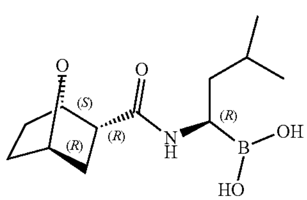 | [(1R)-3-methyl-1-{[(1S,2R,4R)-7-oxabicyclo[2.2.1]heptan-2-yl]formamido}butyl]boronic acid |

TABLE 2

Analytical data

| Compound No. | RET; observed Mass; (LCMS Method) | NMR Signals |
|---|---|---|
| 1 | 3.4 min; 314.18; (Method B) | 1H NMR (500 MHz, DMSO-d$_6$/D$_2$O) d 7.23-7.20 (m, 1H), 7.13-7.09 (m, 1H), 6.86 (td, J = 7.4, 1.0 Hz, 1H), 6.76 (d, J = 7.8 Hz, 1H), 4.60 (d, J = 4.7 Hz, 1H), 4.59-4.53 (m, 2H), 4.21 (dd, J = 9.0, 6.7 Hz, 1H), 3.47-3.38 (m, 1H), 2.94-2.89 (m, 1H), 2.59 (dd, J = 9.0, 4.9 Hz, 1H), 1.91-1.84 (m, 2H), 1.71 (dd, J = 12.0, 9.1 Hz, 2H), 1.64-1.42 (m, 5H). |
| 2 | 3.4 min; 314.18; (Method B) | 1H NMR (400 MHz, DMSO-d$_6$/D$_2$O) d 7.16 (d, J = 7.4 Hz, 1H), 7.09-7.03 (m, 1H), 6.81 (td, J = 74, 1.0 Hz, 1H), 6.70 (d, J = 7.9 Hz, 1H), 4.56 (d, J = 4.4 Hz, 1H), 4.54-4.48 (m, 2H), 4.15 (dd, J = 9.0, 6.7 Hz 1H), 3.41-3.32 (m, 1H), 2.83 (dd, J = 9.8, 5.3 Hz, 1H), 2.55-2.51 (m, 1H), 1.86-1.76 (m, 2H), 1.67 (dd, J = 12.0, 9.1 Hz, 1H), 1.60-1.37 (m, 5H). |
| 3 | 2.46 min; 278.16; (Method B) | 1H NMR (400 MHz, DMSO-d$_6$/D$_2$O) d 7.37-7.33 (m, 1H), 7.06-7.03 (m, 1H), 6.92 (d, J = 5.0 Hz, 1H), 4.51-4.40 (m, 2H), 3.08-2.99 (m, 1H), 2.83-2.74 (m, H), 2.69 (dd, J = 14.5, 8.2 Hz, 1H), 2.49-2.43 (m, 1H), 1.78-1.69 (m, 1H), 1.66-1.57 (m, 1H), 1.53-1.36 (m, 4H). |
| 4 + 5 (mixture of diastereomers, 2:1 R:S at C*-B(OH)$_2$) | 5.42 min; 360.2; (Method B) | — |
| 6 + 7 (mixture of diastereomers, 2:1 R:S at C*-B(OH)$_2$) | 5.26 min; 360.2; (Method B) | — |
| 8 | 3.38 min; 312.16; (Method B) | 1H NMR (400 MHz, DMSO-d$_6$/D$_2$O) d 7.60 (s, 1H), 7.58 (d, J = 7.5 Hz, 1H), 7.47 (d, J = 8.0 Hz, 1H), 7.27 (t, J = 7.6 Hz, 1H), 7.21 (t, J = 7.4 Hz, 1H), 4.50-4.43 (m, 2H), 3.11-3.05 (m, 1H), 2.84 (dd, J = 14.9, 5.9 Hz, 1H), 2.73 (dd, J = 14.9, 8.1 Hz, 1H), 2.45 (dd, J = 9.0, 5.0 Hz, 1H), 1.77-1.69 (m, 1H), 1.61 (dd, J = 12.0, 9.0 Hz, 1H), 1.53-1.44 (m, 2H), 1.44-1.34 (m, 2H). |
| 9 | 3.39 min; 312.16; (Method B) | 1H NMR (500 MHz, DMSO-d$_6$/D$_2$O) d 7.61 (s, 1H), 7.59 (d, J = 7.7 Hz, 1H), 7.48 (d, J = 8.1 Hz, 1H), 7.29-7.25 (m, 1H), 7.24-7.19 (m, 1H), 4.48-4.45 (m, 1H), 4.42-4.40 (m, 1H), 3.12-3.08 (m, 1H), 2.84 (dd, J = 14.9, 5.9 Hz, 1H), 2.73 (dd, J = 14.9, 8.3 Hz, 1H), 2.45 (dd, J = 9.1, 4.9 Hz, 1H), 1.76-1.71 (m, 1H), 1.60 (dd, J = 11.9, 9.1 Hz, 1H), 1.52-1.44 (m, 2H), 1.43-1.34 (m, 2H), |
| 10 + 11 (mixture of diastereomers, 2:1 R:S at C*-B(OH)$_2$) | 3.59 min; 312.16; (Method B) | — |
| 12 | 4.25 min; 346.6; (Method B) | 1H NMR (500 MHz, DMSO-d$_6$/D$_2$O) d 7.78 (s 1H) 7.63-7.60 (m, 1H), 7.42-7.39 (m, 1H), 7.29 (t, J = 7.8 Hz, 1H), 4.56-4.48 (m, 2H), 3.13-3.07 (m, 1H), 2.88 (dd, J = 14.7, 5.8 Hz, 1H), 2.78 (dd, J = 14.9, 8.3 Hz, 1H), 2.53-2.48 (m, 1H), 1.81-1.74 (m, 1H), 1.66 (dd, J = 11.7, 9.3 Hz, 1H), 1.59-1.50 (m, 2H), 1.49-1.40 (m, 2H). |
| 13 | 4.25 min; 346.6; (Method B) | 1H NMR (500 MHz, DMSO-d$_6$/D$_2$O) d 7.78 (s, 1H), 7.64-7.60 (m, 1H), 7.42-7.39 (m, 1H), 7.29 (1, J = 7.8 Hz, 1H), 4.54-4.50 (m, 1H), 4.48-4.45 (rn, 1H), 3.15-3.09 (m, 1H), 2.89 (dd, J = 14.9, 5.8 Hz, 1H), 2.77 (dd, J = 14.9, 8.4 Hz. 1H), 2.50 (dd, J = 9.0, 4.9 Hz, 1H), 1.82-1.75 (m, 1H), 1.65 (dd, J = 11.9, 9.0 Hz, 1H), 1.58-1.49 (m, 2H), 1.49-1.39 (m, 2H). |
| 14 | 3.8 min; 328.2; (Method B) | 1H NMR (400 MHz, DMSO-d$_6$/D$_2$O) d 7.02 (d, J = 7.3 Hz, 1H), 6.89 (d, J = 7.5 Hz, 1H), 6.71 (t, J = 7.4 Hz, 1H), 4.58-4.49 (m, 3H), 4.09 (dd, J = 8.9, 6.6 Hz, 1H), 3.41-3.30 (m, 1H), 2.81 (t, J = 7.6 |

TABLE 2-continued

Analytical data

| Compound No. | RET; observed Mass; (LCMS Method) | NMR Signals |
|---|---|---|
| | | Hz, 1H), 2.57-2.50 (m, 1H), 2.07 (s, 3H), 1.90-1.77 (m, 2H), 1.65 (dd, J = 12.0, 9.1 Hz, 1H), 1.61-1.36 (m, 5H). |
| 15 | 3.8 min; 328.2; (Method B) | 1H NMR (400 MHz, DMSOd$_6$/D$_2$O) d 6.97 (d, J = 7.3 Hz, 1H), 6.89 (d, J = 7.4 Hz, 1H), 6.72 (t, J = 7.4 Hz, 1H), 4.58-4.48 (m, 3H), 4.17 (dd, J = 9.0, 6.8 Hz, 1H), 3.41-3.32(m, 1H), 2.99 (dd, J = 10.2, 4.7 Hz, 1H), 2.64-2.50 (m, 1H), 2.08 (s, 3H), 1.93-1.79 (m, 2H), 1.64-1.37 (m, 6H). |
| 16 | 5.0 min; 362.22; (Method B) | 1H NMR (400 MHz, DMSO-d$_6$/D$_2$O) d 7.34-7.29 (m, 2H), 7.21-7.13 (m, 3H), 7.09-7.04 (m, 1H), 6.82 (td, J = 7.4, 1.0 Hz, 1H), 6.71 (d, J = 7.9 Hz, 1H), 5.52 (d, J = 4.9 Hz, 1H), 4.57 (1, J = 8.9 Hz, 1H), 4.21 (d, J = 9.1, 6.9 Hz, 1H), 3.39-3.29 (m, 2H), 2.19-2.08 (m, 1H), 2.01-1.87 (m, 2H), 1.70-1.55(m, 2H), 1.37-1.29 (m, 1H). |
| 17 | 4.02 min; 405.24; (Method B) | 1H NMR (400 MHz, DMSO-d$_6$/D$_2$O) d 7.65-7.57 (m, 2H), 7.47 (d, J = 8.0 Hz, 1H), 7.30-7.24 (m, 1H), 7.24-7.19 (m, 1H), 6.51 (dd, J = 6.8, 5.7 Hz, 1H), 6.36-6.32 (m, 1H), 4.85-4.75 (m, 1H), 3.91 (dd, J = 12.0, 9.7 Hz, 1H), 3.42 (dd, J = 12.0, 5.0 Hz, 1H), 3.17-3.07 (m, 1H), 2.95-2.83 (m, 1H), 2.83-2.70 (m, 2H), 2.57-2.52 (m, 1H), 2.44 (dd, J = 13.4, 9.2 Hz, 1H), 0.65-0.46 (m, 4H). |
| 18 | 5.1 min; 362.22; (Method B) | 1H NMR (400 MHz, DMSO-d$_6$/D$_2$O) d 7.33-7.27 (m, 2H), 7.17 (td, J = 7.3, 1.4 Hz, 1H), 7.13 (td, J = 7.4, 1.4 Hz, 1H), 7.08-7.01 (m, 2H), 6.76 (t, J = 7.4 Hz, 1H), 6.69 (d, J = 7.8 Hz, 1H), 5.53 (d, J = 5.0 Hz, 1H), 4.55 (t, J = 9.0 Hz, 1H), 4.20 (dd, J = 9.1, 6.9 Hz, 1H), 3.43 (m, 10.5, 4.1 Hz, 1H), 3.32-3.22 (m, 1H), 2.19-2.08 (m, 1H). 1.98-1.84 (m, 2H), 1.69-1.53 (m, 2H), 1.38-1.28 (m, 1H). |
| 19 | 5.44 min; 374.23; (Method B) | 1H NMR (500 MHz, DMSO-d$_6$) d 7.61 (s, 1H), 7.48-7.44 (m, 1H), 7.35-7.31 (m, 2H), 7.22 (td, J = 7.4, 1.4 Hz, 1H), 7.19 (td, J = 7.4, 1.3 Hz, 1H), 7.16-7.11 (m, 2H), 5.50 (d, J = 5.0 Hz, 1H), 3.58 (dd, J = 7.3, 5.5 Hz, 1H), 3.08 (dd, J = 14.8, 5.4 Hz, 1H), 2.93 (dd, J = 14.8, 7,4 Hz, 1H), 2.45 (s, 3H), 2.14-2.07 (m, 1H), 1.80 (td, J = 11.0, 3.9 Hz, 1H), 1.60-1.53 (m, 1H), 1.38-1.32 (m, 1H). |
| 20 | 5.41 min; 374.23; (Method B) | 1H NMR (400 MHz, DMSO-d$_6$) d 7.46 (s, 1H), 7.36-7.32 (m, 2H), 7.27-7.16 (m, 3H), 7.06 (d, J = 7.3 Hz, 1H), 6.93 (t, J = 7.5 Hz, 1H), 5.50 (d, J = 5.0 Hz, 1H), 3.68-3.63 (m, 1H), 3.07 (dd, J = 14.9, 5.5 Hz, 1H), 2.91 (dd, J = 14.9, 7.1 Hz, 1H), 2.40 (s, 3H), 2.19-2.10 (m, 1H), 1,94 (td, J = 11.1, 3.8 Hz, 1H), 1.65-1.57 (m, 1H), 1.40-1.32 (m, 1H). |
| 21 | 5.3 min; 376.25; (Method B) | 1H NMR (400 MHz, DMSO-d$_6$/D$_2$O) d 7.29-7.23 (m, 2H), 7.20 (td, J = 7.3, 1.2 Hz, 1H) 7.14 (td, J = 7.3, 1.4 Hz, 1H), 7.09-7.01 (m, 2H), 6.76 (td, J = 7.4, 1.0 Hz, 1H), 6.69 (d, J = 7.9 Hz, 1H), 4.57 (t, J = 9.0 Hz, 1H), 4.22 (dd, J = 9.2, 6.9 Hz, H), 3.43 (dd, J = 10.6, 4.1 Hz, 1H), 3.33-3.22 (m, 1H), 2.11-2.02 (m, 1H), 1.94-1.84 (m, 2H), 1.80 (s, 3H), 1.70-1.58 (m, 2H), 1.46-1.38 (m, 1H). |
| 22 | 4.23 min, 360.2; (Method B) | 1H NMR (400 MHz, DMSO-d$_6$) d 7.52-7.45 (m, 2H), 7.42 (s, 1H), 7.30-7.18 (m, 3H), 7.11-7.06 (m, 1H), 7.03-6.99 (m, 1H), 6.97-6.91 (m, 1H), 5.45 (d, J = 5.2 Hz, 1H), 5.38-5.32 (m, 1H), 3.21-3.14 (m, 1H), 3.09-3.03 (m, 1H), 2.70 (dd, J = 15.4, 6.0 Hz, 1H), 2.61 (dd, J = 14.9, 8.0 Hz, 1H), 2.09 (td, J = 11.4, 5.1 Hz, 1H), 1.52 (dd, J = 11.7, 4.2 Hz, 1H). |
| 23 | 5.3 min; 376.25; (Method B) | 1H NMR (400 MHz, DMSO-d$_6$/D$_2$O d 7.33-7.30 (m, 1H), 7.27-7.13 (m, 4H), 7.10-7.04 (m, 1H), 6.82 (1d, J = 7.4, 1.0 Hz, 1H), 6.71 (d, J = 7.9 Hz, 1H), 4.58 (t, J = 8.9 Hz, 1H), 4.23 (dd, J = 9.1, 6.9 Hz, 1H), 3.41-3.31 (m, 2H), 2.07 (td, J = 10.8, 3.8 Hz, 1H), 2.02-1.85 (m, 2H), 1.80 (s, 3H), 1.72-1.60 (m, 2H), 1.47-1.38 (m, 1H). |
| 24 | 4.31 min; 360.2; (Method B) | 1H NMR (400 MHz, DMSO-d$_6$/D$_2$O) d 7.63 (d, J = 7.6 Hz, 1H), 7.59-7.55 (m, 2H), 7.38-7.32 (m, 1H), 7.31-7.22 (m, 2H), 7.07 (t, J = 7.4 Hz, 1H), 6.75 (t, J = 7.4 Hz, 1H), 6.51 (d, J = 7.3 Hz, 1H), 5.40-5.36 (m, 2H), 3.25-3.18 (m, 1H), 3.07 (dd, J = 9.3, 5.4 Hz, 1H), 2.82 (dd, J = 14.8, 5.5 Hz, 1H), 2.66 (dd, J = 14.9, 9.2 Hz, 1H), 2.14-2.06 (m, 1H), 1.59 (dd, J = 11.6, 4.3 Hz, 1H). |
| 25 | 3.87 min; 300.19; (Method B) | 1H NMR (400 MHz, DMSO-d$_6$) d 7.34 (d, J = 5.9 Hz, 1H), 6.94 (d, J = 7.7 Hz, 1H), 6.91-6.87 (m, 1H), 6.87-6.82 (m, 1H), 4.48-4.44 (m, 1H), 4.41 (d, J = 3.9 Hz, 1H), 3.05-2.97 (m, 1H), 2.71 (dd, J = 14.1,6.1 Hz, 1H), 2.59 (dd, J = 14.2,8.9 Hz, 1H), 2.41 (dd, J = 9.1, 4.9 Hz, 1H), 2.18 (s, 6H), 1.76-1.68 (m, 1H), 1.58 (dd, J = 11.9, 9.0 Hz, 1H), 1.53-1.34 (m, 4H). |
| 26 | 3.78 min; 278.19; (Method B) | 1H NMR (400 MHz, DMSO-d$_6$ + 4-5 drops D$_2$O) d 4.66-4.40 (m, 2H), 2.91 (t, J = 7.4 Hz, 1H), 2.51 (dd, J = 9.1, 5.0 Hz, 1H), 1.91-1.78 (m, 1H), 1.76-1.41 (m, 10H), 1.39-1.02 (m, 6H), 0.95-0.69 (m, 2H). |
| 27 | 3.51 min; 286.17; (Method B) | 1H NMR (400 MHz, DMSO-d$_6$) d 7.34-7.24 (m, 2H), 7.24-7.13 (m, 3H), 4,64-4.49 (m, 2H), 2.82 (t, J = 7.0 Hz, 1H), 2.66-2.48 (m, 3H), 1.97-1.82 (m, 1H), 1.82-1.36 (m, 7H). |
| 28 | 2.64 min; 238.12; (Method B) | 1H NMR (400 MHz, DMSO-d$_6$ + 4-5 drops D$_2$O) d 4.58-4.37 (m, 21-1), 2.88 (dd, J = 9.1, 6.0 Hz, 1H), 2.45 (dd, J = 9.0, 4.9 Hz, 1H), 1.90-1.73 (m, 1H), 1.60 (dd, J = 11.8, 9.1 Hz, 1H), 1.56-1.16 (m, 7H), 0.90-0.68 (m, 6H). |

Biological Activity

Determination of LMP7 Activity:

Measurement of LMP7 inhibition is performed in 384 well format based on fluorescence intensity assay.

Purified human immuno proteasome (0.25 nM) and serial diluted compounds in DMSO (range of concentrations from 30 µM to 15 pM) or controls are incubated for 20 minutes or 120 minutes (long incubation) at 25° C. in assay buffer containing 50 mM Tris pH 7.4, 0.03% SDS, 1 mM EDTA and 1% DMSO. The reaction is initiated by the addition of the fluorogenic peptide substrate, Suc-LLVY-AMC (Bachem 1-1395), at a concentration of 40 µM. After 60 minutes of incubation at 37° C., fluorescence intensity is measured at $\lambda_{ex}$=350 nm and $\lambda_{em}$=450 nm with a fluorescence reader (Perkin Elmer Envision reader or equivalent).

The LMP7 activity of the compounds is summarized in Table 3. Unless indicated otherwise the results are obtained after incubation for 20 minutes.

Determination of Beta5 Activity:

Measurement of Beta5 inhibition is performed in 384 well format based on fluorescence intensity assay.

Purified human constitutive proteasome (1.25 nM) and serial diluted compounds in DMSO (range of concentrations from 30 µM to 15 pM) or controls are incubated for 20 minutes or 120 minutes (long incubation) at 25° C. in assay buffer containing 50 mM Tris pH 7.4, 0.03% SDS, 1 mM EDTA and 1% DMSO. The reaction is initiated by the addition of the fluorogenic peptide substrate, Suc-LLVY-AMC (Bachem 1-1395), at a concentration of 40 µM. After 60 minutes of incubation at 37° C., fluorescence intensity is measured at $\lambda_{ex}$=350 nm and $\lambda_{em}$=450 nm with a fluorescence reader (Perkin Elmer Envision reader or equivalent).

Table 3 shows the Beta5 activity of compounds according to the invention and their selectivity to LMP7 versus Beta5. Unless indicated otherwise the results are obtained after incubation for 20 minutes.

TABLE 3

| Compound No. | LMP7 IC50 (M) | Beta5 IC50 (M) | Selectivity LMP7 vs Beta5 |
|---|---|---|---|
| 1 | **** | * | +++++ |
| 2 | *** | * | +++ |
| 3 | ** | n. m. a. | − |
| 4 + 5 (mixture of diastereomers, 2:1 R:S at C*-B(OH)$_2$) | **** | ** | +++++ |
| 6 + 7 mixture of diastereomers, 2:1 R:S at C*-B(OH)$_2$) | **** | * | +++ |
| 8 | **** | * | ++++ |
| 9 | **** | ** | +++++ |
| 10 + 11 mixture of diastereomers, 2:1 R:S at C*-B(OH)$_2$) | *** | n. m. a. | − |
| 12 | **** | * | +++++ |
| 13 | **** | ** | +++++ |
| 14 | ** | n. m. a. | − |
| 15 | **** | * | +++++ |
| 16 | **** | * | +++++ |
| 17 | **** | * | ++ |
| 18 | **** | * | +++++ |
| 19 | **** | * | +++++ |
| 20 | **** | * | ++++ |
| 21 | **** | * | +++++ |
| 22 | **** | * | ++ |
| 23 | **** | * | +++++ |
| 24 | **** | *** | + |
| 25 | *** | * | ++ |
| 26 | ** (long) | n. m. a. (long) | − |
| 27 | ** | n. m. a. | − |
| 28 | ** | n. m. a. | − |

*: 5 µM < IC$_{50}$ ≤ 3.0*10$^{-5}$M,
**: 0.5 µM < IC$_{50}$ ≤ 5 µM,
***: 0.05 µM < IC$_{50}$ ≤ 0.5 µM,
****: IC$_{50}$ < 0.05 µM,
+: Selectivity <100,
++: 100 ≤ Selectivity < 300,
+++: 300 ≤ Selectivity < 500,
++++: 500 ≤ Selectivity < 700,
+++++: Selectivity ≥700,
n. m. a.: no measurable the given concentration range; in accordance with the method described above, "long incubation" means that the sample is incubated for 120 min.

The following examples relate to medicaments:

Example A: Injection Vials

A solution of 100 g of an active ingredient of the formula (I) and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B: Suppositories

A mixture of 20 g of an active ingredient of the formula (I) with 100 g of soya lecithin and 1400 g of cocoa butter is melted, poured into moulds and allowed to cool. Each suppository contains 20 mg of active ingredient.

Example C: Solution

A solution is prepared from 1 g of an active ingredient of the formula I, 9.38 g of NaH$_2$PO$_4$ 2H$_2$O, 28.48 g of Na$_2$HPO$_4$. 12 H$_2$O and 0.1 g of benzalkonium chloride in 940 ml of bidistilled water. The pH is adjusted to 6.8, and the solution is made up to 1 l and sterilised by irradiation. This solution can be used in the form of eye drops.

Example D: Ointment 500 mg of an active ingredient of the formula (I) are mixed with 99.5 g of Vaseline under aseptic conditions.

Example E: Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F: Dragees

Tablets are pressed analogously to Example E and subsequently coated in a conventional manner with a coating of sucrose, potato starch, talc, tragacanth and dye.

Example G: Capsules 2 kg of active ingredient of the formula (I) are introduced into hard gelatine capsules in a conventional manner in such a way that each capsule contains 20 mg of the active ingredient.

Example H: Ampoules

A solution of 1 kg of active ingredient of the formula (I) in 60 l of bidistilled water is sterile filtered, transferred into ampoules, lyophilised under sterile conditions and sealed under sterile conditions. Each ampoule contains 10 mg of active ingredient.

The invention claimed is:

1. A method for treatment of an immunoregulatory abnormality or a cancer, the method comprising:
   administering a compound of formula (I) tautomer, or stereoisomer thereof, as well as a pharmaceutically acceptable salt of each of the foregoing, including a mixture thereof in all ratios, to a patient in need thereof, (I)

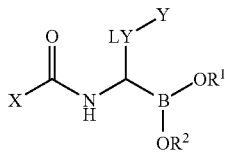

wherein in the compound of formula (I):

LY denotes $(CH_2)_m$, wherein 1 to 4H atoms may be replaced by at least one selected from the group consisting of Hal, $R^{3a}$, and $OR^{4a}$; and/or wherein one $CH_2$ group may be replaced by O, S, SO, or $S_2$;

X denotes a heterobicycle or heterotricycle of formula (xa), (xb), (xc), (xd), (xe), (xf), (xg), (xh), or (xi); each, independently from one another, unsubstituted or mono-, di-, or trisubstituted by at least one selected from the group consisting of Hal, $NO_2$, CN, $R^{5a}$, $OR^{5a}$, $CONR^{5a}R^{5b}$, $NR^{5a}COR^{5b}$, $SO_2R^{5a}$, $SOR^{5a}$, $SO_2NR^{5a}R^{5b}$, $NR^{5a}SO_2R^{5b}$, $NR^{5a}R^{5b}$, $(CH_2)_q$—$R^6$, $COR^{5a}$ and/or $SO_2R^{5a}$; and wherein 1, 2 or 3 of the cyclic $CH_2$ groups may be replaced by at least one selected from the group consisting of $CR^{4a}R^{4b}$, C=O, O, S, $NR^{5a}$, SO and/or $SO_2$;

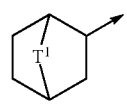 (xa)

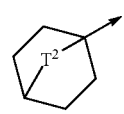 (xb)

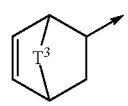 (xc)

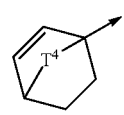 (xd)

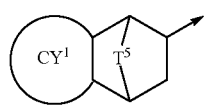 (xe)

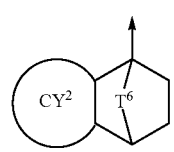 (xf)

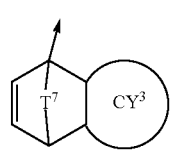 (xg)

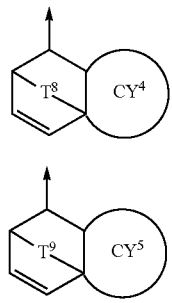

(xh)

(xi)

Y denotes $P^1$, $P^2$, or $P^3$;

$P^1$ denotes a linear or branched $C_1$-$C_6$-alkyl or $C_3$-$C_8$-cycloalkyl, each, independently from one another, unsubstituted or mono-, di-, tri-, or tetrasubstituted by at least one selected from the group consisting of Hal, CN, $R^{3a}$, $OR^{3a}$, and $(CH_2)_q$—$R^6$;

$P^2$ denotes phenyl or an aromatic monocyclic 5-, 6-, or 7-membered heterocycle, each unsubstituted or mono-, di-, tri-, tetra-, or pentasubstituted by at least one selected from the group consisting of Hal, CN, $R^{3a}$, OH, $OR^{3a}$, $CONR^{4a}R^{4b}$, $NR^{3a}COR^{3b}$, $SO_2R^{3a}$, $SOR^{3a}$, $NR^{4a}R^{4b}$, $Ar^2$, $Het^2$, $(CH_2)_q$—$SR^{3a}$, $(CH_2)_q$—$N(R^{4a})_2$, and $(CH_2)_q$—$R^6$, wherein the heterocycle of $P^2$ contains 1, 2, or 3 of N, O, and/or S atoms;

$P^3$ denotes a bicyclic 8-, 9-, or 10-membered hydrocarbon or heterocycle, each independently from one another unsubstituted or mono-, di-, tri tetra-, or pentasubstituted by at least one selected from the group consisting of Hal, CN, $R^{3a}$, OH, $OR^{3a}$, $CONR^{4a}R^{4b}$, $NR^{3a}COR^{3b}$, $SO_2R^{3a}$, $SOR^{3a}$, $NR^{4a}R^{4b}$, $Ar^2$, $Het^2$, $(CH_2)_q$—$SR^{3a}$, $(CH_2)_q$—$N(R^{4a})_2$, and $(CH_2)_q$—$R^6$, wherein at least one ring of the bicyclic hydrocarbon or heterocycle is aromatic, and wherein the heterocycle of $P^3$ contains 1, 2, or 3 of N, O, and/or S atoms;

$Cy^1$, $Cy^2$, $Cy^3$, $Cy^4$ and $Cy^5$ denote each, independently from one another, $Ar^1$ or $Het^1$;

$R^1$ and $R^2$ denote each, independently from one another, H or $C_1$-$C_6$-alkyl, or $R^1$ and $R^2$ form together a residue according to formula (CE):

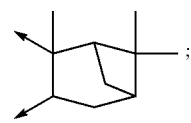

CE $R^{3a}$ and $R^{3b}$ denote each, independently from one another, linear or branched $C_1$-$C_6$-alkyl or $C_3$-$C_8$ cycloalkyl, wherein 1 to 5H atoms may be replaced by at least one selected from the group consisting of Hal, CN, OH, and OAlk;

$R^{4a}$ and $R^{4b}$ denote each, independently from one another, H or $R^{3a}$; or $R^{4a}$ and $R^{4b}$ form together a $C_3$-$C_8$ alkylene group;

$R^{5a}$ and $R^{5b}$ denote each, independently from one another, H, $R^{3a}$, $Ar^2$, or $Het^2$;

$R^6$ denotes OH or $OR^{3a}$;

$T^1$, $T^2$, $T^3$, $T^4$, $T^5$, $T^6$, $T^7$, $T^8$, and $T^9$ denote each, independently from one another, O, SO, or C=O;

Alk denotes linear or branched $C_1$-$C_6$-alkyl;

$Ar^1$ represents an aromatic 6-membered carbocycle;

$Het^1$ represents a saturated, unsaturated, or aromatic 5- or 6-membered heterocycle having 1 to 4 of N, O, and/or S atoms;

$Ar^2$ denotes phenyl, which is unsubstituted or mono- or disubstituted by at least one selected from the group consisting of Hal, $NO_2$, CN, $R^{3a}$, $OR^{3a}$, $CONHR^{3a}$, $NR^{3a}COR^{3b}$, $SO_2R^{3a}$, $SOR^{3a}$, $NH_2$, $NHR^{3a}$, $N(R^{3a})_2$, and $(CH_2)_q$—$R^6$;

$Het^2$ denotes a saturated, unsaturated, or aromatic 5- or 6-membered heterocycle having 1 to 4 of N, O, and/or S atoms; which is unsubstituted or mono- or disubstituted by at least one selected from the group consisting of Hal, $NO_2$, CN, $R^{3a}$, OH, $OR^{3a}$, $CONHR^{3a}$, $NR^{3a}COR^{3b}$, $SO_2R^{3a}$, $NH_2$, $NHR^{3a}$, $N(R^{3a})_2$, $(CH_2)_q$—$R^6$, and oxo (=O);

q denotes 1, 2, 3, 4, 5, or 6;

m denotes 0, 1, or 2; and

Hal denotes F, Cl, Br, or I;

wherein the immunoregulatory abnormality is an autoimmune or chronic inflammatory disease selected from the group consisting of systemic lupus erythematosus, chronic rheumatoid arthritis, inflammatory bowel disease, multiple sclerosis, amyotrophic lateral sclerosis, atherosclerosis, scleroderma, autoimmune hepatitis, Sjogren Syndrome, lupus nephritis, glomerulonephritis, Rheumatoid Arthritis, Psoriasis, Myasthenia Gravis, Immunoglobulin A nephropathy, Vasculitis, Transplant rejection, Myositis, Henoch-Schönlein Purpura, and asthma;

wherein the cancer is a hematological malignancy or a solid tumor, wherein said hematological malignancy is a disease selected from the group consisting of multiple myeloma, mantle cell lymphoma, diffuse large B-cell lymphoma, plasmacytoma, follicular lymphoma, immunocytoma, acute lymphoblastic leukemia, chronic lymphocytic leukemia, and myeloid leukemia; and wherein the solid tumor is selected from the group consisting of inflammatory breast and colon cancer, lung cancer, head and neck cancer, prostate cancer, pancreas cancer, bladder cancer, renal cancer, hepatocellular cancer, and gastric cancer.

2. The method of claim 1, wherein in the compound of formula (I), $R^1$ and $R^2$ denote each, independently from one another, H or $C_1$-$C_4$-alkyl; or $R^1$ and $R^2$ form together a residue according to the formula (CE); and LY denotes $CH_2$ or $CH_2CH_2$, wherein 1 to 2H atoms may be replaced by at least one selected from the group consisting of Hal, $R^{3a}$, and $OR^{4a}$.

3. The method of claim 1, wherein in the compound of formula (I), $T^1$, $T^2$, $T^3$, $T^4$, $T^5$, $T^6$, $T^7$, $T^8$, and $T^9$ denote O.

4. The method of claim 1, wherein in the compound of formula (I), $P^1$ denotes a linear or branched $C_1$-$C_6$-alkyl or $C_3$-$C_8$-cycloalkyl, each, independently from one another, unsubstituted or mono-, di-, or trisubstituted by at least one selected from the group consisting of Hal, CN, $R^{3a}$, $OR^{3a}$, and $(CH_2)_q$—$R^6$;

$P^2$ denotes phenyl, pyridyl, pyrrolyl, furanyl, thiophenyl, pyrimidyl, pyranzinyl, or pyridazinyl, each, independently from one another, unsubstituted or mono-, di-, or trisubstituted by at least one selected from the group consisting of Hal, CN, $R^{3a}$, OH, $OR^{3a}$, $CONR^{4a}R^{4b}$, $NR^{3a}COR^{3b}$, $SO_2R^{3a}$, $SOR^{3a}$, $NR^{4a}R^{4b}$, $Ar^2$, $Het^2$, $(CH_2)_q$—$SR^{3a}$, $(CH_2)_q$—$N(R^{4a})_2$, and $(CH_2)_q$—$R^6$; and $P^3$ denotes a bicyclic residue of formula (ya), (yb), (yc), (yd), (ye), (yf), (yg), (yh), (yi), (yj), (yk), (yl), (ym), (yn), (yo), or (yp); each, independently from one another, unsubstituted or mono-, di-, or trisubstituted by at least one selected from the group consisting of Hal, CN, $R^{3a}$, OH, $OR^{3a}$, $CONR^{4a}R^{4b}$, $NR^{3a}COR^{3b}$, $SO_2R^{3a}$, $SOR^{3a}$, $NR^{4a}R^{4b}$, $Ar^2$, $Het^2$, $(CH_2)_q$—$SR^{3a}$, $(CH_2)_q$—$N(R^{4a})_2$, and $(CH_2)_q$—$R^6$:

(ya)

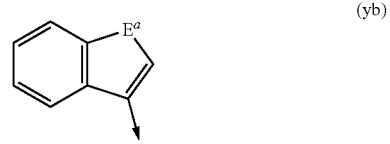

(yb)

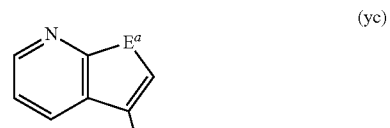

(yc)

(yd)

(ye)

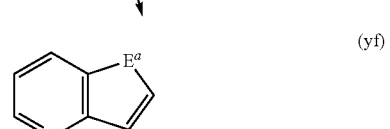

(yf)

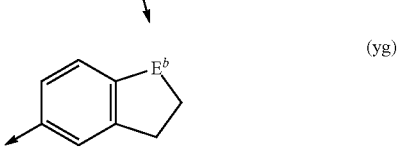

(yg)

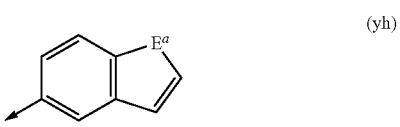

(yh)

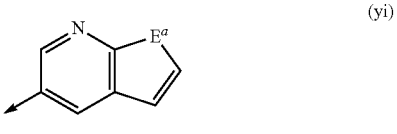

(yi)

-continued

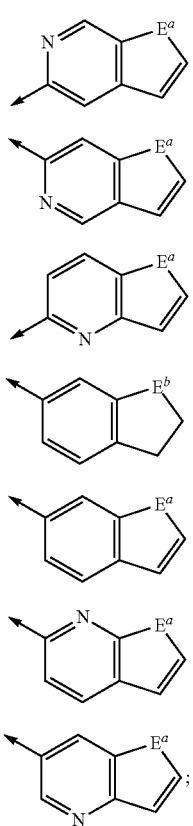

(yj)
(yk)
(yl)
(ym)
(yn)
(yo)
(yp)

wherein
$E^a$ denotes O, S, N(Alk), CH=CH; and
$E^b$ denotes O, S, N(Alk), CH$_2$, CH$_2$—CH$_2$, O—CH$_2$, S—CH$_2$, Or N(Alk)CH$_2$.

5. The method of claim 1, wherein in the compound of formula (I),
$R^{3a}$ and $R^{3b}$ denote each, independently from one another, linear or branched $C_1$-$C_4$-alkyl or $C_3$-$C_6$ cycloalkyl, wherein 1 to 3H atoms may be replaced by at least one selected from the group consisting of F and Cl; and/or wherein 1 or 2H atoms may be replaced by at least one selected from the group consisting of CN, OH, OCH$_3$, and OC$_2$H$_5$.

6. The method of claim 1, wherein in the compound of formula (I),
Y denotes $P^2$ or $P^3$.

7. The method of claim 1, wherein in the compound of formula (I),
the stereogenic center at a carbon atom adjacent to a boronic acid residue has an (R)-configuration according to formula (R)-(I):

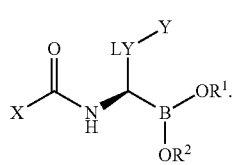

(R)-(I)

8. The method of claim 1, wherein in the compound of formula (I),

X is a heterobicycle or heterotricycle of formula (xa1), (xb1), (xc1), (xd1), (xe1), (xf1), (xg1), (xh1), or (xi1); each, independently from one another, unsubstituted or mono-, di-, or trisubstituted by at least one selected from the group consisting of Hal, NO$_2$, CN, $R^{5a}$, $OR^{5a}$, CONR$^{5a}$, $R^{5b}$, NR$^{5a}$COR$^{5b}$, SO$_2$R$^{5a}$, SOR$^{5a}$, SO$_2$NR$^{5a}$R$^{5b}$, NR$^{5a}$SO$_2$R$^{5b}$, NR$^{5a}$R$^{5b}$, (CH$_2$)$_q$—R$^6$, COR$^{5a}$, and SO$_2$R$^{5a}$; and wherein one of the cyclic CH$_2$ groups may be replaced by at least one selected from the group consisting of CR$^{4a}$R$^{4b}$, C=O, S, NR$^{5a}$, SO, and SO$_2$:

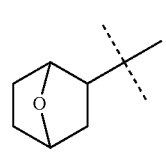
(xa1)

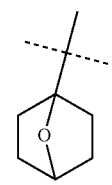
(xb1)

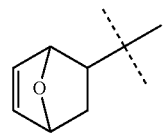
(xc1)

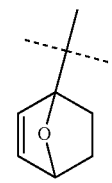
(xd1)

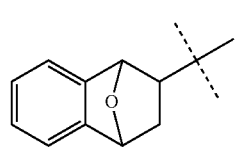
(xe1)

(xf1)

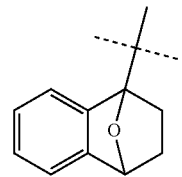
(xg1)

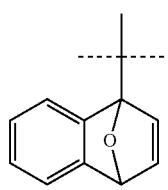

-continued

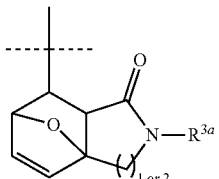
(xh1)

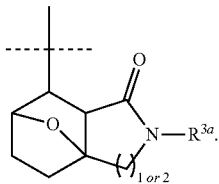
(xi1)

9. The method of claim 1, wherein in the compound of formula (I),
X is a heterobicycle or heterotricycle of formula (xa), (xb), (xc), (xd), (xe), (xf), (xg), (xh), or (xi); each, independently from one another, unsubstituted or mono- or disubstituted by at least one selected from the group consisting of F, Cl, $CH_3$, $C_2H_5$, $CF_3$, $OCH_3$, $OC_2H_5$, $COCF_3$, $SCH_3$, $SC_2H_5$, $CH_2OCH_3$, $N(CH_3)_2$, $CH_2N(CH_3)_2$, and $N(C_2H_5)$.

10. The method of claim 8, wherein in the compound of formula (I),
X is a heterobicycle or heterotricycle of formula (xa1), (xb1), (xc1), (xd1), (xe1), (xf1), (xg1), or (xh1); each, independently from one another, unsubstituted or mono- or disubstituted by at least one selected from the group consisting of F, Cl, $CH_3$, $C_2H_5$, $CF_3$, $OCH_3$, $OC_2H_5$, $COCF_3$, $SCH_3$, $SC_2H_5$, $CH_2OCH_3$, $N(CH_3)_2$, $CH_2N(CH_3)_2$, and $N(C_2H_5)$.

11. The method of claim 1, wherein in the compound of formula (I),
$P^3$ denotes unsubstituted or mono- or disubstituted 1- or 2-naphthyl, wherein optional substituents are selected from the group consisting of Hal, CN, $R^{3a}$, OH, $OR^{3a}$, $CONR^{4a}R^{4b}$, $NR^{3a}COR^{3b}$, $SO_2R^{3a}$, $SOR^{3a}$, $NR^{4a}R^{4b}$, $Ar^2$, $Het^2$, $(CH_2)_q$—$SR^{3a}$, $(CH_2)_q$—$N(R^{4a})_2$ and $(CH_2)_q$—$R^6$;
or
$P^3$ is a residue according to formula ($R^a$) or ($R^b$):

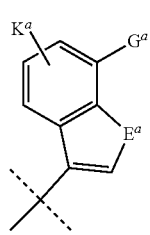
($R^a$)

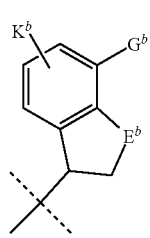
($R^b$)

wherein
$G^a$ and $G^b$ denote each, independently from one another, H, CN, $R^{3a}$, $OR^{3a}$, $CONHR^{3a}$, $CONR^{3b}R^{3a}$, $CONH_2$, $NR^{3a}COR^{3b}$, $SO_2R^{3a}$, $SOR^{3a}$, $NHR^{3a}$, $N(R^{3a})_2$, $(CH_2)_q$—$SR^{3a}$, $(CH_2)_q$—$N(R^{4a})_2$, or $(CH_2)_q$—$R^6$;
$K^a$ and $K^b$ denote each, independently from one another, H, Hal, CN, $R^{3a}$, $OR^{3a}$, $CONHR^{3a}$, $CONR^{3b}R^{3a}$, $CONH_2$, $NR^{3a}COR^{3b}$, $SO_2R^{3a}$, $SOR^{3a}$, $NHR^{3a}$, $N(R^{3a})_2$, $(CH_2)_q$—$SR^{3a}$, $(CH_2)_q$—$N(R^{4a})_2$, or $(CH_2)_q$—$R^6$;
$E^a$ denotes O, S, N(Alk), or CH=CH; and
$E^b$ denotes O, S, N(Alk), $CH_2$, $CH_2$—$CH_2$, O—$CH_2$, S—$CH_2$, or $N(Alk)CH_2$.

12. The method of claim 11, wherein $E^a$ and $E^b$ each denote O or S.

13. The method of claim 11, wherein in the compound of formula (I),
$P^3$ is a residue according to formula ($F^a$) or ($F^b$):

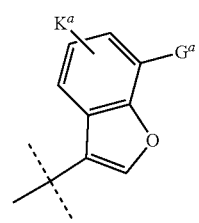
($F^a$)

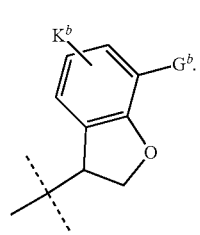
($F^b$)

14. The method of claim 13, wherein in the compound of formula (I),
$P^2$ denotes unsubstituted or mono- or disubstituted 2- or 3-thienyl; or unsubstituted or 3-, 4-, 2,3-, 2,4-, 2,5-, 3,4-, or 2,3,4-substituted phenyl, wherein optional substituents are selected from the group consisting of Hal, CN, $R^{3a}$, OH, $OR^{3a}$, $CONR^{4a}R^{4b}$, $NR^{3a}COR^{3b}$, $SO_2R^{3a}$, $SOR^{3a}$, $NR^{4a}R^{4b}$, $Ar^2$, $Het^2$, $(CH_2)_q$—$SR^{3a}$, $(CH_2)_q$—$N(R^{4a})_2$, and $(CH_2)_q$—$R^6$;
$P^3$ denotes a residue according to formula ($F^a$) or (S)-($F^b$):

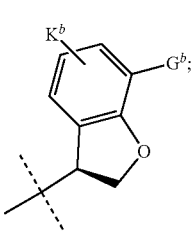
(S)-($F^b$)

$G^a$ and $G^b$ denote each, independently from one another, H, Hal, CN, $R^{3a}$, OH, $OR^{3a}$, $CONR^{4a}R^{4b}$, $NR^{3a}COR^{3b}$, $SO_2R^{3a}$, $SOR^{3a}$, $NR^{4a}R^{4b}$, $Ar^2$, $Het^2$, $(CH_2)_q$—$SR^{3a}$, $(CH_2)_q$—$N(R^{4a})_2$, or $(CH_2)_q$—$R^6$; and K$^a$ and K$^b$ denote each, independently from one another, H, Hal, R$^{3a}$, OH, OR$^{3a}$, CONR$^{4a}$R$^{4b}$, NR$^{3a}$COR$^{3b}$, SO$_2$R$^{3a}$, SOR$^{3a}$, NR$^{4a}$R$^{4b}$, Ar$^2$, Het$^2$, (CH$_2$)$_q$—SR$^{3a}$, (CH$_2$)$_q$—N(R$^{4a}$)$_2$, or (CH$_2$)$_q$—R$^6$.

15. The method of claim 14, wherein in the compound of formula (I),

P$^2$ denotes unsubstituted or mono- or disubstituted 2- or 3-thienyl, or unsubstituted or 3-, 4-, 2,3-, 2,4-, 2,5-, 3,4-, or 2,3,4-substituted phenyl, wherein optional substituents are selected from the group consisting of F, Cl, CN, CH$_3$, C$_2$H$_5$, CF$_3$, OCH$_3$, OC$_2$H$_5$, COCF$_3$, SCH$_3$, SC$_2$H$_5$, CH$_2$OCH$_3$, N(CH$_3$)$_2$, CH$_2$N(CH$_3$)$_2$ and N(C$_2$H$_5$)$_2$;

P$^3$ denotes a residue according to formula (F$^a$) or (S)-(F$^b$);

G$^a$ and G$^b$ denote each, independently from one another, F, Cl, CN, CH$_3$, C$_2$H$_5$, CF$_3$, OCH$_3$, OC$_2$H$_5$, COCF$_3$, SCH$_3$, SC$_2$H$_5$, CH$_2$OCH$_3$, N(CH$_3$)$_2$, CH$_2$N(CH$_3$)$_2$, or N(C$_2$H$_5$)$_2$;

K$^a$ and K$^b$ denote each, independently from one another, H, F, Cl, CN, CH$_3$, C$_2$H$_5$, CF$_3$, OCH$_3$, OC$_2$H$_5$, COCF$_3$, SCH$_3$, SC$_2$H$_5$, CH$_2$OCH$_3$, N(CH$_3$)$_2$, CH$_2$N(CH$_3$)$_2$ or N(C$_2$H$_5$)$_2$.

16. The method of claim 1, wherein the compound of formula (I) is selected from the group consisting of:

[(1R)-2-[(3S)-2,3-dihydro-1-benzofuran-3-yl]-1-{[(1S, 2R,4R)-7-oxabicyclo[2.2.1]heptan-2-yl] formamido}ethyl]boronic acid;

[(1R)-2-[(3S)-2,3-dihydro-1-benzofuran-3-yl]-1-{[(1R, 2S,4S)-7-oxabicyclo[2.2.1]heptan-2-yl] formamido}ethyl]boronic acid;

[(1R)-1-{[(1S,2R,4R)-7-oxabicyclo[2.2.1]heptan-2-yl] formamido}-2-(thiophen-3-yl)ethyl]boronic acid;

[(1R)-2-(1-benzofuran-3-yl)-1-{[(1R,8S)-11-oxatricyclo [6.2.1.0$^{2,7}$]undeca-2(7),3,5-trien-1-yl] formamido}ethyl]boronic acid;

[(1S)-2-(1-benzofuran-3-yl)-1-{[(1R,8S)-11-oxatricyclo [6.2.1.0$^{2,7}$]undeca-2(7),3,5-trien-1-yl] formamido}ethyl]boronic acid;

[(1R)-2-(1-benzofuran-3-yl)-1-{[(1S,8R)-11-oxatricyclo [6.2.1.0$^{2,7}$]undeca-2(7),3,5-trien-1-yl] formamido}ethyl]boronic acid;

[(1S)-2-(1-benzofuran-3-yl)-1-{[(1S,8R)-11-oxatricyclo [6.2.1.0$^{2,7}$]undeca-2(7),3,5-trien-1-yl] formamido}ethyl]boronic acid;

[(1R)-2-(1-benzofuran-3-yl)-1-{[(1R,2S,4S)-7-oxabicyclo[2.2.1]heptan-2-yl]formamido}ethyl]boronic acid;

[(1R)-2-(1-benzofuran-3-yl)-1-{[(1S,2R,4R)-7-oxabicyclo[2.2.1]heptan-2-yl]formamido}ethyl]boronic acid;

[(1R)-2-(1-benzofuran-3-yl)-1-{[(1R,2R,4S)-7-oxabicyclo[2.2.1]heptan-2-yl]formamido}ethyl]boronic acid;

[(1S)-2-(1-benzofuran-3-yl)-1-{[(1R,2R,4S)-7-oxabicyclo[2.2.1]heptan-2-yl]formamido}ethyl]boronic acid;

[(1R)-2-(7-chloro-1-benzofuran-3-yl)-1-{[(1R,2S,4S)-7-oxabicyclo[2.2.1]heptan-2-yl]formamido}ethyl]boronic acid;

[(1R)-2-(7-chloro-1-benzofuran-3-yl)-1-{[(1S,2R,4R)-7-oxabicyclo[2.2.1]heptan-2-yl]formamido}ethyl]boronic acid;

[(1R)-2-[(3R)-7-methyl-2,3-dihydro-1-benzofuran-3-yl]-1-{[(1S,2R,4R)-7-oxabicyclo[2.2.1]heptan-2-yl] formamido}ethyl]boronic acid;

[(1R)-2-[(3S)-7-methyl-2,3-dihydro-1-benzofuran-3-yl]-1-{[(1S,2R,4R)-7-oxabicyclo[2.2.1]heptan-2-yl] formamido}ethyl]boronic acid;

[(1R)-2-[(3S)-2,3-dihydro-1-benzofuran-3-yl]-1-{[(1R, 8S)-11-oxatricyclo[6.2.1.0$^{2,7}$]undeca-2(7),3,5-trien-1-yl]formamido}ethyl]boronic acid;

[(1R)-2-(1-benzofuran-3-yl)-1-{[(1S,6S,7R)-3-cyclopropyl-4-oxo-10-oxa-3-azatricyclo[5.2.1.0$^{1,5}$]dec-8-en-6-yl]formamido}ethyl]boronic acid;

[(1R)-2-[(3S)-2,3-dihydro-1-benzofuran-3-yl]-1-{[(1S, 8R)-11-oxatricyclo[6.2.1.0$^{2,7}$]undeca-2(7),3,5-trien-1-yl]formamido}ethyl]boronic acid;

[(1R)-2-(7-methyl-1-benzofuran-3-yl)-1-{[(1R,8S)-11-oxatricyclo[6.2.1.0$^{2,7}$]undeca-2,4,6-trien-1-yl] formamido}ethyl]boronic acid;

[(1R)-2-(7-methyl-1-benzofuran-3-yl)-1-{[(1S,8R)-11-oxatricyclo[6.2.1.0$^{2,7}$]undeca-2,4,6-trien-1-yl] formamido}ethyl]boronic acid;

[(1R)-2-[(3S)-2,3-dihydro-1-benzofuran-3-yl]-1-{[(1S, 8R)-8-methyl-11-oxatricyclo[6.2.1.0$^{2,7}$]undeca-2,4,6-trien-1-yl]formamido}ethyl]boronic acid;

[(1R)-2-(1-benzofuran-3-yl)-1-{[(1R,8S)-11-oxatricyclo [6.2.1.0$^{2,7}$]undeca-2(7),3,5-trien-9-yl] formamido}ethyl]boronic acid;

[(1R)-2-[(3S)-2,3-dihydro-1-benzofuran-3-yl]-1-{[(1R, 8S)-8-methyl-11-oxatricyclo[6.2.1.0$^{2,7}$]undeca-2,4,6-trien-1-yl]formamido}ethyl]boronic acid;

[(1R)-2-(1-benzofuran-3-yl)-1-{[(1S,8R)-11-oxatricyclo [6.2.1.0$^{2,7}$]undeca-2(7),3,5-trien-9-yl] formamido}ethyl]boronic acid;

[(1R)-2-(2,4-dimethylphenyl)-1-{[(1S,2R,4R)-7-oxabicyclo[2.2.1]heptan-2-yl]formamido}ethyl]boronic acid;

[(1R)-2-cyclohexyl-1-{[(1S,2R,4R)-7-oxabicyclo[2.2.1] heptan-2-yl]formamido}ethyl]boronic acid;

[(1R)-1-{[(1S,2R,4R)-7-oxabicyclo[2.2.1]heptan-2-yl] formamido}-3-phenylpropyl]boronic acid;

[(1R)-3-methyl-1-{[(1S,2R,4R)-7-oxabicyclo[2.2.1]heptan-2-yl]formamido}butyl]boronic acid;

[(1S)-2-(1-benzofuran-3-yl)-1-{[(1S,2R,4R)-7-oxabicyclo[2.2.1]heptan-2-yl]formamido}ethyl]boronic acid;

[(1S)-2-(1-benzofuran-3-yl)-1-{[(1R,2S,4S)-7-oxabicyclo[2.2.1]heptan-2-yl]formamido}ethyl]boronic acid;

[(1R)-2-(1-benzofuran-3-yl)-1-{[(1S,2S,4S)-7-oxabicyclo[2.2.1]heptan-2-yl]formamido}ethyl]boronic acid;

[(1S)-2-(1-benzofuran-3-yl)-1-{[(1S,2S,4S)-7-oxabicyclo[2.2.1]heptan-2-yl]formamido}ethyl]boronic acid;

[(1R)-2-[(3S)-2,3-dihydro-1-benzofuran-3-yl]-1-{[(1S, 2S,4R)-7-oxabicyclo[2.2.1]heptan-2-yl] formamido}ethyl]boronic acid;

[(1R)-2-[(3S)-2,3-dihydro-1-benzofuran-3-yl]-1-{[(1R, 2R,4S)-7-oxabicyclo[2.2.1]heptan-2-yl] formamido}ethyl]boronic acid;

[(1S)-2-[(3S)-2,3-dihydro-1-benzofuran-3-yl]-1-{[(1S, 2S,4R)-7-oxabicyclo[2.2.1]heptan-2-yl] formamido}ethyl]boronic acid;

[(1S)-2-[(3S)-2,3-dihydro-1-benzofuran-3-yl]-1-{[(1R, 2R,4S)-7-oxabicyclo[2.2.1]heptan-2-yl] formamido}ethyl]boronic acid;

[(1R)-2-[(3R)-2,3-dihydro-1-benzofuran-3-yl]-1-{[(1S, 2S,4R)-7-oxabicyclo[2.2.1]heptan-2-yl] formamido}ethyl]boronic acid;

[(1R)-2-[(3R)-2,3-dihydro-1-benzofuran-3-yl]-1-{[(1R, 2R,4S)-7-oxabicyclo[2.2.1]heptan-2-yl] formamido}ethyl]boronic acid;

[(1S)-2-[(3R)-2,3-dihydro-1-benzofuran-3-yl]-1-{[(1S, 2S,4R)-7-oxabicyclo[2.2.1]heptan-2-yl] formamido}ethyl]boronic acid;

[(1S)-2-[(3R)-2,3-dihydro-1-benzofuran-3-yl]-1-{[(1R, 2R,4S)-7-oxabicyclo[2.2.1]heptan-2-yl] formamido}ethyl]boronic acid;

[(1S)-2-[(3S)-2,3-dihydro-1-benzofuran-3-yl]-1-{[(1S, 2R,4R)-7-oxabicyclo[2.2.1]heptan-2-yl] formamido}ethyl]boronic acid;

[(1S)-2-[(3S)-2,3-dihydro-1-benzofuran-3-yl]-1-{[(1R, 2S,4S)-7-oxabicyclo[2.2.1]heptan-2-yl] formamido}ethyl]boronic acid;

[(1R)-2-[(3R)-2,3-dihydro-1-benzofuran-3-yl]-1-{[(1S, 2R,4R)-7-oxabicyclo[2.2.1]heptan-2-yl] formamido}ethyl]boronic acid;

[(1R)-2-[(3R)-2,3-dihydro-1-benzofuran-3-yl]-1-{[(1R, 2S,4S)-7-oxabicyclo[2.2.1]heptan-2-yl] formamido}ethyl]boronic acid;

[(1S)-2-[(3R)-2,3-dihydro-1-benzofuran-3-yl]-1-{[(1S, 2R,4R)-7-oxabicyclo[2.2.1]heptan-2-yl] formamido}ethyl]boronic acid;

[(1S)-2-[(3R)-2,3-dihydro-1-benzofuran-3-yl]-1-{[(1R, 2S,4S)-7-oxabicyclo[2.2.1]heptan-2-yl] formamido}ethyl]boronic acid.

* * * * *